(12) United States Patent
Bankiewicz et al.

(10) Patent No.: US 12,318,183 B2
(45) Date of Patent: *Jun. 3, 2025

(54) METHODS FOR BIOMEDICAL TARGETING AND DELIVERY AND DEVICES AND SYSTEMS FOR PRACTICING THE SAME

(71) Applicant: The Regents of the University of California, Oakland, CA (US)

(72) Inventors: Krystof S. Bankiewicz, Oakland, CA (US); Kathryn H. Rosenbluth, San Francisco, CA (US); Adrian P. Kells, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 537 days.

This patent is subject to a terminal disclaimer.

(21) Appl. No.: 17/689,275

(22) Filed: Mar. 8, 2022

(65) Prior Publication Data

US 2022/0296118 A1    Sep. 22, 2022

Related U.S. Application Data

(63) Continuation of application No. 16/562,260, filed on Sep. 5, 2019, now Pat. No. 11,298,043, which is a
(Continued)

(51) Int. Cl.
*A61B 5/05* (2021.01)
*A61B 5/00* (2006.01)
(Continued)

(52) U.S. Cl.
CPC ............ *A61B 5/055* (2013.01); *A61B 5/1071* (2013.01); *A61B 5/1072* (2013.01);
(Continued)

(58) Field of Classification Search
CPC ....... A61B 5/055; A61B 5/6835; A61B 90/11; A61B 6/04; A61B 5/1071; A61B 5/1127;
(Continued)

(56) References Cited

U.S. PATENT DOCUMENTS 5,064,764 A   11/1991   Besnainon
5,163,430 A   11/1992   Carol
(Continued)

FOREIGN PATENT DOCUMENTS

CA   2109955 A1   11/1992
CA   2259214 A1   12/1997
(Continued)

OTHER PUBLICATIONS

Adachi et al. (2014) "Drawing a high-resolution functional map of adeno-associated virus capsid by massively parallel sequencing." Nature Communications, 5:3075 1-14.
(Continued)

*Primary Examiner* — Joel Lamprecht
(74) *Attorney, Agent, or Firm* — Edward J. Baba; Michael J. Blessent; Bozicevic, Field & Francis LLP

(57) ABSTRACT

The present disclosure provides methods for targeting a biomedical system. Aspects of the subject methods include determining the trajectory of a targeting device using magnetic resonance imaging (MRI) of a MRI-visible style of a trajectory guide that is compatible with the targeting device. Targeted biomedical systems may be utilized for a variety of purposes including targeted delivery of a therapeutic, holding a therapeutic device, positioning of a therapeutic device and other uses. Also provided are devices and systems that can be used in practicing the described methods including but not limited to trajectory guides and adjustable targeting systems, as well as non-transitory computer readable medium storing instructions that, when executed by a com-
(Continued)

puting device, cause a computing device to perform steps of the described methods.

13 Claims, 10 Drawing Sheets

Related U.S. Application Data continuation of application No. 16/222,763, filed on Dec. 17, 2018, now Pat. No. 10,426,375, which is a continuation of application No. 16/039,044, filed on Jul. 18, 2018, now Pat. No. 10,426,374, which is a continuation of application No. PCT/US2017/049191, filed on Aug. 29, 2017.

(60) Provisional application No. 62/381,423, filed on Aug. 30, 2016.

(51) Int. Cl.
  *A61B 5/055* (2006.01)
  *A61B 5/107* (2006.01)
  *A61B 5/11* (2006.01)
  *A61B 6/03* (2006.01)
  *A61B 6/04* (2006.01)
  *A61B 34/10* (2016.01)
  *A61B 90/11* (2016.01)
  *A61B 17/00* (2006.01)

(52) U.S. Cl.
  CPC .......... *A61B 5/1127* (2013.01); *A61B 5/6835* (2013.01); *A61B 6/03* (2013.01); *A61B 6/04* (2013.01); *A61B 34/10* (2016.02); *A61B 90/11* (2016.02); *A61B 2017/00911* (2013.01); *A61B 2034/107* (2016.02); *A61B 2505/05* (2013.01); *A61B 2560/0475* (2013.01); *A61B 2576/026* (2013.01)

(58) Field of Classification Search
  CPC ....... A61B 6/03; A61B 5/1072; A61B 5/0555; A61B 2017/00911; A61B 2034/107; A61B 34/10; A61B 2560/0475; A61B 2576/026; A61B 2505/05
  See application file for complete search history.

(56) References Cited

U.S. PATENT DOCUMENTS

| | | |
|---|---|---|
| 5,163,773 A | 11/1992 | Denney et al. |
| 5,474,935 A | 12/1995 | Chatterjee |
| 5,487,739 A | 1/1996 | Aebischer |
| 5,538,885 A | 7/1996 | Hollis |
| 5,569,267 A | 10/1996 | Howard, III |
| 5,587,308 A | 12/1996 | Carter |
| 5,643,286 A | 7/1997 | Warner |
| 5,652,224 A | 7/1997 | Wilson |
| 5,658,785 A | 8/1997 | Johnson |
| 5,676,655 A | 10/1997 | Howard, III et al. |
| 5,688,676 A | 11/1997 | Zhou |
| 5,691,176 A | 11/1997 | Lebkowski |
| 5,693,531 A | 12/1997 | Chiorini |
| 5,713,858 A | 2/1998 | Heruth |
| 5,741,683 A | 4/1998 | Zhou |
| 5,756,283 A | 5/1998 | Wilson |
| 5,776,143 A | 7/1998 | Adams |
| 5,776,144 A | 7/1998 | Leysieffer |
| 5,788,713 A | 8/1998 | Dubach |
| 5,792,110 A | 8/1998 | Cunningham |
| 5,856,152 A | 1/1999 | Wilson |
| 5,858,351 A | 1/1999 | Podsakoff |
| 5,858,775 A | 1/1999 | Johnson |
| 5,865,842 A | 2/1999 | Knuth |
| 5,866,552 A | 2/1999 | Wilson |
| 5,866,696 A | 2/1999 | Carter |
| 5,871,487 A | 2/1999 | Warner |
| 5,871,982 A | 2/1999 | Wilson |
| 5,913,852 A | 6/1999 | Magram |
| 5,927,277 A | 7/1999 | Baudino |
| 5,952,221 A | 9/1999 | Kurtzman |
| 5,954,687 A | 9/1999 | Baudino |
| 5,962,313 A | 10/1999 | Podsakoff |
| 5,989,540 A | 11/1999 | Carter |
| 5,993,463 A | 11/1999 | Truwit |
| 6,061,587 A | 5/2000 | Kucharczyk |
| 6,083,716 A | 7/2000 | Wilson |
| 6,143,548 A | 11/2000 | Oriordan |
| 6,143,567 A | 11/2000 | Van |
| 6,146,874 A | 11/2000 | Zolotukhin |
| 6,156,303 A | 12/2000 | Russell |
| 6,165,139 A | 12/2000 | Damadian |
| 6,174,527 B1 | 1/2001 | Wilson |
| 6,180,613 B1 | 1/2001 | Kaplitt |
| 6,190,393 B1 | 2/2001 | Bevier |
| 6,194,191 B1 | 2/2001 | Zhang |
| 6,195,577 B1 | 2/2001 | Truwit |
| 6,200,560 B1 | 3/2001 | Couto |
| 6,204,059 B1 | 3/2001 | Samulski |
| 6,206,890 B1 | 3/2001 | Truwit |
| 6,211,163 B1 | 4/2001 | Podsakoff |
| 6,214,016 B1 | 4/2001 | Williams |
| 6,251,677 B1 | 6/2001 | Wilson |
| 6,258,595 B1 | 7/2001 | Gao |
| 6,261,241 B1 | 7/2001 | Burbank |
| 6,261,300 B1 | 7/2001 | Day |
| 6,261,551 B1 | 7/2001 | Wilson |
| 6,265,389 B1 | 7/2001 | Burke |
| 6,267,769 B1 | 7/2001 | Truwit |
| 6,270,996 B1 | 8/2001 | Wilson |
| 6,274,354 B1 | 8/2001 | Wilson |
| 6,281,010 B1 | 8/2001 | Gao |
| 6,309,634 B1 | 10/2001 | Bankiewicz |
| 6,325,998 B1 | 12/2001 | Podsakoff |
| 6,335,011 B1 | 1/2002 | Podsakoff |
| 6,353,762 B1 | 3/2002 | Baudino |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,490,467 B1 | 12/2002 | Bucholz |
| 6,503,888 B1 | 1/2003 | Kaplitt |
| 6,509,150 B1 | 1/2003 | Salvetti |
| 6,521,426 B1 | 2/2003 | Ciliberto |
| 6,529,765 B1 | 3/2003 | Franck |
| 6,537,232 B1 | 3/2003 | Kucharczyk |
| 6,537,241 B1 | 3/2003 | Odland |
| 6,555,525 B2 | 4/2003 | Burke |
| 6,566,118 B1 | 5/2003 | Atkinson |
| 6,567,687 B2 | 5/2003 | Front |
| 6,572,624 B2 | 6/2003 | U |
| 6,582,692 B1 | 6/2003 | Podsakoff |
| 6,593,123 B1 | 7/2003 | Wright |
| 6,599,267 B1 | 7/2003 | Ray |
| 6,602,241 B2 | 8/2003 | Makower |
| 6,609,020 B2 | 8/2003 | Gill |
| 6,610,290 B2 | 8/2003 | Podsakoff |
| 6,623,490 B1 | 9/2003 | Crane |
| 6,632,184 B1 | 10/2003 | Truwit |
| 6,642,051 B1 | 11/2003 | Lynch |
| 6,656,152 B2 | 12/2003 | Putz |
| 6,660,514 B1 | 12/2003 | Zololukhin et al. |
| 6,660,521 B2 | 12/2003 | Brough |
| 6,670,176 B1 | 12/2003 | Samulski |

(56) References Cited

U.S. PATENT DOCUMENTS

| | | |
|---|---|---|
| 6,676,669 B2 | 1/2004 | Charles |
| 6,676,935 B2 | 1/2004 | Henderson |
| 6,699,706 B1 | 3/2004 | Brooks |
| 6,702,782 B2 | 3/2004 | Miller |
| 6,710,036 B2 | 3/2004 | Kurtzman |
| 6,723,551 B2 | 4/2004 | Kotin |
| 6,726,907 B1 | 4/2004 | Zhang |
| 6,752,812 B1 | 6/2004 | Truwit |
| 6,753,419 B1 | 6/2004 | Toniatti |
| 6,759,237 B1 | 7/2004 | Wilson |
| 6,773,443 B2 | 8/2004 | Truwit |
| 6,793,664 B2 | 9/2004 | Mazzocchi |
| 6,795,737 B2 | 9/2004 | Gielen |
| 6,841,357 B1 | 1/2005 | Vaillancourt |
| 6,846,665 B1 | 1/2005 | Horer |
| 6,855,314 B1 | 2/2005 | Chiorini |
| 6,887,463 B2 | 5/2005 | Wilson |
| 6,889,073 B2 | 5/2005 | Lampman |
| 6,897,045 B2 | 5/2005 | Engelhardt |
| 6,902,569 B2 | 6/2005 | Parmer |
| 6,918,881 B2 | 7/2005 | Miller |
| 6,939,318 B2 | 9/2005 | Stenzel |
| 6,943,019 B2 | 9/2005 | Wilson |
| 6,953,575 B2 | 10/2005 | Bankiewicz |
| 6,953,690 B1 | 10/2005 | Gao |
| 6,974,448 B2 | 12/2005 | Petersen |
| 6,984,517 B1 | 1/2006 | Chiorini |
| 6,989,015 B2 | 1/2006 | Daum |
| 6,995,006 B2 | 2/2006 | Atkinson |
| 7,015,026 B2 | 3/2006 | Oriordan |
| 7,022,519 B2 | 4/2006 | Gao |
| 7,033,326 B1 | 4/2006 | Pianca |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,103,418 B2 | 9/2006 | Laske |
| 7,105,345 B2 | 9/2006 | Wilson |
| 7,112,321 B2 | 9/2006 | Wang |
| 7,122,038 B2 | 10/2006 | Thomas |
| 7,125,705 B2 | 10/2006 | Colosi |
| 7,125,706 B2 | 10/2006 | Zhang |
| 7,169,612 B2 | 1/2007 | Kostenis |
| 7,182,944 B2 | 2/2007 | Bankiewicz |
| 7,186,552 B2 | 3/2007 | Wilson |
| 7,198,951 B2 | 4/2007 | Gao |
| 7,217,276 B2 | 5/2007 | Henderson |
| 7,223,585 B2 | 5/2007 | Coffey |
| 7,235,084 B2 | 6/2007 | Skakoon |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kolin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,309,317 B2 | 12/2007 | Miller |
| 7,313,430 B2 | 12/2007 | Urquhart |
| 7,319,002 B2 | 1/2008 | Wilson |
| 7,322,954 B2 | 1/2008 | Putz |
| 7,326,555 B2 | 2/2008 | Konz |
| 7,343,205 B1 | 3/2008 | Pianca |
| 7,344,872 B2 | 3/2008 | Gao |
| 7,366,561 B2 | 4/2008 | Mills |
| 7,369,899 B2 | 5/2008 | Malinowski |
| 7,412,276 B2 | 8/2008 | Halperin |
| 7,419,817 B2 | 9/2008 | Chiorini |
| 7,419,956 B2 | 9/2008 | Tetsuya |
| 7,445,930 B2 | 11/2008 | Zhang |
| 7,465,292 B2 | 12/2008 | Putz |
| 7,466,303 B2 | 12/2008 | Yi |
| 7,479,554 B2 | 1/2009 | Chiorini |
| 7,491,508 B2 | 2/2009 | Roy |
| 7,505,807 B1 | 3/2009 | Kucharczyk |
| 7,510,872 B2 | 3/2009 | Clark |
| 7,510,875 B2 | 3/2009 | Zhang |
| 7,534,613 B2 | 5/2009 | Bankiewicz |
| 7,559,935 B2 | 7/2009 | Solar |
| 7,579,181 B2 | 8/2009 | Oriordan |
| 7,588,757 B2 | 9/2009 | Ozawa |
| 7,588,772 B2 | 9/2009 | Kay |
| 7,604,644 B2 | 10/2009 | Schulte |
| 7,608,064 B2 | 10/2009 | Putz |
| 7,625,347 B2 | 12/2009 | Burbank |
| 7,625,570 B1 | 12/2009 | Schaffer |
| 7,638,120 B2 | 12/2009 | Liu |
| 7,660,621 B2 | 2/2010 | Skakoon |
| 7,662,627 B2 | 2/2010 | Johnson |
| 7,695,480 B2 | 4/2010 | Solar |
| 7,704,492 B2 | 4/2010 | Podsakoff |
| 7,704,721 B2 | 4/2010 | Wright |
| 7,717,871 B2 | 5/2010 | Odland |
| 7,732,129 B1 | 6/2010 | Zhang |
| 7,780,679 B2 | 8/2010 | Bobo, Sr. |
| 7,790,449 B2 | 9/2010 | Gao |
| 7,803,622 B2 | 9/2010 | Engelhardt |
| 7,819,842 B2 | 10/2010 | Kaemmerer |
| 7,822,460 B2 | 10/2010 | Halperin |
| 7,837,668 B2 | 11/2010 | Gasmi |
| 7,838,277 B2 | 11/2010 | Gao |
| 7,842,055 B2 | 11/2010 | Pintor |
| 7,879,045 B2 | 2/2011 | Gielen |
| 7,888,096 B2 | 2/2011 | Wu |
| 7,901,921 B2 | 3/2011 | Coffey |
| 7,906,111 B2 | 3/2011 | Wilson |
| 7,925,328 B2 | 4/2011 | Urquhart |
| 7,968,333 B2 | 6/2011 | Yu |
| 7,976,530 B2 | 7/2011 | Johnson |
| 7,981,120 B2 | 7/2011 | Mazzocchi |
| 7,988,674 B2 | 8/2011 | Adams |
| RE42,856 E | 10/2011 | Karmarkar et al. |
| 8,055,351 B2 | 11/2011 | Atalar et al. |
| 8,092,429 B2 | 1/2012 | Gasmi |
| 8,099,150 B2 | 1/2012 | Piferi et al. |
| 8,105,574 B2 | 1/2012 | Wilson |
| 8,108,028 B2 | 1/2012 | Karmarkar |
| 8,110,351 B2 | 2/2012 | Bosnes |
| 8,128,600 B2 | 3/2012 | Gill |
| 8,137,948 B2 | 3/2012 | Qu |
| 8,151,798 B2 | 4/2012 | Thomas |
| 8,157,828 B2 | 4/2012 | Piferi |
| 8,163,543 B2 | 4/2012 | Urabe |
| 8,175,677 B2 | 5/2012 | Sayler et al. |
| 8,182,460 B2 | 5/2012 | Kaplitt |
| 8,195,272 B2 | 6/2012 | Piferi et al. |
| 8,208,993 B2 | 6/2012 | Piferi et al. |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,309,355 B2 | 11/2012 | Bankiewicz |
| 8,315,689 B2 | 11/2012 | Jenkins et al. |
| 8,318,480 B2 | 11/2012 | Gao |
| 8,318,687 B2 | 11/2012 | Tabira |
| 8,320,990 B2 | 11/2012 | Vij |
| 8,340,743 B2 | 12/2012 | Jenkins et al. |
| 8,357,175 B2 | 1/2013 | Mark |
| 8,369,930 B2 | 2/2013 | Jenkins et al. |
| 8,374,677 B2 | 2/2013 | Piferi et al. |
| 8,380,277 B2 | 2/2013 | Atalar et al. |
| 8,394,386 B2 | 3/2013 | Wilson |
| 8,396,532 B2 | 3/2013 | Jenkins et al. |
| 8,409,842 B2 | 4/2013 | Clark |
| 8,430,888 B2 | 4/2013 | Malinowski |
| 8,433,421 B2 | 4/2013 | Atalar et al. |
| 8,460,328 B2 | 6/2013 | Piferi |
| 8,467,852 B2 | 6/2013 | Csavoy |
| 8,470,310 B2 | 6/2013 | Roy |
| 8,475,468 B2 | 7/2013 | Leckrone |
| 8,476,418 B2 | 7/2013 | Mueller |

(56) References Cited

U.S. PATENT DOCUMENTS

| | | |
|---|---|---|
| 8,480,626 B2 | 7/2013 | Nelson |
| 8,509,876 B2 | 8/2013 | Karmarkar |
| 8,512,981 B2 | 8/2013 | Hermens |
| 8,524,219 B2 | 9/2013 | Roy |
| 8,524,446 B2 | 9/2013 | Gao |
| 8,548,569 B2 | 10/2013 | Piferi et al. |
| 8,591,522 B2 | 11/2013 | Solar |
| 8,600,479 B2 | 12/2013 | Dalke |
| 8,603,459 B2 | 12/2013 | Wilson |
| 8,614,101 B2 | 12/2013 | Vandine |
| 8,617,180 B2 | 12/2013 | Thiran |
| RE44,736 E | 1/2014 | Karmarkar et al. |
| 8,637,255 B2 | 1/2014 | Wilson |
| 8,642,314 B2 | 2/2014 | Bakker |
| 8,644,906 B2 | 2/2014 | Piferi et al. |
| 8,649,842 B2 | 2/2014 | Atalar et al. |
| 8,685,734 B2 | 4/2014 | Coffey |
| 8,688,226 B2 | 4/2014 | Atalar et al. |
| 8,688,238 B2 | 4/2014 | Gerber |
| 8,697,417 B2 | 4/2014 | Bakker |
| 8,697,665 B2 | 4/2014 | Fontanellas Rom |
| 8,706,194 B2 | 4/2014 | Wurmfeld |
| 8,747,419 B2 | 6/2014 | Solar |
| 8,753,314 B2 | 6/2014 | Mendez |
| 8,768,433 B2 | 7/2014 | Jenkins et al. |
| 8,788,043 B2 | 7/2014 | Malinowski |
| 8,801,629 B2 | 8/2014 | Tu |
| 8,825,133 B2 | 9/2014 | Jenkins et al. |
| 8,834,863 B2 | 9/2014 | Roy |
| 8,845,655 B2 | 9/2014 | Henderson |
| 8,845,656 B2 | 9/2014 | Skakoon |
| 8,846,030 B2 | 9/2014 | Englehardt |
| 8,846,389 B2 | 9/2014 | Chiorini |
| 8,864,790 B2 | 10/2014 | Strauss |
| 8,870,892 B2 | 10/2014 | Feng |
| 8,886,288 B2 | 11/2014 | Jenkins et al. |
| 8,886,331 B2 | 11/2014 | Labadie |
| 8,906,387 B2 | 12/2014 | Kay |
| 8,906,675 B2 | 12/2014 | Gao |
| 8,909,320 B2 | 12/2014 | Jenkins et al. |
| 8,927,514 B2 | 1/2015 | Chatterjee |
| 8,945,089 B2 | 2/2015 | Johnson |
| 8,961,535 B2 | 2/2015 | Burg |
| 8,962,330 B2 | 2/2015 | Gao |
| 8,962,332 B2 | 2/2015 | Gao |
| 8,979,871 B2 | 3/2015 | Tyc |
| 8,992,458 B2 | 3/2015 | Singh |
| 8,999,678 B2 | 4/2015 | Vandenberghe |
| 9,031,636 B2 | 5/2015 | Piferi |
| 9,039,615 B2 | 5/2015 | Flint |
| 9,042,958 B2 | 5/2015 | Karmarkar et al. |
| 9,050,299 B2 | 6/2015 | Bankiewicz |
| 9,051,542 B2 | 6/2015 | Wright |
| 9,055,884 B2 | 6/2015 | Piferi et al. |
| 9,056,185 B2 | 6/2015 | Fischell |
| 9,056,892 B2 | 6/2015 | Pun |
| 9,067,028 B2 | 6/2015 | Mendez |
| 9,072,863 B2 | 7/2015 | Bennett |
| 9,078,588 B2 | 7/2015 | Ghidoli et al. |
| 9,080,183 B2 | 7/2015 | Klein |
| 9,089,667 B2 | 7/2015 | Bankiewicz |
| 9,097,756 B2 | 8/2015 | Piferi |
| 9,102,943 B2 | 8/2015 | Shinmura |
| 9,102,949 B2 | 8/2015 | Gao |
| 9,113,949 B2 | 8/2015 | Nelson |
| 9,115,373 B2 | 8/2015 | Hermens |
| 9,125,676 B2 | 9/2015 | Sahni |
| 9,163,260 B2 | 10/2015 | Wilson |
| 9,179,857 B2 | 11/2015 | Lee et al. |
| 9,192,393 B2 | 11/2015 | Piferi et al. |
| 9,192,446 B2 | 11/2015 | Piferi et al. |
| 9,198,687 B2 | 12/2015 | Fulkerson |
| 9,211,157 B2 | 12/2015 | Tyc |
| 9,217,155 B2 | 12/2015 | Gao |
| 9,217,159 B2 | 12/2015 | Roy |
| 9,228,174 B2 | 1/2016 | Noordman |
| 9,232,977 B1 | 1/2016 | Rehman |
| 9,233,174 B2 | 1/2016 | Chen |
| 9,238,800 B2 | 1/2016 | Bossis |
| 9,242,090 B2 | 1/2016 | Atalar et al. |
| 9,247,895 B2 | 2/2016 | Venkatesan |
| 9,248,256 B2 | 2/2016 | Takagi |
| 9,248,270 B2 | 2/2016 | Karmarkar et al. |
| 9,259,290 B2 | 2/2016 | Jenkins et al. |
| 9,260,724 B2 | 2/2016 | Bakker |
| 9,283,357 B2 | 3/2016 | Stedman |
| 9,289,270 B2 | 3/2016 | Gielen |
| 9,291,692 B2 | 3/2016 | Yang |
| 9,302,070 B2 | 4/2016 | Bankiewicz |
| 9,314,305 B2 | 4/2016 | Jenkins et al. |
| 9,327,096 B2 | 5/2016 | Herweck |
| 9,345,499 B2 | 5/2016 | Strauss |
| 9,345,875 B2 | 5/2016 | Appenrodt et al. |
| 9,408,629 B2 | 8/2016 | Flint |
| 9,439,979 B2 | 9/2016 | Chiorini |
| 9,441,206 B2 | 9/2016 | Grieger |
| 9,441,244 B2 | 9/2016 | Schaffer |
| 9,445,793 B2 | 9/2016 | Solar |
| 9,447,433 B2 | 9/2016 | Hirsch |
| 9,452,241 B2 | 9/2016 | Gill |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,486,170 B2 | 11/2016 | Andrews |
| 9,492,121 B2 | 11/2016 | Andrews |
| 9,492,415 B2 | 11/2016 | Bankiewicz |
| 9,493,788 B2 | 11/2016 | Gao |
| 9,498,248 B2 | 11/2016 | Nelson |
| 9,498,290 B2 | 11/2016 | Peter |
| 9,498,575 B2 | 11/2016 | Piferi |
| 9,506,083 B2 | 11/2016 | Arbetman |
| 9,510,909 B2 | 12/2016 | Grant |
| 9,528,126 B2 | 12/2016 | Qu |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,572,928 B2 | 2/2017 | Shifflette |
| 9,579,368 B2 | 2/2017 | Bratbak |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,629,658 B2 | 4/2017 | Barker |
| 9,636,370 B2 | 5/2017 | McCown |
| 9,643,325 B2 | 5/2017 | Berkelman |
| 9,649,161 B2 | 5/2017 | Lee |
| 9,649,162 B2 | 5/2017 | Lee |
| 9,662,472 B2 | 5/2017 | Cunningham |
| 9,669,188 B2 | 6/2017 | Echarri |
| 9,669,198 B2 | 6/2017 | Broaddus |
| 9,670,507 B2 | 6/2017 | Xiao |
| 9,675,783 B2 | 6/2017 | Asaad |
| 9,677,088 B2 | 6/2017 | Nakai |
| 9,677,089 B2 | 6/2017 | Gao |
| 9,682,193 B2 | 6/2017 | Anand |
| 9,700,342 B2 | 7/2017 | Andrews |
| 9,700,350 B2 | 7/2017 | Barker |
| 9,750,623 B2 | 9/2017 | Wainwright |
| 9,763,745 B2 | 9/2017 | Karmarkar |
| 9,820,723 B2 | 11/2017 | Lee |
| 9,827,046 B2 | 11/2017 | Rurling |
| 9,849,266 B2 | 12/2017 | Thomson |

(56) References Cited

U.S. PATENT DOCUMENTS

| | | |
|---|---|---|
| 9,891,296 B2 | 2/2018 | Piferi |
| 9,901,400 B2 | 2/2018 | Gowda |
| 10,065,021 B2 | 9/2018 | Grahn |
| 10,076,387 B2 | 9/2018 | Nelson |
| 10,092,367 B2 | 10/2018 | Andrews |
| 10,099,034 B2 | 10/2018 | Lim |
| 10,105,485 B2 | 10/2018 | Piferi |
| 10,105,518 B2 | 10/2018 | Hansen |
| 10,118,004 B2 | 11/2018 | Fischell |
| 10,130,440 B2 | 11/2018 | Gowda |
| 10,130,789 B2 | 11/2018 | Shimada |
| 10,159,782 B2 | 12/2018 | Elias |
| 10,182,879 B2 | 1/2019 | Piecuch |
| 10,188,462 B2 | 1/2019 | Tyc |
| 10,194,890 B2 | 2/2019 | Cosgrove |
| 10,206,693 B2 | 2/2019 | Piferi |
| 10,207,080 B2 | 2/2019 | Lee |
| 10,208,318 B2 | 2/2019 | Barkats |
| 10,214,572 B2 | 2/2019 | Boye |
| 10,219,873 B2 | 3/2019 | Gowda |
| 10,226,616 B2 | 3/2019 | Barker |
| 10,245,388 B2 | 4/2019 | Cabrera Aquino |
| 10,245,413 B2 | 4/2019 | Shimada |
| 10,300,268 B2 | 5/2019 | Skakoon |
| 10,307,220 B2 | 6/2019 | Piferi |
| 10,342,632 B2 | 7/2019 | Andrews |
| 10,357,281 B2 | 7/2019 | Piferi |
| 10,357,631 B2 | 7/2019 | Jackson |
| 10,357,632 B2 | 7/2019 | Herweck |
| 10,376,327 B2 | 8/2019 | Jenkins |
| 10,376,333 B2 | 8/2019 | Piferi |
| 10,426,374 B2 * | 10/2019 | Bankiewicz ............. A61B 6/03 |
| 10,426,375 B2 * | 10/2019 | Bankiewicz ........... A61B 5/055 |
| 10,456,201 B1 | 10/2019 | Solar |
| 10,456,212 B2 | 10/2019 | Gonzalez-Martinez |
| 10,456,555 B2 | 10/2019 | Garrison |
| 10,478,535 B2 | 11/2019 | Ogle |
| 10,485,952 B2 | 11/2019 | Garrison |
| 10,492,881 B2 | 12/2019 | Karmarkar |
| 10,531,882 B2 | 1/2020 | Anand |
| 10,548,630 B2 | 2/2020 | Swaney |
| 10,561,527 B2 | 2/2020 | Rozenberg |
| 10,569,013 B2 | 2/2020 | Piferi |
| 10,576,246 B2 | 3/2020 | Fischell |
| 10,576,247 B2 | 3/2020 | Flores |
| 10,595,744 B2 | 3/2020 | Sayler |
| 10,596,353 B2 | 3/2020 | Flores |
| 10,610,207 B2 | 4/2020 | Pretre |
| 10,625,045 B2 | 4/2020 | McNeese |
| 10,716,593 B2 | 7/2020 | Chieng |
| 10,716,834 B2 | 7/2020 | Bratbak |
| 10,722,265 B1 | 7/2020 | Davis |
| 10,751,137 B2 | 8/2020 | Zastrozna |
| 10,751,513 B2 | 8/2020 | Gill |
| 10,758,264 B2 | 9/2020 | Bankiewicz |
| 2001/0006955 A1 | 7/2001 | Wilson |
| 2001/0014771 A1 | 8/2001 | Truwit |
| 2001/0049144 A1 | 12/2001 | Rivera |
| 2002/0019050 A1 | 2/2002 | Gao |
| 2002/0019641 A1 | 2/2002 | Truwit |
| 2002/0037867 A1 | 3/2002 | Wilson |
| 2002/0052610 A1 | 5/2002 | Skakoon |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0023230 A1 | 1/2003 | Lewis |
| 2003/0032613 A1 | 2/2003 | Gao |
| 2003/0040753 A1 | 2/2003 | Daum |
| 2003/0073934 A1 | 4/2003 | Putz |
| 2003/0092161 A1 | 5/2003 | Gao |
| 2003/0093105 A1 | 5/2003 | Huffmaster |
| 2003/0096264 A1 | 5/2003 | Altar |
| 2003/0100115 A1 | 5/2003 | Raj |
| 2003/0114876 A1 | 6/2003 | Samset |
| 2003/0119191 A1 | 6/2003 | Gao |
| 2003/0138772 A1 | 7/2003 | Gao |
| 2003/0199831 A1 | 10/2003 | Morris |
| 2004/0006302 A1 | 1/2004 | Chaouk |
| 2004/0024308 A1 | 2/2004 | Wickline |
| 2004/0043490 A1 | 3/2004 | Shimada |
| 2004/0049121 A1 | 3/2004 | Yaron |
| 2004/0057931 A1 | 3/2004 | Wilson |
| 2004/0059260 A1 | 3/2004 | Truwit |
| 2004/0136963 A1 | 7/2004 | Wilson |
| 2004/0167391 A1 | 8/2004 | Solar et al. |
| 2004/0171807 A1 | 9/2004 | Gao |
| 2004/0215143 A1 | 10/2004 | Brady |
| 2005/0261218 A1 | 11/2005 | Esau |
| 2005/0288631 A1 | 12/2005 | Lewis |
| 2006/0003451 A1 | 1/2006 | Gao |
| 2006/0058743 A1 | 3/2006 | Putz |
| 2006/0100501 A1 | 5/2006 | Berkelman |
| 2006/0122630 A1 | 6/2006 | Daum |
| 2006/0129126 A1 | 6/2006 | Kaplitt |
| 2006/0142783 A1 | 6/2006 | Lewis |
| 2006/0204479 A1 | 9/2006 | Wilson |
| 2007/0004042 A1 | 1/2007 | Gao |
| 2007/0106305 A1 | 5/2007 | Kao |
| 2008/0008684 A1 | 1/2008 | Wilson |
| 2008/0009784 A1 | 1/2008 | Leedle |
| 2008/0015639 A1 | 1/2008 | Bjork |
| 2008/0050343 A1 | 2/2008 | Wilson |
| 2008/0050345 A1 | 2/2008 | Wilson |
| 2008/0065002 A1 | 3/2008 | Lobl |
| 2008/0065104 A1 | 3/2008 | Larkin |
| 2008/0075737 A1 | 3/2008 | Gao |
| 2008/0103456 A1 | 5/2008 | Johnson |
| 2008/0171930 A1 | 7/2008 | Abolfathi |
| 2008/0249501 A1 | 10/2008 | Yamasaki |
| 2008/0275466 A1 | 11/2008 | Skakoon |
| 2009/0048610 A1 | 2/2009 | Tolkowsky |
| 2009/0112084 A1 | 4/2009 | Piferi et al. |
| 2009/0118610 A1 | 5/2009 | Karmarkar et al. |
| 2009/0215871 A1 | 8/2009 | Wilson |
| 2009/0275107 A1 | 11/2009 | Lock |
| 2009/0317417 A1 | 12/2009 | Vandenberghe |
| 2010/0030219 A1 | 2/2010 | Lerner |
| 2010/0113919 A1 | 5/2010 | Maschke |
| 2010/0162552 A1 | 7/2010 | Solar et al. |
| 2010/0198052 A1 | 8/2010 | Jenkins |
| 2010/0204684 A1 | 8/2010 | Garrison |
| 2010/0217231 A1 | 8/2010 | Ilan |
| 2010/0217236 A1 | 8/2010 | Gill |
| 2010/0222668 A1 | 9/2010 | Dalke |
| 2010/0247490 A1 | 9/2010 | Roy |
| 2010/0278791 A1 | 11/2010 | Wilson |
| 2010/0318061 A1 | 12/2010 | Derrick |
| 2010/0318064 A1 | 12/2010 | Derrick |
| 2010/0331882 A1 | 12/2010 | Bjork |
| 2011/0009879 A1 | 1/2011 | Derrick |
| 2011/0136227 A1 | 6/2011 | Bakker |
| 2011/0171262 A1 | 7/2011 | Bakker |
| 2011/0206616 A1 | 8/2011 | Ichtchenko |
| 2011/0223135 A1 | 9/2011 | Roy |
| 2011/0224478 A1 | 9/2011 | Hannoun-Levi |
| 2011/0229971 A1 | 9/2011 | Knop |
| 2011/0263001 A1 | 10/2011 | Lakshmipathy |
| 2012/0041411 A1 | 2/2012 | Horton |
| 2012/0046349 A1 | 2/2012 | Bell |
| 2012/0058102 A1 | 3/2012 | Wilson |
| 2012/0064115 A1 | 3/2012 | John |
| 2012/0078087 A1 | 3/2012 | Curry |
| 2012/0093853 A1 | 4/2012 | Wilson |
| 2012/0123391 A1 | 5/2012 | Gill |
| 2012/0137379 A1 | 5/2012 | Gao |
| 2012/0203236 A1 | 8/2012 | Mamourian |
| 2012/0209110 A1 | 8/2012 | Bankiewicz |
| 2012/0220648 A1 | 8/2012 | Hwu |
| 2012/0258046 A1 | 10/2012 | Mulzke |
| 2012/0295960 A1 | 11/2012 | Dalfi |
| 2013/0018307 A1 | 1/2013 | Lee |
| 2013/0023033 A1 | 1/2013 | Wilson |

(56) References Cited

U.S. PATENT DOCUMENTS

| | | |
|---|---|---|
| 2013/0045186 A1 | 2/2013 | Gao |
| 2013/0053792 A1 | 2/2013 | Fischell |
| 2013/0066266 A1 | 3/2013 | Cunningham |
| 2013/0096570 A1 | 4/2013 | Solar |
| 2013/0101558 A1 | 4/2013 | Gao |
| 2013/0116721 A1 | 5/2013 | Takagi |
| 2013/0137977 A1 | 5/2013 | Eder |
| 2013/0150701 A1 | 6/2013 | Budar |
| 2013/0158578 A1 | 6/2013 | Ghodke |
| 2013/0195801 A1 | 8/2013 | Gao |
| 2013/0211249 A1 | 8/2013 | Barnett |
| 2013/0211316 A1 | 8/2013 | Wilcox |
| 2013/0211424 A1 | 8/2013 | Thiran |
| 2013/0231683 A1 | 9/2013 | Kao |
| 2013/0267902 A1 | 10/2013 | Seaver |
| 2013/0274778 A1 | 10/2013 | Mercier |
| 2013/0296532 A1 | 11/2013 | Hermens |
| 2013/0317521 A1 | 11/2013 | Choi |
| 2013/0323226 A1 | 12/2013 | Wilson |
| 2013/0323302 A1 | 12/2013 | Constable |
| 2013/0324834 A1 | 12/2013 | Majewski |
| 2014/0024909 A1 | 1/2014 | Vij |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0094823 A1 | 4/2014 | Carcieri |
| 2014/0099666 A1 | 4/2014 | Rossomando |
| 2014/0107186 A1 | 4/2014 | Garcia |
| 2014/0243783 A1 | 8/2014 | Raghavan |
| 2014/0330211 A1 | 11/2014 | Kassab |
| 2014/0336245 A1 | 11/2014 | Mingozzi |
| 2014/0341852 A1 | 11/2014 | Srivastava |
| 2014/0342434 A1 | 11/2014 | Hermens |
| 2015/0005369 A1 | 1/2015 | Muzyczka |
| 2015/0011938 A1 | 1/2015 | Gill |
| 2015/0023924 A1 | 1/2015 | High |
| 2015/0065562 A1 | 3/2015 | Yazicioglu |
| 2015/0080708 A1 | 3/2015 | Piferi |
| 2015/0087961 A1 | 3/2015 | Tyc |
| 2015/0087962 A1 | 3/2015 | Tyc |
| 2015/0100064 A1 | 4/2015 | Skakoon et al. |
| 2015/0118287 A1 | 4/2015 | Hammond |
| 2015/0139952 A1 | 5/2015 | Webster |
| 2015/0159173 A1 | 6/2015 | Vandenberghe |
| 2015/0184197 A1 | 7/2015 | Davidson |
| 2015/0196671 A1 | 7/2015 | Byrne |
| 2015/0230871 A1 | 8/2015 | Sayler et al. |
| 2015/0238610 A1 | 8/2015 | Sista |
| 2015/0307898 A2 | 10/2015 | Hermens |
| 2015/0315610 A1 | 11/2015 | Nishie |
| 2015/0374803 A1 | 12/2015 | Wolfe |
| 2016/0022171 A1 | 1/2016 | Lin |
| 2016/0032319 A1 | 2/2016 | Wright |
| 2016/0051801 A1 | 2/2016 | Vase |
| 2016/0106508 A1 | 4/2016 | Lathrop |
| 2016/0108373 A1 | 4/2016 | Bennett |
| 2016/0153992 A1 | 6/2016 | Buening |
| 2016/0166709 A1 | 6/2016 | Davidson |
| 2016/0199146 A1 | 7/2016 | Tai |
| 2016/0213312 A1 | 7/2016 | Singh |
| 2016/0220789 A1 | 8/2016 | Eldredge |
| 2016/0256534 A1 | 9/2016 | Bankiewicz |
| 2016/0271192 A1 | 9/2016 | Roy |
| 2016/0273058 A1 | 9/2016 | Akashika |
| 2016/0289275 A1 | 10/2016 | Chiorini |
| 2016/0296694 A1 | 10/2016 | Bankiewicz |
| 2016/0317077 A1 | 11/2016 | Sillay |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0339206 A1 | 11/2016 | Cunningham |
| 2016/0340393 A1 | 11/2016 | Schaffer |
| 2016/0340692 A1 | 11/2016 | Wang |
| 2016/0346505 A1 | 12/2016 | Gill |
| 2016/0354163 A1 | 12/2016 | Andrews |
| 2016/0361439 A1 | 12/2016 | Agbandje-McKenna |
| 2016/0369297 A1 | 12/2016 | Byrne |
| 2016/0369298 A1 | 12/2016 | Marsic |
| 2016/0369299 A1 | 12/2016 | Boye |
| 2016/0375151 A1 | 12/2016 | Schaffer |
| 2016/0375221 A1 | 12/2016 | Panotopoulos |
| 2016/0376323 A1 | 12/2016 | Schaffer |
| 2016/0376608 A1 | 12/2016 | Chou |
| 2017/0000904 A1 | 1/2017 | Wilson |
| 2017/0007669 A1 | 1/2017 | Sarkar |
| 2017/0007720 A1 | 1/2017 | Boye |
| 2017/0028082 A1 | 2/2017 | Wilson |
| 2017/0035525 A1 | 2/2017 | Baumgartner |
| 2017/0044504 A1 | 2/2017 | Schaffer |
| 2017/0065835 A1 | 3/2017 | Park |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088858 A1 | 3/2017 | Gao |
| 2017/0096646 A1 | 4/2017 | Roy |
| 2017/0105927 A1 | 4/2017 | Thome |
| 2017/0112946 A1 | 4/2017 | Ikeda |
| 2017/0121734 A1 | 5/2017 | Cairns |
| 2017/0128581 A1 | 5/2017 | Freskgard |
| 2017/0128594 A1 | 5/2017 | Wright |
| 2017/0130208 A1 | 5/2017 | Potter |
| 2017/0130245 A1 | 5/2017 | Kotin |
| 2017/0135778 A1 | 5/2017 | Gill |
| 2017/0145440 A1 | 5/2017 | Hermens |
| 2017/0151348 A1 | 6/2017 | Kaspar |
| 2017/0151416 A1 | 6/2017 | Kutikov |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeil |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0232117 A1 | 8/2017 | Arbetman |
| 2017/0246322 A1 | 8/2017 | Mendell |
| 2017/0258489 A1 | 9/2017 | Galili |
| 2017/0258996 A1 | 9/2017 | Anand |
| 2017/0290637 A1 | 10/2017 | Diez |
| 2017/0333060 A1 | 11/2017 | Panian |
| 2018/0028746 A1 | 2/2018 | Abrams |
| 2018/0098778 A1 | 4/2018 | Ogle |
| 2018/0110568 A1 | 4/2018 | Lenarz |
| 2018/0140810 A1 | 5/2018 | Cataltepe |
| 2018/0193042 A1 | 7/2018 | Wilson |
| 2018/0207399 A1 | 7/2018 | Chou |
| 2018/0303560 A1 | 10/2018 | Pandey |
| 2018/0339065 A1 | 11/2018 | Wilson |
| 2018/0344199 A1 | 12/2018 | Bankiewicz |
| 2018/0361114 A1 | 12/2018 | Chou |
| 2018/0369555 A1 | 12/2018 | Woolley |
| 2019/0000940 A1 | 1/2019 | Kotin |
| 2019/0000991 A1 | 1/2019 | Pykett |
| 2019/0008919 A1 | 1/2019 | Kassab |
| 2019/0008933 A1 | 1/2019 | Kotin |
| 2019/0030281 A1 | 1/2019 | Lim |
| 2019/0038773 A1 | 2/2019 | Esteves |
| 2019/0038777 A1 | 2/2019 | Donsante |
| 2019/0070356 A1 | 3/2019 | Elias |
| 2019/0070387 A1 | 3/2019 | Goyal |
| 2019/0083302 A1 | 3/2019 | Khanna |
| 2019/0083303 A1 | 3/2019 | Khanna |
| 2019/0143099 A1 | 5/2019 | Barker |
| 2019/0160254 A1 | 5/2019 | Anand |
| 2019/0167864 A1 | 6/2019 | Kassab |
| 2019/0167918 A1 | 6/2019 | Fischell |
| 2019/0183517 A1 | 6/2019 | Ogle |
| 2019/0192040 A1 | 6/2019 | Bankiewicz |

(56) References Cited

U.S. PATENT DOCUMENTS

| | | | |
|---|---|---|---|
| 2019/0216575 A1 | 7/2019 | Farah |
| 2019/0223972 A1 | 7/2019 | Fischer |
| 2019/0314110 A1 | 10/2019 | Piferi |
| 2019/0314616 A1 | 10/2019 | Moll |
| 2019/0336232 A1 | 11/2019 | Jenkins |
| 2019/0343552 A1 | 11/2019 | Yaffe |
| 2019/0346516 A1 | 11/2019 | Piferi |
| 2019/0350666 A1 | 11/2019 | Grunert |
| 2019/0351182 A1 | 11/2019 | Chou |
| 2019/0366043 A1 | 12/2019 | Garrison |
| 2020/0016369 A1 | 1/2020 | Garrison |
| 2020/0023160 A1 | 1/2020 | Chou |
| 2020/0046249 A1 | 2/2020 | Randell |
| 2020/0069215 A1 | 3/2020 | Bankiewicz |
| 2020/0078131 A1 | 3/2020 | Karmarkar |
| 2020/0085512 A1 | 3/2020 | Reimer |
| 2020/0086083 A1 | 3/2020 | Porter |
| 2020/0101239 A1 | 4/2020 | Singh |
| 2020/0101275 A1 | 4/2020 | Singh |
| 2020/0147299 A1 | 5/2020 | Piferi |
| 2020/0147344 A1 | 5/2020 | Flores |
| 2020/0164178 A1 | 5/2020 | Garrison |
| 2020/0170539 A1 | 6/2020 | Sayler |
| 2020/0170748 A1 | 6/2020 | Folzenlogen |
| 2020/0214726 A1 | 7/2020 | Anand |
| 2020/0215306 A1 | 7/2020 | Garrison |
| 2020/0222079 A1 | 7/2020 | Swaney |
| 2020/0229889 A1 | 7/2020 | Kells |
| 2020/0246099 A1 | 8/2020 | Jones |
| 2020/0246100 A1 | 8/2020 | Jones |
| 2020/0246101 A1 | 8/2020 | Jones |
| 2020/0269015 A1 | 8/2020 | Fischell |

FOREIGN PATENT DOCUMENTS

| | | | |
|---|---|---|---|
| CA | 2289449 C | 11/1998 |
| CA | 2289837 A1 | 11/1998 |
| CA | 2686281 | 11/1998 |
| CA | 2344641 A1 | 3/2000 |
| CA | 2346613 C | 4/2000 |
| CA | 2343554 A1 | 10/2001 |
| CA | 2282007 C | 5/2002 |
| CA | 2452379 A1 | 1/2003 |
| CA | 2467406 C | 5/2003 |
| CA | 2475855 C | 9/2003 |
| CA | 2872998 | 9/2003 |
| CA | 2974428 | 9/2003 |
| CA | 2499573 A1 | 4/2004 |
| CA | 2510918 A1 | 7/2004 |
| CA | 2511469 A1 | 7/2004 |
| CA | 2511472 | 7/2004 |
| CA | 2575313 | 2/2006 |
| CA | 2576306 | 3/2006 |
| CA | 2581714 | 4/2006 |
| CA | 2619882 | 3/2007 |
| CA | 2621447 | 3/2007 |
| CA | 2623616 | 6/2007 |
| CA | 2642798 | 7/2007 |
| CA | 2644777 | 9/2007 |
| CA | 2672147 | 1/2008 |
| CA | 2660727 | 3/2008 |
| CA | 2666248 | 4/2008 |
| CA | 2674222 | 7/2008 |
| CA | 2687282 | 11/2008 |
| CA | 2688825 | 11/2008 |
| CA | 2695494 | 12/2008 |
| CA | 2700523 | 4/2009 |
| CA | 2700529 | 4/2009 |
| CA | 2700577 | 4/2009 |
| CA | 2700607 | 4/2009 |
| CA | 2701132 | 4/2009 |
| CA | 2701744 | 4/2009 |
| CA | 2704739 | 4/2009 |
| CA | 2721367 | 4/2009 |
| CA | 2704582 | 5/2009 |
| CA | 2726619 | 12/2009 |
| CA | 2739173 | 4/2010 |
| CA | 2771175 | 3/2011 |
| CA | 2796951 | 10/2011 |
| CA | 2802291 | 1/2012 |
| CA | 2774733 | 10/2012 |
| CA | 2838508 | 12/2012 |
| CA | 2860026 | 6/2013 |
| CA | 2864624 | 9/2013 |
| CA | 2878510 | 1/2014 |
| CA | 2879770 | 1/2014 |
| CA | 2883893 | 3/2014 |
| CA | 2884136 | 3/2014 |
| CA | 2895509 | 6/2014 |
| CA | 2844980 | 9/2014 |
| CA | 2915505 | 12/2014 |
| CA | 2920014 | 2/2015 |
| CA | 2920394 | 3/2015 |
| CA | 2921133 | 3/2015 |
| CA | 2937839 | 7/2015 |
| CA | 2966029 | 5/2016 |
| CA | 2983072 | 8/2016 |
| CA | 2987931 | 12/2016 |
| CA | 3008680 | 7/2017 |
| CA | 3016336 | 9/2017 |
| CA | 3035522 | 3/2018 |
| CA | 3070087 | 1/2019 |
| CA | 3078990 | 5/2019 |
| EP | 1015059 | 7/2000 |
| EP | 1015619 | 7/2000 |
| EP | 1018963 | 7/2000 |
| EP | 1046711 | 10/2000 |
| EP | 1078096 | 2/2001 |
| EP | 1121061 | 8/2001 |
| EP | 862388 | 11/2001 |
| EP | 783279 | 12/2001 |
| EP | 1164195 | 12/2001 |
| EP | 1183380 | 3/2002 |
| EP | 1218035 | 7/2002 |
| EP | 1240345 | 9/2002 |
| EP | 1272120 | 1/2003 |
| EP | 1279740 | 1/2003 |
| EP | 1444001 | 8/2004 |
| EP | 1453547 | 9/2004 |
| EP | 1482851 | 12/2004 |
| EP | 1621625 | 2/2006 |
| EP | 1677696 | 7/2006 |
| EP | 1696036 | 8/2006 |
| EP | 1795143 | 6/2007 |
| EP | 1847614 | 10/2007 |
| EP | 1849872 | 10/2007 |
| EP | 1857552 | 11/2007 |
| EP | 1944043 | 7/2008 |
| EP | 2007795 | 12/2008 |
| EP | 2066364 | 6/2009 |
| EP | 2139418 | 1/2010 |
| EP | 2152346 | 2/2010 |
| EP | 2195676 | 6/2010 |
| EP | 2198016 | 6/2010 |
| EP | 2220241 | 8/2010 |
| EP | 2220242 | 8/2010 |
| EP | 2237826 | 10/2010 |
| EP | 2292779 | 3/2011 |
| EP | 2325298 | 5/2011 |
| EP | 2359866 | 8/2011 |
| EP | 2383346 | 11/2011 |
| EP | 2442718 | 4/2012 |
| EP | 2146768 | 8/2012 |
| EP | 2510971 | 10/2012 |
| EP | 2523599 | 11/2012 |
| EP | 2524037 | 11/2012 |
| EP | 2527457 | 11/2012 |
| EP | 2531604 | 12/2012 |
| EP | 2558154 | 2/2013 |
| EP | 2560721 | 2/2013 |
| EP | 2572661 | 3/2013 |
| EP | 2601997 | 6/2013 |
| EP | 2091459 | 9/2013 |
| EP | 2660325 | 11/2013 |

(56) References Cited

FOREIGN PATENT DOCUMENTS

| | | |
|---|---|---|
| EP | 2104530 | 2/2014 |
| EP | 2699270 | 2/2014 |
| EP | 2717955 | 4/2014 |
| EP | 2737071 | 6/2014 |
| EP | 1807009 | 11/2014 |
| EP | 2814958 | 12/2014 |
| EP | 2819739 | 1/2015 |
| EP | 2871239 | 5/2015 |
| EP | 2879719 | 6/2015 |
| EP | 2933336 | 10/2015 |
| EP | 2166974 | 12/2015 |
| EP | 2194906 | 3/2016 |
| EP | 2242531 | 6/2016 |
| EP | 3027259 | 6/2016 |
| EP | 3041566 | 7/2016 |
| EP | 3046500 | 7/2016 |
| EP | 3058959 | 8/2016 |
| EP | 3067417 | 9/2016 |
| EP | 2176283 | 11/2016 |
| EP | 3107610 | 12/2016 |
| EP | 3108000 | 12/2016 |
| EP | 3117005 | 1/2017 |
| EP | 3119310 | 1/2017 |
| EP | 3134431 | 3/2017 |
| EP | 3168298 | 5/2017 |
| EP | 3215191 | 9/2017 |
| EP | 3253437 | 12/2017 |
| EP | 3257547 | 12/2017 |
| EP | 1928557 | 6/2018 |
| JP | S6073547 | 5/1985 |
| JP | H0329665 | 2/1991 |
| JP | H0346305 | 3/1991 |
| JP | H07184929 | 7/1995 |
| JP | H0910315 | 1/1997 |
| JP | 11137568 | 5/1999 |
| JP | 11285533 | 10/1999 |
| JP | 2001293090 | 10/2001 |
| JP | 2001321447 | 11/2001 |
| JP | 2002502276 | 1/2002 |
| JP | 2003275223 | 9/2003 |
| JP | 2005034640 | 2/2005 |
| JP | 2011239987 | 12/2011 |
| JP | 2011255025 | 12/2011 |
| JP | 2013013592 | 7/2013 |
| JP | 2015015988 | 1/2015 |
| JP | 2015015989 | 1/2015 |
| JP | 2015173972 | 10/2015 |
| JP | 2015112360 | 9/2017 |
| JP | 2018153556 | 10/2018 |
| JP | 2019141250 | 12/2018 |
| JP | 2019076411 | 5/2019 |
| WO | WO1993009239 | 5/1993 |
| WO | WO1995034670 | 12/1995 |
| WO | WO1996017947 | 6/1996 |
| WO | WO1996023810 | 8/1996 |
| WO | WO1996030540 | 10/1996 |
| WO | WO1998010088 | 3/1998 |
| WO | WO1998025535 | 6/1998 |
| WO | WO1999027110 | 6/1999 |
| WO | WO1999043360 | 9/1999 |
| WO | WO1999058700 | 11/1999 |
| WO | WO1999061595 | 12/1999 |
| WO | WO2000023116 | 4/2000 |
| WO | WO1999060146 | 5/2000 |
| WO | WO2000024916 | 5/2000 |
| WO | WO2000061017 | 10/2000 |
| WO | WO2000066780 | 11/2000 |
| WO | WO2000075353 | 12/2000 |
| WO | WO2001014539 | 3/2001 |
| WO | WO2001023001 | 4/2001 |
| WO | WO2001025465 | 4/2001 |
| WO | WO2001032711 | 5/2001 |
| WO | WO2001036623 | 5/2001 |
| WO | WO2001042444 | 6/2001 |
| WO | WO2001068888 | 9/2001 |
| WO | WO2001096587 | 12/2001 |
| WO | WO200213714 | 2/2002 |
| WO | WO2002012525 | 2/2002 |
| WO | WO2002014487 | 2/2002 |
| WO | WO2002020748 | 3/2002 |
| WO | WO2002070719 | 9/2002 |
| WO | WO2002071843 | 9/2002 |
| WO | WO2003010320 | 2/2003 |
| WO | WO2003024502 | 3/2003 |
| WO | WO2003042397 | 5/2003 |
| WO | WO2003087382 | 10/2003 |
| WO | WO2003087383 | 10/2003 |
| WO | WO2004044003 | 5/2004 |
| WO | WO2004083441 | 9/2004 |
| WO | WO2004108922 | 12/2004 |
| WO | WO2004111248 | 12/2004 |
| WO | WO2005005610 | 1/2005 |
| WO | WO2005012537 | 2/2005 |
| WO | WO2005111220 | 11/2005 |
| WO | WO2006063247 | 6/2006 |
| WO | WO2006102702 | 9/2006 |
| WO | WO2007064739 | 6/2007 |
| WO | WO2007130519 | 11/2007 |
| WO | WO2007148971 | 12/2007 |
| WO | WO2008133615 | 11/2008 |
| WO | WO2009049823 | 4/2009 |
| WO | WO2009056131 | 5/2009 |
| WO | WO2009125196 | 10/2009 |
| WO | WO2009134681 | 11/2009 |
| WO | WO2011038187 | 3/2011 |
| WO | WO2011054976 | 5/2011 |
| WO | WO2011087495 | 7/2011 |
| WO | WO2011108568 | 9/2011 |
| WO | WO2011122950 | 10/2011 |
| WO | WO 2010109053 | 11/2011 |
| WO | WO2011156701 | 12/2011 |
| WO | WO2012007458 | 1/2012 |
| WO | WO2012057363 | 5/2012 |
| WO | WO2012109570 | 8/2012 |
| WO | WO2012114090 | 8/2012 |
| WO | WO2012144446 | 10/2012 |
| WO | WO2013078199 | 5/2013 |
| WO | WO2013164793 | 11/2013 |
| WO | WO2013170078 | 11/2013 |
| WO | WO2014128875 | 8/2014 |
| WO | WO2014128881 | 8/2014 |
| WO | WO2014160092 | 10/2014 |
| WO | WO2014168953 | 10/2014 |
| WO | WO 2014170470 | 10/2014 |
| WO | WO2014170480 | 10/2014 |
| WO | WO2014172669 | 10/2014 |
| WO | WO2014186579 | 11/2014 |
| WO | WO2014189253 | 11/2014 |
| WO | WO2014194132 | 12/2014 |
| WO | WO2014201252 | 12/2014 |
| WO | WO2015012924 | 1/2015 |
| WO | WO2015013148 | 1/2015 |
| WO | WO2015018503 | 2/2015 |
| WO | WO2014186746 | 3/2015 |
| WO | WO2015031686 | 3/2015 |
| WO | WO2015044292 | 4/2015 |
| WO | WO2015049886 | 4/2015 |
| WO | WO2015057807 | 4/2015 |
| WO | WO2015060722 | 4/2015 |
| WO | WO2015093274 | 6/2015 |
| WO | WO2015108610 | 7/2015 |
| WO | WO2015114365 | 8/2015 |
| WO | WO2015121501 | 8/2015 |
| WO | WO2015124546 | 8/2015 |
| WO | WO2015127128 | 8/2015 |
| WO | WO2015137802 | 9/2015 |
| WO | WO2015196179 | 12/2015 |
| WO | WO2016019364 | 2/2016 |
| WO | WO2016054554 | 4/2016 |
| WO | WO2016054557 | 4/2016 |
| WO | WO2016065001 | 4/2016 |
| WO | WO2016073693 | 5/2016 |
| WO | WO2016081811 | 5/2016 |
| WO | WO2016081927 | 5/2016 |

(56) References Cited

FOREIGN PATENT DOCUMENTS

| WO | WO2016115382 | 7/2016 |
|---|---|---|
| WO | WO2016122791 | 8/2016 |
| WO | WO2016126857 | 8/2016 |
| WO | WO2016130591 | 8/2016 |
| WO | WO2016137949 | 9/2016 |
| WO | WO2016154055 | 9/2016 |
| WO | WO2016154344 | 9/2016 |
| WO | WO 2016164609 | 10/2016 |
| WO | WO2016168728 | 10/2016 |
| WO | WO2016172008 | 10/2016 |
| WO | WO2016172155 | 10/2016 |
| WO | WO2016179496 | 11/2016 |
| WO | WO2016183297 | 11/2016 |
| WO | WO2016191418 | 12/2016 |
| WO | WO2016196507 | 12/2016 |
| WO | WO2017004514 | 1/2017 |
| WO | WO2017005806 | 1/2017 |
| WO | WO2017015102 | 1/2017 |
| WO | WO2017019876 | 2/2017 |
| WO | WO2017019994 | 2/2017 |
| WO | WO2017023724 | 2/2017 |
| WO | WO2017058892 | 4/2017 |
| WO | WO2017070476 | 4/2017 |
| WO | WO2017070516 | 4/2017 |
| WO | WO2017070525 | 4/2017 |
| WO | WO2017070678 | 4/2017 |
| WO | WO2017075335 | 5/2017 |
| WO | WO2017075338 | 5/2017 |
| WO | WO2017083423 | 5/2017 |
| WO | WO2017093330 | 6/2017 |
| WO | WO2017096039 | 6/2017 |
| WO | WO2017100671 | 6/2017 |
| WO | WO2017100674 | 6/2017 |
| WO | WO2017100676 | 6/2017 |
| WO | WO2017100704 | 6/2017 |
| WO | WO2017136202 | 8/2017 |
| WO | WO2017136536 | 8/2017 |
| WO | WO2017192699 | 11/2017 |
| WO | WO2018044933 | 3/2018 |
| WO | WO2018191450 | 10/2018 |
| WO | WO2019157070 | 8/2019 |
| WO | WO2020010035 | 1/2020 |
| WO | WO2020064660 | 4/2020 |

OTHER PUBLICATIONS

Adamson-Small et al. (2017) "Sodium chloride enhances rAAV production in a serum-free suspension manufacturing platform using the Herpes Simplex Virus System" Human Gene Therapy Methods, 28:1 1-14.

Afione et al. (2015) "Identification and Mutagenesis of the Adeno-Associated Virus 5 Sialic Acid Binding Region" Journal of Virology, 89:3 1660-1672.

Ahmed et al. (2016) "rAAV gene therapy in a Canavan's disease mouse model reveals immune impairments and an extended pathology beyond the central nervous system" Molecular Therapy, 24:6 1030-1041.

Ai et al. (2017) "Adeno-associated virus serotype rh.10 displays strong muscle tropism following intraperitoneal delivery" Science Report, 7:40336.

Ai et al. (2017) "A Scalable and Accurate Method for Quantifying Vector Genomes of Recombinant Adeno-Associated Viruses in Crude Lysate" Human Gene Therapy Methods, 28:3 139-147.

Alton et al. (2015) "Repeated nebulisation of non-viral CFTR gene therapy in patients with cystic fibrosis: a randomised, double-blind, placebo-controlled, phase 2b trial" The Lancet Respiratory Medicine, 3:9 684-691.

Altschul et al. (1990) "Basic local alignment search tool" Journal of Molecular Biology, 215:3 403-410.

Alves et al. (2016) "Ultramicroscopy as a Novel Tool to Unravel the Tropism of AAV Gene Therapy Vectors in the Brain" Science Reports, 6:28272.

Aoyama et al. (2015) "Wnt11 gene therapy with adeno-associated virus 9 improves the survival of mice with myocarditis induced by coxsackievirus B3 through the suppression of the inflammatory reaction." Journal Molecular Cell Cardiology 84 45-51.

Arrigo et al. (2017) "Visual System Involvement in Patients with Newly Diagnosed Parkinson Disease" Radiology, 161732.

Aubourg (2016) "Gene therapy for rare central nervous system diseases comes to age" Endocrine Development, 30: 141-146.

Aydemir et al. (2016) Mutants at the 2-fold interface of AAV2 structural proteins suggest a role in viral transcription for AAV capsids. Journal of Virology 90:16 7196-7204.

Bankiewicz et al. (2016) "AAV Viral Vector Delivery to the Brain by Shape-conforming MR-guided Infusions" Journal Control Release, 240 434-442.

Bankiewicz et al. (2000) "Convection-enhanced delivery of AAV vector in Parkinsonian monkeys; in vivo detection of gene expression and restoration of dopaminergic function using pro-drug approach" Experimental Neurology, 164: 2-14.

Bankiewicz et al. (2006) "Long-term clinical improvement in MPTP-lesioned primates after gene therapy with AAV-hAADC" Molecular Therapy, 14:4 564-570.

Bantel-Schaal et al. (1999) "Human adeno-associated virus type 5 is only distantly related to other known primate helper-dependent parvoviruses" Journal of Virology, 73:2 939-947.

Bartus et al. (2013) "Safety/feasibility of targeting the substantia nigra with AAV2-neurturin in Parkinson patients" Neurology, 80:18 1698-1701.

Baum et al. (2015) "Advances in salivary gland gene therapy—oral and systemic implications" Expert Opinion on Biological Therapy, 15:10 1443-1454.

Baum et al. (2012) "Early responses to adenoviral-mediated transfer of the aquaporin-1 cDNA for radiation-induced salivary hypofunction" Proceedings of the National Academy of Sciences of the United States of America, 109:47 19403-19407.

Bell et al. (2016) "Effects of self-complementarity, codon optimization, transgene, and dose on liver transduction with AAV8" Human Gene Therapy Methods, 27:6 228-237.

Berge (1977) "Pharmaceutical salts" Journal of Pharmaceutical Sciences, 66:1 1-19.

Berry et al. (2016) "Cellular transduction mechanisms of adeno-associated viral vectors" Current Opinion in Virology, 21 54-60.

Bey et al. (2017) "Efficient CNS targeting in adult mice by intrathecal infusion of single-stranded AA V9-GFP for gene Therapy of neurological disorders" Gene Therapy, 24:5 325-332.

Blits et al. (2017) "Perspective on the Road toward Gene Therapy for Parkinson's Disease" Frontiers in Neuroanatomy, 10:128.

Bobo et al. (1994) "Convection-enhanced delivery of macromolecules in the brain" Proceedings of the National Academy of Sciences of the United States of America, 91:6 2076-2080.

Brulet et al. (2017) "NEUROD1 Instructs Neuronal Conversion in Non-Reactive Astrocytes" Stem Cell Reports 8:6 1506-1515.

Buclez et al. (2016) "Rapid, scalable, and low-cost purification of recombinant adeno-associated virus produced by baculovirus expression vector system" Molecular Therapy Methods Clinical Development, 3:16035.

Burnham et al. (2015) Analytical ultracentrifugation as an approach to characterize recombinant adeno-associated viral vectors: Human Gene Therapy Methods, 26:6 228-242.

Cabral-Miranda et al. (2017) "rAAV8-733-Mediated Gene Transfer of CHIP/Stub-1 Prevents Hippocampal Neuronal Death in Experimental Brain ischemia" Molecular Therapy, 25:2 392-400.

Carter (2004) "Adeno-associated virus and the development of adeno-associated virus vectors: a historical perspective" Molecular Therapy, 10:6 981-989.

Carillo et al. (1988) "The Multiple Sequence Alignment Problem in Biology" SIAM Journal on Applied Mathematics, 48:55 1073-1082.

Chandler et al. (2017) "rAAV integration and genotoxicity: insights from animal models" Human Gene Therapy, 28:4 314-322.

Chandler RJ, et al. (2017) "Systemic AAV9 gene therapy improves the lifespan of mice with Niemann-Pick disease, type C1" Human Molecular Genetics, 26:1 52-64.

(56) References Cited

OTHER PUBLICATIONS

Chiorini et al. (1999) "Adeno-associated virus (AAV) type 5 Rep protein cleaves a unique terminal resolution site compared with other AAV serotypes" Journal of Virology 73:5 4293-4298.
Chiorini JA, et al. (1997) 'Cloning of adeno-associated virus type 4 (AAV4) and generation of recombinant AAV4 particles Journal of Virology 71:9 6823-6833.
Chiorini et al. (1999) "Cloning and characterization of adeno-associated virus type 5" Journal of Virology, 73:2 1309-1319.
Christine et al. (2019) "MRI-guided Phase 1 Trial of Putaminal AADC Gene Therapy for Parkinson's Disease" Annals of Neurology, 85:5 11 pages.
Christine al. (2009) "Safety and tolerability of putaminal MDC gene therapy for Parkinson disease" Neurology 73: 1662-1669.
Clement et al. (2016) "Manufacturing of recombinant adeno-associated viral vectors for clinical trials" Molecular Therapy—Methods & Clinical Development, 3:16002.
Conner et al. (2019) "Intraspinal and Intracortical Delivery of AAV Vectors for Intersectional Circuit Tracing in Nontransgenic Species" Methods in Molecular Biology, 1950: 165-176.
Dang et al. (2017) "In vivo dynamics of AA V-mediated gene delivery to sensory neurons of the trigeminal ganglia" Scientific Reports, 7:927 1-13.
Dashkoff et al. (2016) "Tailored transgene expression to specific cell types in the central nervous system after peripheral injection with AAV9" Molecular Therapy Methods Clinical Development, 3:16081.
D'Costa et al. (2016) "Practical utilization of recombinant AAV vector reference standards: focus on vector genome titration by free ITR qPCR" Molecular Therapy Methods Clinical Development, 5:16019.
De Leeuw et al. (2016) "rAAV-compatible MiniPromoters for Restricted Expression in the Brain and Eye" Molecular Brain, 9:1 52.
Deng et al. (2016) "Replication of an autonomous human parvovirus in non-dividing human airway epithelium is facilitated through the DNA damage and repair pathways" PLOS Pathogens, 12:1 e1005399.
Devereux et al. (1984) "A comprehensive set of sequence analysis programs for the VAX" Nucleic Acids Research, 12:1 Pt 1 387-395.
Dimidschstein et al. (2016) "A viral strategy for targeting and manipulating interneurons across vertebrate species" Nature Neuroscience 19:12 1743-1749.
Ding et al. (2002) "Biochemical Characterization of Junonia Coenia Densovirus Nonstructural Protein NS-1" Journal of Virology, 76:1 338-345.
Donsante et al. (2016) "Intracerebroventricular delivery of self-complementary adeno-associated virus serotype 9 to the adult rat brain" Gene Therapy, 23:5 401-407.
Drouin et al. (2016) "Cryo-electron microscopy reconstruction and stability studies of Wild-Type and R432A Variant of AAV2 Reveals Capsid Structural Stability is a Major Factor in Genome Packaging" Journal of Virology, 90:19 8542-8551.
Earley et al. (2017) "Adeno-Associated Virus Assembly-Activating Protein Is Not an Essential Requirement for Capsid Assembly of AAV Serotypes 4, 5 and 11" Journal of Virology 91:3 pii:e0198-16.
El-Shamayleh et al. (2016) "Strategies for targeting primate neural circuits with viral vectors" Journal of Neurophysiology, 116:1 122-134.
Emborg, et al., (2010) "Intraoperative Intracerebral MRI-Guided Navigation for Accurate Targeting in Nonhuman Primates", Cell Transplant., 19(12), pp. 1587-1597.
Espay et al. (2017) "Optimizing extended-release carbidopa/levodopa in Parkinson disease" Neurology: Clinical Practice, 7:86-93.
Fargnoli et al. (2016) "Liquid jet delivery method featuring S100A1 gene therapy in the rodent model following acute myocardial infarction" Gene Therapy, 23:2 151-157.
Forsayeth et al. (2006) "A Dose-Ranging Study of AAV-hAADC Therapy in Parkinsonian Monkeys" Molecular Therapy, 14:4 571-577.

Foust et al. (2009) "Intravascular AAV9 preferentially targets neonatal neurons and adult astrocytes" Nature Biotechnology, 27:1 59-65.
Gessler et al. (2016) "Gene Therapy for the Treatment of Neurological Disorders: Metabolic Disorders" Methods in Molecular Biology, 1382 429-465.
Gilkes et al. (2015) "Preferred Transduction with AAV8 and AAV9 Via Thalamic Administration in the MPS IIIB Model: A Comparison of Four rAAV Serotypes" Molecular Genetics and Metabolism Reports, 7:6 48-54.
Gombash et al. (2016) "Systemic Gene Therapy for Targeting the CNS" Methods in Molecular Biology 1382 231-237.
Greig et al. (2016) "Impact of intravenous infusion time on AAV8 vector pharmacokinetics, safety, and liver transduction in cynomolgus macaques" Molecular Therapy—Methods & Clinical Development, 3:16079.
Greig et al. (2016) "Intramuscular administration of AAV overcomes pre-existing neutralizing antibodies in rhesus macaques" Vaccine, 34:50 6323-6329.
Gribskov et al. (1991) "Sequence Analysis Primer" M Stockton Press, New York.
Grieger et al. (2016) "Production of Recombinant Adeno-associated Virus Vectors Using Suspension HEK293 Cells and Continuous Harvest of Vector From the Culture Media for GMP FIX and FLT1 Clinical Vector" Molecular Therapy, 24:2 287-297.
Griffin (1994) "Computer Analysis of Sequence Data" Part 1, Humana Press.
Grimm et al. (1999) "Progress in adeno-associated virus type 2 vector production: promises and prospects for clinical use" Human Gene Therapy 10:15 2445-2450.
Grimson et al. (2007) "MicroRNA targeting specificity in mammals: determinants beyond seed pairing" Molecular Cell 5:27(1) 91-105.
Gruntman et al. (2015) "Delivery of Adeno-associated virus gene therapy by intravascular limb infusion methods" Molecular Therapy—Methods & Clinical Development, 26:3 159-64.
Gruntman et al. (2017) "Retro-Orbital Venous Sinus Delivery of rAAV9 Mediates High-Level Transduction of Brain and Retina Compared with Temporal Vein Delivery in Neonatal Mouse Pups" Human Gene Therapy, 28:3 228-230.
Gruntman et al. (2015) "Stability and Compatibility of Recombinant Meno-Associated Virus Under Conditions Commonly Encountered in Human Gene Therapy Trials" Human Gene Therapy Methods 26:2 71-76.
Gurda et al. (2016) "Evaluation of AA V-mediated gene therapy for central nervous system disease in canine mucopolysaccharidosis VII" Molecular Therapy, 24:2 206-216.
Hai et al. (2009) "Long-term transduction of miniature pig parotid glands using serotype 2 adeno-associated viral vectors" The Journal of Gene Medicine, 11:6 506-514.
Hagg et al. (2016) "Using AA V vectors expressing the beta 2-adrenoceptor or associated G alpha proteins to modulate skeletal muscle mass and muscle fiber size" Scientific Reports, 6:23042.
Hastie et al. (2015) "Adeno-Associated Virus at 50: A Golden Anniversary of Discovery, Research, and Gene Therapy Success—A Personal Perspective" Human Gene Therapy 26:5 257-265.
Hastie et al. (2015) "Recombinant adeno-associated virus vectors in the treatment of rare diseases" Expert Opinion Orphan Drugs, 3:6 675-689.
Heim et al. (1996) "Engineering green fluorescent protein for improved brightness, longer wavelengths and fluorescence resonance energy transfer" Current Biology 6:2 178-182.
Heim (1995) "Improved green fluorescence" Nature 373 663-664.
Heim et al. (1994) "Wavelength mutations and posttranslational autoxidation of green fluorescent protein" Proceedings of the National Academy of Sciences of the United States of America.
Heller et al. (2015) "Human alpha 7 integrin gene (ITGA7) delivered by adeno-associated virus extends survival of severely affected dystrophin/utrophin deficient mice" Human Gene Therapy, 26:10 647-656.
Hinderer et al. (2016) "Delivery of an Adeno-Associated Virus Vector into CSF Attenuates Central Nervous System Disease in Mucopolysaccharidosis Type II Mice" Human Gene Therapy 27:11.

(56) References Cited

OTHER PUBLICATIONS

Hinderer et al. (2015) "Neonatal Systemic AAV Induces Tolerance to CNS Gene Therapy in MPS I Dogs and Nonhuman Primates" Molecular Therapy, 23:8 1298-1307.
Hirsch et al. (2016) "Delivering Transgenic DNA Exceeding the Carrying Capacity of AAV Vectors" Methods Molecular Biology, 1382: 21-39.
Hocquemiller et al. (2016) "Adeno-Associated Virus-Based Gene Therapy for CNS Diseases" Human Gene Therapy, 27:7 478-496.
Hordeaux et al. (2015) "Efficient central nervous system AAVrh10-medialed intrathecal gene transfers in adult and neonate rats" Gene Therapy 22:4 316-324.
Huang et al. (2016) "Characterization of the Meno-Associated Virus 1 and 6 Sialic Acid Binding Site" Journal of Virology, 90:11 5219-5230.
Hudry et al. (2016) "Exosome-associated AAV vector as a robust and convenient neuroscience tool" Gene Therapy, 23:4 380-392.
Ibrahim et al. (2016) "Stable liver specific expression of human IDOL in humanized mice raises plasma cholesterol" Cardiovascular Research, 110:1 23-29.
Jackson et al. (2016) "Better Targeting, Better Efficiency for Wide-Scale Neuronal Transduction with the Synapsin Promoter and AAV-PHP.B" Frontiers in Molecular Neuroscience, 6:116.
Jeong et al. (2016) "Matricellular Protein CCN5 Reverses Established Cardiac Fibrosis" Journal of the American College of Cardiology, 67:13 1556-1568.
Jolesz (2011) "Intraoperative Imaging in Neurosurgery: Where Will the Future Take Us?" Acta Neurochirurgica Supplement, 109 21-25.
Kailasan et al. (2015) "Parvovirus Family Conundrum: What makes a killer?" Annual Review of Virology, 2:1 425-450.
Kailasan et al. (2015) "Structure of an Enteric Pathogen, Bovine Parvovirus" Journal of Virology, 89:5 2603-2614.
Kajigaya et al. (1991) "Self-assembled B19 parvovirus capsids, produced in a baculovirus system, are antigenically and immunogenically similar to native virions" Proceedings of the National Academy of Sciences of the United States of America, 88:11 4646-4650.
Katz et al. (2015) "AAV gene transfer delays disease onset in a TPP1-deficient canine model of the late infantile form of Batten Disease" Science Translational Medicine, 7:313 ra180.
Katz et al. (2018) "Standardized method for intra-cisterna magna delivery under fluoroscopic guidance in nonhuman primates" Human Gene Therapy Methods, (5): 212-219.
Kells et al. (2009) "Efficient gene therapy-based method for the delivery of therapeutics to primate cortex" Proceedings of the National Academy of Sciences of the United States of America, 106:7 2407-2411.
Kirnbauer et al. (1996) "Virus-like particles of bovine papillomavirus type 4 in prophylactic and therapeutic immunization" Virology, 219:1 37-44.
Knezevic et al. (2016) "Adeno-associated Virus Serotype 9—Driven Expression of BAG3 Improves Left Ventricular Function in Murine Hearts with Left Ventricular Dysfunction Secondary to a Myocardial Infarction" JACC: Basic to Translational Science, 1:7 647-656.
Kohlbrenner et al. (2017) "Production and Characterization of Vectors Based on the Cardiotropic AAV Serotype 9" Methods in Molecular Biology, 1521 91-107.
Kothari et al. (2015) "Iodine-124 Labeled Adeno-Associated Virus: A Promising Tool for Tracking Gene Therapy" Journal of Nuclear Medicine, 56:supplement 3 494.
Kothari et al. (2017) "Radioiodinated Capsids Facilitate In Vivo Non-Invasive Tracking of Adeno-Associated Gene Transfer Vectors" Scientific Reports, 7:39594.
Kotin et al. (2011) "Large-scale recombinant adeno-associated virus production" Human Molecular, Genetics 20:R1 R2-6.
Kotin RM, et al. (2017) "Manufacturing clinical grade recombinant adeno-associated virus using invertebrate cell lines" Human Gene Therapy.
Kotterman et al. (2015) "Enhanced cellular secretion of AAV2 by expression of foreign viral envelope proteins" Biochemical Engineering Journal, vol. 93: 108-114.

Kozak (1996) "Interpreting cDNA sequences: some insights from studies on translation" Mammalian Genomics, 8: 563-574.
Kozak (1986) "Point mutations define a sequence flanking the AUG initiator codon that modulates translation by eukaryotic ribosomes" Cell, 44:2 283-292.
Kozak (1989) "The scanning model for translation: an update" Journal Cell Biology, 108:2 229-241.
Krauze et al. (2005) "Reflux-free cannula for convection-enhanced high-speed delivery of therapeutic agents" Journal of Neurosurgery, 103:5 923-929.
Landegger et al. (2017) "A synthetic AAV vector enables safe and efficient gene transfer to the mammalian inner ear" National Biotechnology, 35:3 280-284.
Larson et al. (2012) "An Optimized System for Interventional MRI Guided Stereotactic Surgery: Preliminary Evaluation of Targeting Accuracy" Neurosurgery, 70(Operative): ons95-ons103, pp. 1-18.
Lentz et al. (2015) "Insight into the Mechanism of Inhibition of Meno-Associated Virus by the Mre11/Rad50/Nbs1 Complex" Journal of Virology, 89:1 181-194.
Li et al. (2015) "Efficient and targeted transduction of nonhuman primate liver with systemically delivered optimized AAV3B vectors" Molecular Therapy, 23:12 1867-1876.
Li et al. (2013) "Production and characterization of novel recombinant adeno-associated virus replicative-form genomes: a eukaryotic source of DNA for gene transfer" PLOS One, 8:8.
Ling et al. (2016) "Strategies to generate high-titer, high-potency recombinant AAV3 serotype vectors" Molecular Therapy Methods Clinical Development, 3:16029.
Lu et al. (2017) "A 5'non-coding exon containing engineered intron enhances transgene expression from recombinant AAV vectors in vivo" Human Gene Therapy, 28:1 125-134.
Lukashcuk et al. (2016) "AAV9-mediated central nervous system-targeted gene delivery via cisterna magna route in mice" Molecular Therapy Methods Clinical Development, 3:15055.
Medtronic, Cranial Solutions: A Brain Biopsy Solution Built Around Your Surgical Workflow. www.medtronicneurosurgery.com. 2013.
Maniatis et al. (1982) "Molecular Cloning" CSH Laboratory.
Martin et al. (2008) "Minimally Invasive Precision Brain Access Using Prospective Stereotaxy and a Trajectory Guide", Journal of Magnetic Resonance Imaging 27:737-743.
Mason et al. (2017) "Delivery and evaluation of recombinant adeno-associated viral vectors in the equine distal extremity or the treatment of laminitis" Equine Veterinary Education 49:1 79-86.
McClements et al. (2016) "A fragmented adeno-associated viral dual vector strategy for treatment of diseases caused by mutations in large genes leads to expression of hybrid transcripts" Journal of Genetic Syndromes & Gene Therapy, 7:5 311.
Mendell Jr, et al. Follistatin Gene Therapy for Sporadic Inclusion Body Myositis Improves Functional Outcomes Molecular Therapy, 25:4 870-879.
Merten et al. (2016) "Viral vectors for gene therapy and gene modification approaches" Biochemical Engineering Journal.
Merkel et al. (2016) "Trafficking of AAV Vectors Across a Model of the Blood-Brain Barrier; a Comparative Study of Transcytosis and Transduction Using Primary Human Brain Endothelial Cells" Journal Neurochemistry, 140:2 216-230.
Mietzsch et al. (2017) "OneBac 2.0: Sf9 Cell Lines for Production of AAV1, AAV2 and AAVB Vectors with Minimal encapsidation of Foreign DNA" Human Gene Therapy Methods, 28:1 15-22.
Mietzsch et al. (2015) "OneBac 2.0: Sf9 cell lines for production of AAV5 vectors with enhanced infectivity and minimal encapsidation of foreign DNA" Human Gene Therapy, 10 688-697.
Miyanohara et al. (2016) "Potent Spinal Parenchymal AAV9-medialed Gene Delivery by Subpial Injection in Adult Rats and Pigs" Molecular Therapy Methods Clinical Development, 3: 16046.
Murlidharan et al. (2016) "Glymphatic Fluid Transport Controls Paravascular Clearance of AAV Vectors from the Brain" JCI Insight, 1:14.
Muralidharan et al. (2015) "Unique glycan signatures regulate adeno-associated virus tropism in the developing brain" Journal of Virology 89:7 3976-3987.
Muzyczka et al. (2015) "AAV's Golden Jubilee" Molecular Therapy 23:5 807-808.

(56) References Cited

OTHER PUBLICATIONS

Myers et al. (1988) "Optimal alignments in linear space" Computer Applications in the Biosciences, 4:1 11-17.
Naidoo et al. "Extensive Transduction and Enhanced Spread of a Modified AAV2 Capsid in the Non-human Primate CNS" Molecular Therapy, 26:10 2418-2430.
Nambiar et al. (2017) "Characteristics of minimally oversized adeno-associated virus vectors encoding human Factor VIII generated using producer cell lines and triple transfection" Human Gene Therapy Methods, 28:1 23-38.
Nery et al. (2015) "New methods for investigation of neuronal migration in embryonic brain explants" Journal of Neuroscience Methods 239:80-84.
Neuberger EWI et al. (2016) "Establishment of two quantitative nested qPCR assays targeting the human EPO transgene" Gene Therapy 23:4 330-339.
Nicolson et al. (2016) "Identification and validation of small molecules that enhance recombinant Adeno-associated virus transduction following high throughput screen" Journal of Virology 90:16 7019-7031.
Noroozian et al. (2019) "MRI-Guided Focused Ultrasound for Targeted Delivery of rAAV to the Brain" Methods in Molecular Biology, 1950 177-197.
Nygaard et al. (2016) "A universal system to select gene-modified hepatocytes in vivo" Science Translational Medicine, 8:342.
Ojala et al. (2015) "Adeno-associated virus vectors and neurological gene therapy" Neuroscientist, 21:1 84-98.
Oliva et al. (1997) "An automated classification of the structure of protein loops" The Journal Molecular Biology, 266:4 814-830.
O'Reilly et al. (1994) "Baculovirus expression vectors: a laboratory manual" Science, 347 pages.
Pacouret et al. (2017) "AAV-ID: A Rapid and Robust Assay for Batch-to-Batch Consistency Evaluation of AAV Preparations" Molecular Therapy, 25:6 1375-1386.
Parr et al. (1997) "Tumor-selective transgene expression in vivo mediated by an E2F-responsive adenoviral vector" Nature Medicine, 3:10 1145-1149.
Penaud-Budloo et al. (2017) Accurate identification and quantification of DNA species by next-generation sequencing in adeno-associated viral vectors produced in insect cells. Hum Gene Therapy Methods, 28:3 148-162.
Petit et al. (2017) "Rod Outer Segment Development Influences AAV-Mediated Photoreceptor Transduction After Subretinal Injection" Human Gene Therapy 28:6 464-481.
Philiport et al. (1995) "Liposomes as tools in Basic Research and Industry" CRC Press, 68 pages.
Pierson et al. (2016) "Resolving adeno-associated viral particle diversity with charge detection mass spectrometry" Analytical Chemistry, 88:13 6718-6725.
Pillay et al. (2016) "An essential receptor for adeno-associated virus infection" Nature, 539:7629 456.
Platt et al. (2013) "Embryonic disruption of the candidate dyslexia susceptibility gene homolog Kiaa0319-like results in neuronal migration disorders" Neuroscience, 248:585-593.
Ponder et al. (2014) "Intrathecal injection of lentiviral vector results in high expression in the brain of 30 mucopolysaccharidosis VII dogs but the pattern of expression is different than for AAV9 or AAV-rh10" Journal of Controlled Release 196:71-78.
Poon et al. (2011) "Distribution of Kiaa0319-like immunoreactivity in the adult mouse brain—a novel protein encoded by the putative dyslexia susceptibility gene KIAA0319-like" Histology & Histopathology, 8: 953-963.
Poon et al. (2011) "Dyslexia-associated kiaa0319-like protein interacts with axon guidance receptor nogo receptor 1" Cellular and Molecular Neurobiology, 1: 27-35.
Potts et al. (2013) "Devices for cell transplantation into the central nervous system: Design considerations and emerging technologies" Surg Neurol Int 4(1): S22-S30.
Powell et al. (2015) "Viral expression cassette elements to enhance transgene target specificity and expression in gene therapy" Discovery Medical, 19:102 49-57.
Rashnonejad et al. (2016) "Large-Scale Production of Adeno-Associated Viral Vector Serotype-9 Carrying the Human Survival Motor Neuron Gene" Molecular Biotechnology, 58:1 30-36.
Reid et al. (2017) "miRNA mediated post-transcriptional silencing of transgenes leads to increased adeno-associated viral vector yield and targeting specificity" Gene Therapy, 24:8 462-469.
Ren et al. (2015) "Adeno-associated virus-mediated BMP-7 and SOX9 in vitro co-transfection of human degenerative intervertebral disc cells" Genetics and Molecular Research, 14:2 3736-3744.
Richard (1995) "Methods in Molecular Biology", ed. Humana Press.
Richardson et al. (2011) "Novel platform for MRI-guided convection enhanced delivery of therapeutics: preclinical validation in nonhuman primate brain" Stereotactic and Functional Neurosurgery, 89: 141-151.
Richardson et al. (2011) "Interventional MRI-guided putaminal delivery of AAV2-GDNF for a planned clinical trial in Parkinson's disease" Molecular Therapy, 19:6 1048-1057.
Rosario et al. (2016) "Microglia-specific Targeting by Novel Capsid-modified AAV6 Vectors" Molecular Therapy Methods Clinical Development, 3:16026.
Ruffing et al. (1992) "Assembly of virus like particles by recombinant structural proteins of adeno-associated virus type 2 in insect cells" Journal of Virology 66:12 6922-6930.
Rutledge et al. (1998) "Infections clones and vectors derived from adeno-associated virus (AAV) serotypes other than AAV type 2" Journal of Virology 72:1 309-319.
Saito et al. "Gadolinium-loaded liposomes allow for real-time magnetic resonance imaging of convection-enhanced delivery in the primate brain" Experimental Neurology, 196:2 381-9.
Salegio, et al., (2016)"MRI-Guided Delivery of Viral Vectors", Gene Therapy for Neurological Disorders: Methods and Protocols, Methods in Molecular Biology, vol. 1382.
Samaranch et al. (201) "Cerebellomedullary Cistern Delivery for AAV-Based Gene Therapy: A Technical Note for Nonhuman Primates" Human Gene Therapy Methods, 27:1 13-16.
Samaranch et al. (2017) "MR-guided parenchymal delivery of adeno-associated viral vector serotype 5 in non-human primate brain" Gene Therapy 24:4 253-261.
Samulski et al. (1989) "Helper-free stocks of recombinant adeno-associated viruses: normal integration does not require viral gene expression" Journal of Virology, 63:9 3822-3828.
Saraiva et al. (2016) "Gene Therapy for the CNS Using AAVs: The Impact of Systemic Delivery by AAV9" Journal of Controlled Release, 10:241 94-109.
Sawada et al. (2016) "Inflammation-induced Reversible Switch of the Neuron-specific Enolase Promoter from Purkinje Neurons to Bergmann Glia" Science Reports, 13:6 27758.
Schnepp et al. (2016) "Recombinant adeno-associated virus vector genomes take the form of long-lived transcriptionally competent episomes in human muscle" Human Gene Therapy, 2:1 32-42.
Sebastian et al. (2012) "Safety and tolerability of magnetic resonance imaging-guided convection-enhanced delivery of AAV2-hAADC with a novel delivery platform in nonbuman primate striatum" Human Gene Therapy, 23:2 210-217.
Sebastian et al. (2014) "Safety and tolerability of MRI-guided infusion of AAV2-hAADC into the mid-brain of nonhuman primate" Molecular Therapy Methods Clinical Development, 3: 14049.
Shen et al. (2016) "Analysis of the Cis and Trans Requirements for DNA Replication at the Right End Hairpin of the Human Bocavirus 1 Genome" Journal of Virology, 90:17 7761-7777.
Shen et al. (2015) "Inhibition of pathological brain angiogenesis through systemic delivery of AAV vector expressing soluble FLT1" Gene Therapy, 2:11 893-900.
Singh et al. (2016) "Therapeutic Value of Adeno Associated Virus as a Gene Therapy Vector for Parkinson's Disease—A Focused Review" Current Gene Therapy, 16:4 278-286.
Siu et al. (2017) "Improved gene delivery to adult mouse spinal cord through the use of engineered hybrid adeno-associated viral serotypes" Gene Therapy, 24:6 361-369.

(56) References Cited

OTHER PUBLICATIONS

Sondhi et al. (2017) "Genetic Modification of the Lung Directed Toward Treatment of Human Disease" Human Gene Therapy 28:1 3-84.
Smith et al. (2009) "A simplified baculovirus-AAV expression vector system coupled with one-step affinity purification yields high-titer rAAV stocks from insect cells" Molecular Therapy, 17:11 1888-1896.
Smith et al. (1993) "Biocomputing; Informatics and Genome Projects" Academic Press, p. 336.
Smith et al. (2016) "Germline viral "fossils" guide in silico reconstruction of a mid-Cenozoic era marsupial adeno-associated virus" Science Report, 6:28965.
Srivastava (2016) "Adeno-Associated Virus: The Naturally Occurring Virus Versus the Recombinant Vector" Human Gene Therapy, 27:1 1-6.
Srivastava (2016) "In Vivo Tissue-tropism of Adeno-associated Viral Vectors" Current Opinion in Virology, 21: 75-80.
Srivastava et al. (1983) "Nucleotide sequence and organization of the adeno-associated virus 2 genome" Journal of Virology, 45:2 555-564.
Stahl et al. (2008) "Pharmaceutical Salts: Properties, Selection, and Use" Wiley-VCH, 388 Pages.
Su et al. (2010) "Real-time MR imaging with gadoteridol predicts distribution of transgenes after convection-enhanced delivery of AAV2 vectors" Molecular Therapy, 18:8 1490-1495.
Su et al. (2016) "Recombinant adeno-associated viral (rAAV) vectors mediate efficient gene transduction in cultured neonatal and adult microglia" Journal Neurochemistry, 136 Suppl 1: 49-62.
Summerford et al. (2016) "AAVR: A multi-serotype receptor for AAV" Molecular Therapy, 24:4 663-666.
Suzuki et al. (2017) "Cochlear gene therapy with ancestral AAV in adult mice: complete transduction of inner hair cells without cochlear dysfunction" 7:45524.
Tarantal et al. (2017) "Systemic and Persistent Muscle Gene Expression in Rhesus Monkeys with a Liver De-targeted Meno-Associated Virus (AAV) Vector" Human Gene Therapy, 28:5 385-391.
Thorne et al. (2017) "Gene Therapy" Advances in Biochemical Engineering/Biotechnology, 165:351-399.
Tratschin et al. (1985) "Adeno-associated virus vector for high-frequency integration, expression, and rescue of genes in mammalian cells" Molecular and Cellular Biology, 5:11 3251-3260.
Urabe et al. (2006) "Scalable generation of high-titer recombinant adeno-associated virus type 5 in insect cells" Journal of Virology, 80:4 1874-1885.
Van Der Loo et al. (2016) "Progress and challenges in viral vector manufacturing" Human Molecular Genetics, 25:R1 R42-52.
Varenika et al. (2008) "Detection of infusate leakage in the brain using real-lime imaging of convection-enhanced delivery" Journal of Neurosurgery, 109:5 874-880.
Von Heijne (1987) "Sequence Analysis in Molecular Biology" Academic Press, 202 pages.
(2016) "Voyager Therapeutics Announces Positive Interim Results from Phase 1 b Trial of VY-AADC01 for Advanced Parkinson's Disease" Voyager Therapeutics—Investors & Media—Press Release, 1-6.
Wang et al. (2015) "Comparative study of liver gene transfer with AAV vectors based on endogenous and engineered AAV capsids" Molecular Therapy, 23:12 1877-1887.
Wang et al. (2017) "Direct brain infusion can be enhanced with focused ultrasound and microbubbles" Journal of Cerebral Blood Flow & Metabolism, 37:2 706-714.
Wang et al. (2017) "Direct interaction of human serum proteins with AAV virions to enhance AAV transduction: Immediate impact on clinical applications" Gene Therapy, 24:1 49-59.
Wang et al. (2014) "Noninvasive, neuron-specific gene therapy can be facilitated by focused ultrasound and recombinant adeno-associated virus" Gene Therapy, 104-110.
Wang et al. (2015) "Productive life cycle of adeno-associated virus serotype 2 in the complete absence of a conventional polyadenylation signal" Journal of General Virology 96:9 2780-2787.
Wasilko et al. (2009) "The titerless infected-cells preservation and scale-up (TIPS) method for large-scale production of NO-sensitive human soluble guanylate cyclase (sGC) from insect cells infected with recombinant baculovirus" Protein Expression and Purification, 65:2 122-132.
Watakabe et al. (2015) "Comparative analyses of adeno-associated viral vector serotypes 1 2 5 8 and 9 in marmoset mouse and macaque cerebral cortex" Neuroscience Research, 93:144-157.
Watson et al. (2016) "Adeno-associated Virus Vectors Efficiently Transduce Mouse and Rabbit Sensory Neurons Coinfected with Herpes Simplex Virus 1 following Peripheral Inoculation" Journal of Virology 90:17 7894-7901.
Weber-Adrian et al. (2015) "Gene delivery to the spinal cord using MRI-guided focused ultrasound" Gene Therapy 22:7:568-577.
Woodard et al. (2016) "Heparan Sulfate Binding Promotes Accumulation of Intravitreally Delivered Adeno-associated Viral Vectors at the Retina for Enhanced Transduction but Weakly Influences Tropism" Journal of Virology, 90:21 9878-9888.
Wu et al. (2016) "Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush" Frontiers in Molecular Neuroscience, 9:49.
Wu et al. (2000) "Mutational analysis of the adeno-associated virus type 2 (AAV2) capsid gene and construction of AAV2 vectors with altered tropism" Journal of Virology, 74:18 8635-8647.
Xiao et al. (2016) "Disruption of microtubules post virus entry enhances adeno-associated virus vector transduction" Human Gene Therapy, 2:4 309-324.
Xie et al. (2002) "The atomic structure of adeno-associated virus (AVV-2), a vector for human gene therapy" Proceedings of the National Academy of Sciences of the United States of America, 99:16 10405-10410.
Xie et al. (2017) "The 2.8 A Electron Microscopy Structure of Adeno-Associated Virus-DJ Bound by a Heparinoid Pentasaccharide" Molecular Therapy Methods Clinical Development, 8:5:1-12.
Yalvac et al. (2016) "AAV1.NT-3 gene therapy attenuates spontaneous autoimmune peripheral polyneuropathy" Gene Therapy 23:1 95-102.
Yan et al. (2015) "Optimization of recombinant adeno-associated virus mediated expression for large transgenes, using a synthetic promoter and tandem array enhancers" Human Gene Therapy, 26:6 334-346.
Yang et al. (2016) "Sequential adeno-associated viral vector serotype 9-green fluorescent protein gene transfer causes massive inflammation and intense immune response in rat striatum" Human Gene Therapy, 27:7 528-543.
Ye et al. (2015) "Adeno-Associated Virus Vector Mediated Delivery of the HBV Genome Induces Chronic Hepatitis B Virus infection and Liver Fibrosis in Mice" PLOS One, 10:6 e0130052.
Zhao et al. (2000) "BPV1 E2 protein enhances packaging of full-length plasmid DNA in BPV1 pseudovirions" Virology, 272:2 382-393.
Zhu et al. (2017) "Soluble FL T1 Gene Therapy Alleviates Brain Arteriovenous Malformation Severity" Stroke, 48:5 1420-1423.
Benskey MJ, et al. Targeted gene delivery to the enteric nervous system using AAV: a comparison across serotypes and capsid mutants. Mol Ther. Mar. 2015;23(3):488-500.
Castle MJ, et al. Controlling AAV Tropism in the Nervous System with Natural and Engineered Capsids. Methods . Mol Biol. 2016; 1382:133-49.
Chamberlain K, et al. Expressing transgenes that exceed the packaging capacity of AAV capsids. Hum Gene Ther Methods. Feb. 2016;27(1):1-12.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.

(56) References Cited

OTHER PUBLICATIONS

Choudhury SR, et al. Widespread CNS gene transfer and silencing after systemic delivery of novel AAV-AS vectors. Mol Ther. Apr. 2016;24(4):726-35.
Choudhury et al. In Vivo Selection Yields AAV-B1 Capsid for Central Nervous System and Muscle Gene Therapy. Mol Ther. Aug. 2016;24(7):1247-57.
Davis AS, et al. Rational design and engineering of a modified adeno-associated virus (AAV1)-based vector system or enhanced retrograde gene delivery. Neurosurgery. Feb. 2015;76(2):216-25.
Davidsson M, et al . A novel process of viral vector barcoding and library preparation enables high-diversity library generation and recombination-free paired-end sequencing. Sci Rep. Nov. 2016;6:3563.
Deverman BE et al. Cre-dependent selection yields AAV variants for widespread gene transfer to the adult brain, Nat Biotechnol. Feb. 2016;34(2):204-9.
Earley LF, et al. Identification and Characterization of Nuclear and Nucleolar Localization Signals in the Adeno-associated Virus Serotype 2 Assembly-Activating Protein. J Viral. Mar. 2015, 89(6):3038-48.
Grimm D, et al. E Pluribus Unum: 50 years of research, millions of viruses and one goal-tailored acceleration of AAV evolution. Mol Ther. Dec. 2015;23(12):1819-1831.
Haery et al., Adeno-Associated Virus Technologies and Methods for Targeted Neuronal Manipulation. Front. Neuroanat.. Nov. 26, 2019.
Halder S, et al. Structure of neurotropic adeno-associated virus AAVrh.8. J Stuct Biol. Oct. 2015;192(1):21-36.
Han et al. , Interventional MRI-guided catheter placement and real time drug delivery to the central nervous system. Expert review of neurotherapeutics Jun. 2, 2016;16(6):635-9.
Heiss JD et al Ia., Trial of magnetic resonance-guided putaminal gene therapy for advanced Pakinson's disease. Mov Disord. May 30, 2019. [Epub ahead of print).
International Search Report received in corresponding PCT application No. PCT/US2018/042391 dated Oct. 12, 2018.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Keravala A, et al. Evaluating AAV Hybrid Variants for Improved Tropism after Intravitreal Gene Delivery to the Retina. Molecular Therapy, vol. 23, Supplement1 , May 2015, pp. S127-S128.
Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Ling C, et al. Development of Optimized AAV Serotype Vectors for High-Efficiency Transduction at Further Reduced Doses. Hum Gene Ther Methods. Aug. 2016;27(4):143-9.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Mao Y, et al. Single point mutation in adeno-associated viral vectors—DJ capsid leads to improvement for gene delivery in vivo. BMC Biotechnol. Jan. 2016;16:1.
Marsic D et al. Altering Tropism of rAAV by Directed Evolution. Methods of Mol Bioi. 2016;1382:151-73.
Meneghini et al., Pervasive supply of therapeutic lysosomal enzymes in the CNS of normal and Krabbe-affected non-human primates by intracerebral lentiviral gene therapy. EMBO molecular medicine. May 1, 2016;8(5):489-510.
Mingozzi F, et al. Adeno-associated viral vectors at the frontier between tolerance and immunity. Front Immunol.Mar. 2015, 6:120.
Pillay S, et al. An essential receptor for adeno-associated virus infection. Nature. Feb. 2016;530{7588):108-12.
Powell SK et al. Characterization of a novel adeno-associated viral vector with preferential oligodendrocyte tropism. Gene Ther. Sep. 15, 2016.
Rosenbluth et al., Design of an in-dwelling cannula for convection-enhanced delivery. Journal of neuroscience methods. Mar. 15, 2011;196(1):118-23.
Rosenbluth et al., Automated segmentation tool for brain infusions. PloS one. 2013;8(6) . . . .
Rowland et al., Merging DBS with viral vector or stem cell implantation: "hybrid" stereotactic surgery as an evolution in the surgical treatment of Parkinson's disease. Molecular Therapy—Methods & Clinical Development. Jan. 1, 2016;3:15051.
Salegio et al., Magnetic resonance imaging-guided delivery of adena-associated virus type 2 to the primate brain for the treatment of lysosomal storage disorders. Human gene therapy. Sep. 1, 2010;21(9):1093-103.
Salegio et al., Guided delivery of adena-associated viral vectors into the primate brain. Advanced drug delivery reviews. May 15, 2012;64(7):598-604.
Salegio et al., MRI-guided delivery of viral vectors. InGene Therapy for Neurological Disorders 2016 (pp. 217-230). Humana Press, New York, NY.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1 14):e88728.
Sudhakar et al. , Development of a novel frameless skull-mounted ball-joint guide array for use in image-guided neurosurgery. Journal of neurosurgery. Feb. 15, 2019;1(aop):1-0.
Sudhakar V et al., Infuse-as-you-go convective delivery to enhance coverage of elongated brain targets: technical note. J Neurosurg. Jul. 12, 2019:1-8.
Taghian et al., A .Safe and Reliable Technique for Central Nervous System Delivery of AA V Vectors in the Cisterna Magna. Molecular Therapy. Nov. 16, 2019.
Tervo et al. A Designer AAV Variant Permits Efficient Retrograde Access to Projection Neurons. Neuron. Oct. 19, 2016;92(2):372-382.
Tu MY, et al. Role of capsid proteins in parvoviruses infection. Virol J. Aug. 2015, 4;12:114.
Vercauteren K, et al. Superior in vivo Transduction of Human Hepatocytes Using Engineered AAV3 Capsid. Mol Ther. Jun. 2016;24(6):1042-9.
Xie J, et al. Short DNA Hairpins Compromise Recombinant Adeno-Associated Virus Genome Homogeneity. Mol Ther. Jun. 7, 2017;25(6):1363-1374.
Yin et al., Optimal region of the putamen for image-guided convection-enhanced delivery of therapeutics in human and non-human primates. Neuroimage. Jan. 1, 2011 ;54:8196-203.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E. et al. In Silico Reconstruction of the Viral Evolutionary Lineage Yields a Potent Gene Therapy Vector. Cell Rep. Aug. 2015, 12(6):1056-68.
Zou W, et al. Nonstructural protein NP1 of human bocavirus 1 plays a critical role in the expression of viral capsid proteins. J Virol. Apr. 2016;90(9):4658-69.

\* cited by examiner

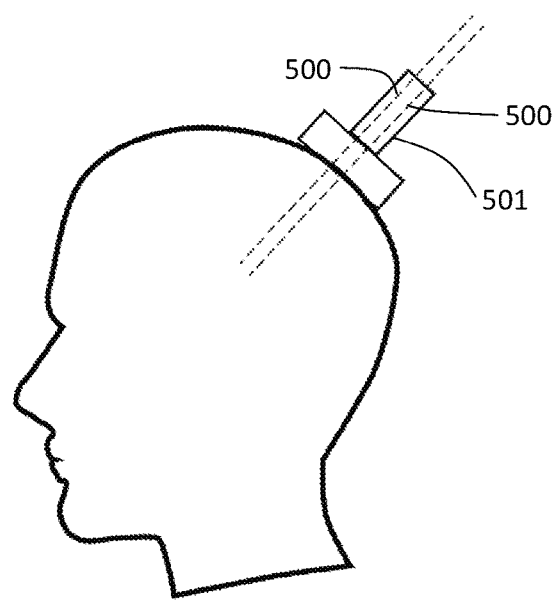
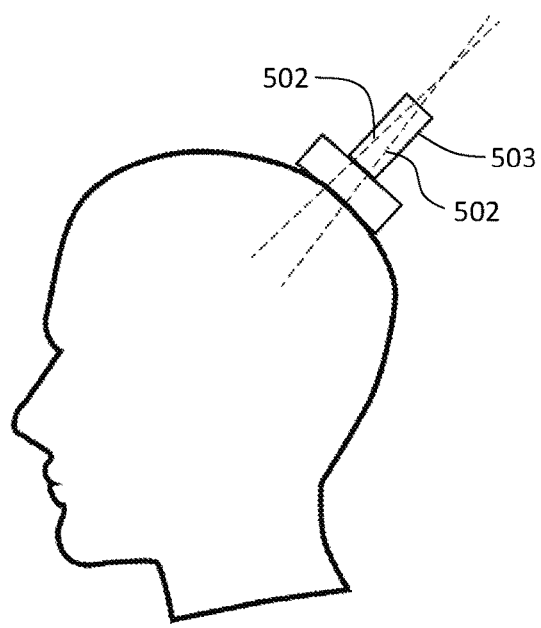
FIG. 5A
FIG. 5B
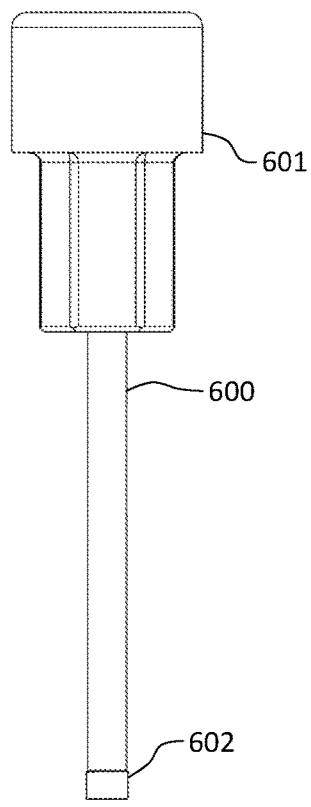
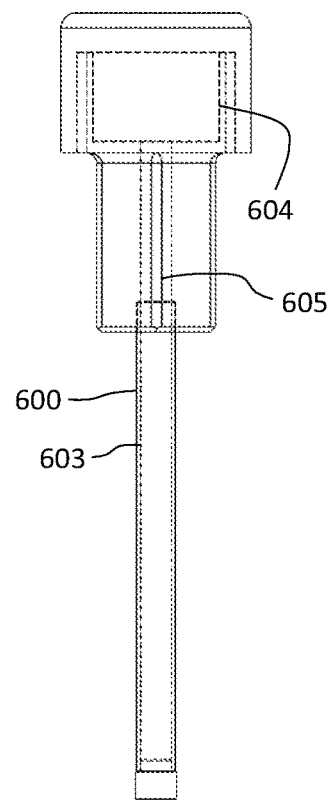
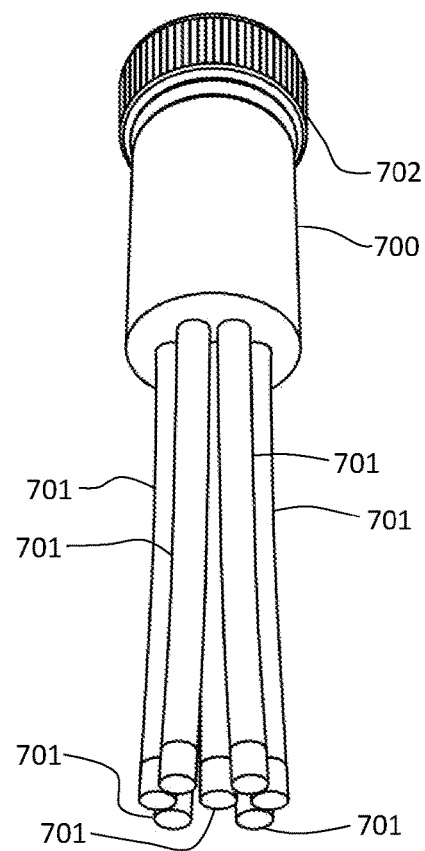
FIG. 6A
FIG. 6B
FIG. 7A

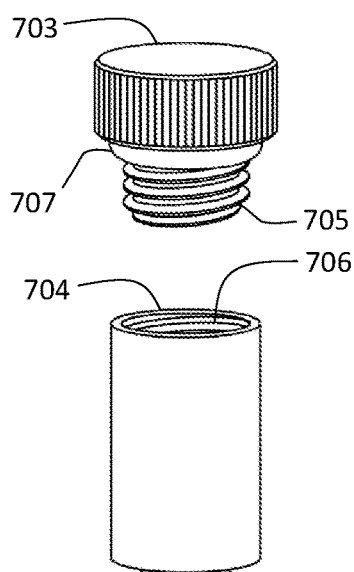
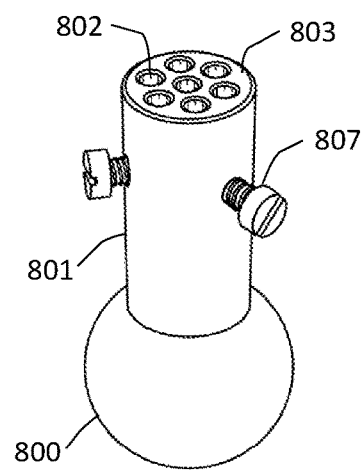
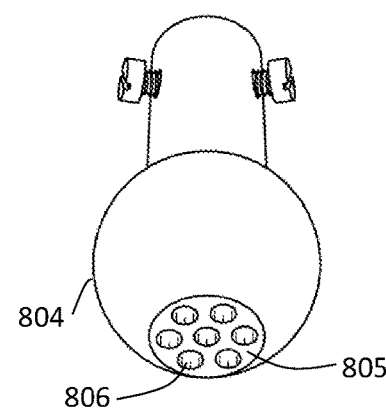
FIG. 8A
FIG. 8B
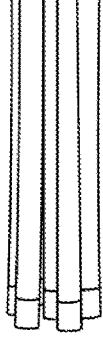
FIG. 7B
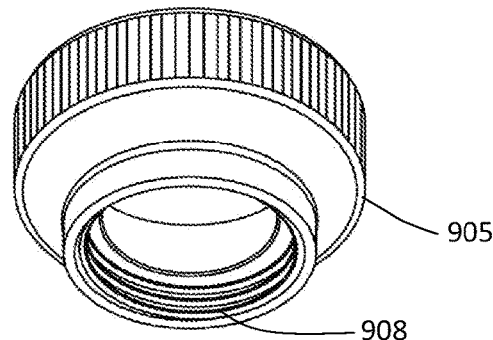
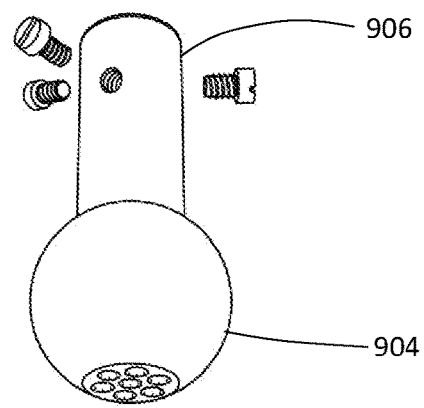
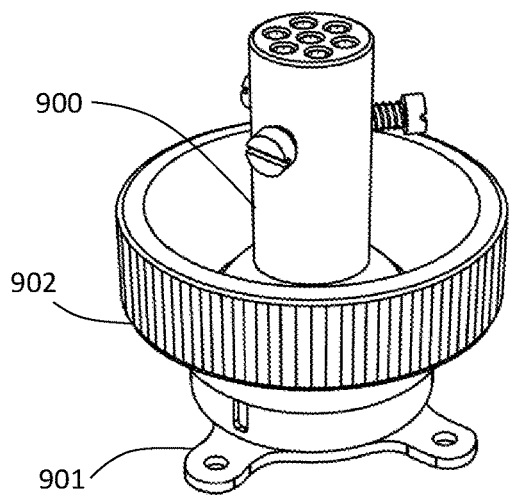
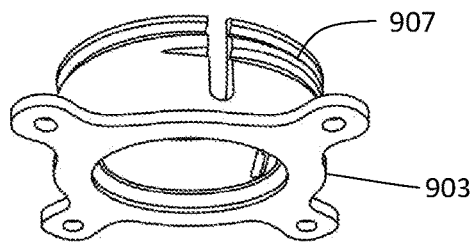
FIG. 9A
FIG. 9B

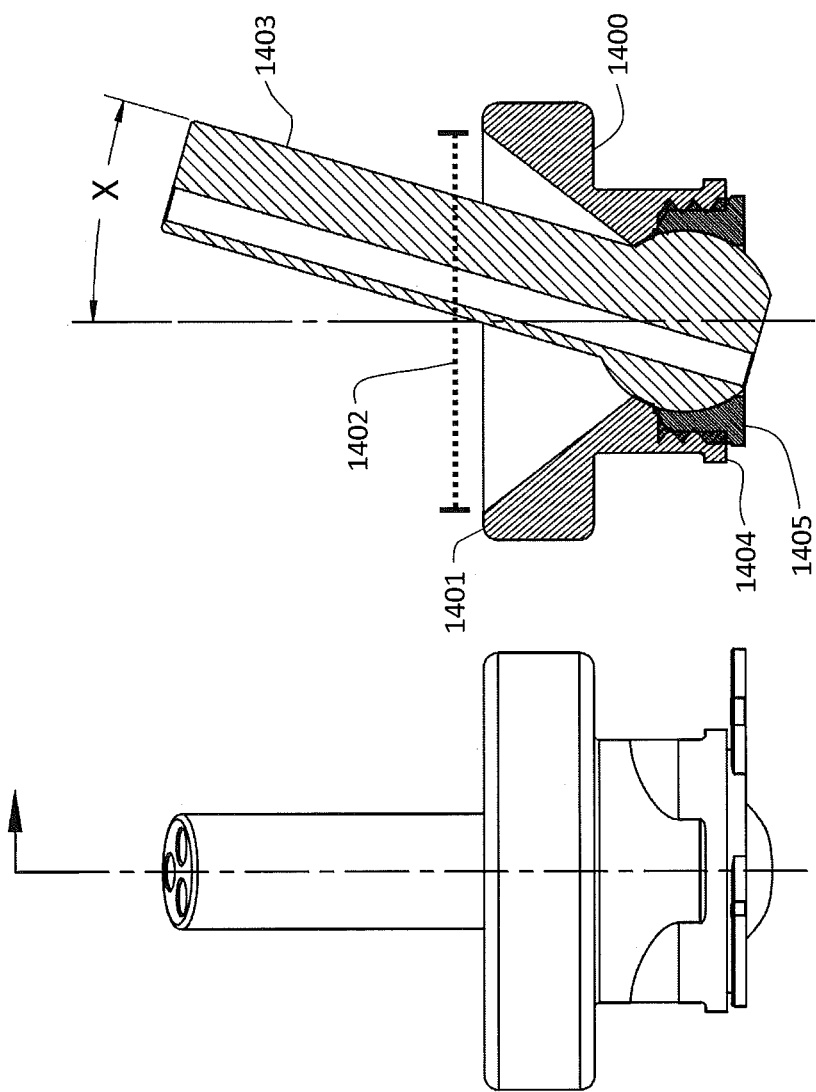
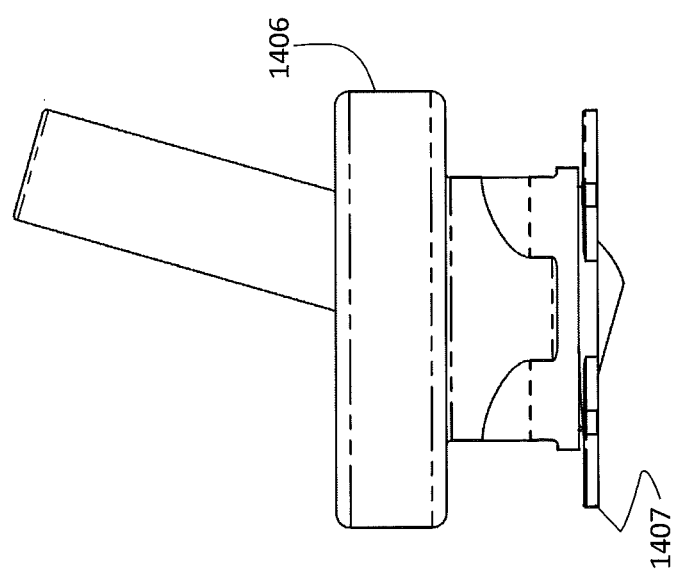
FIG. 14C
FIG. 14B
FIG. 14A

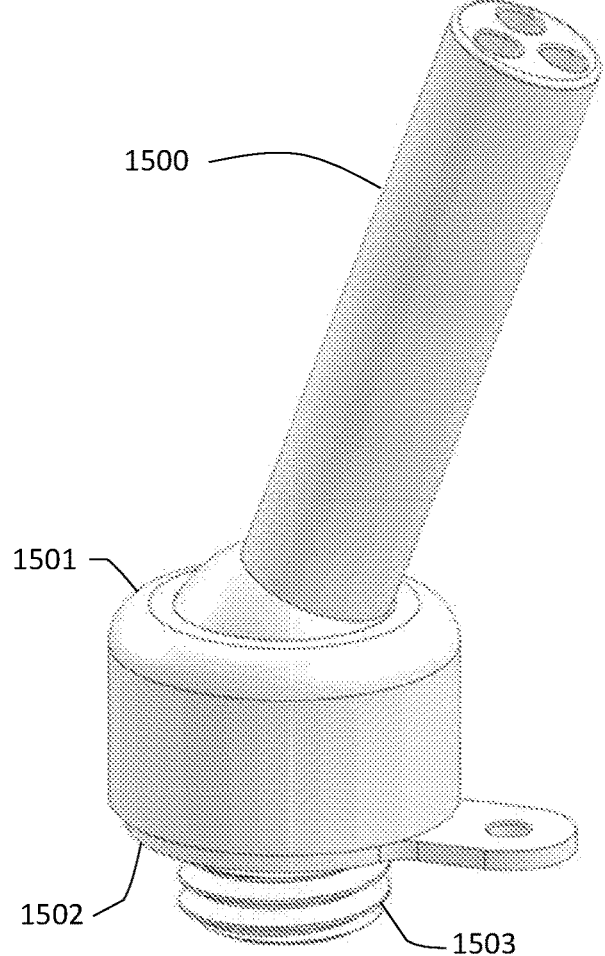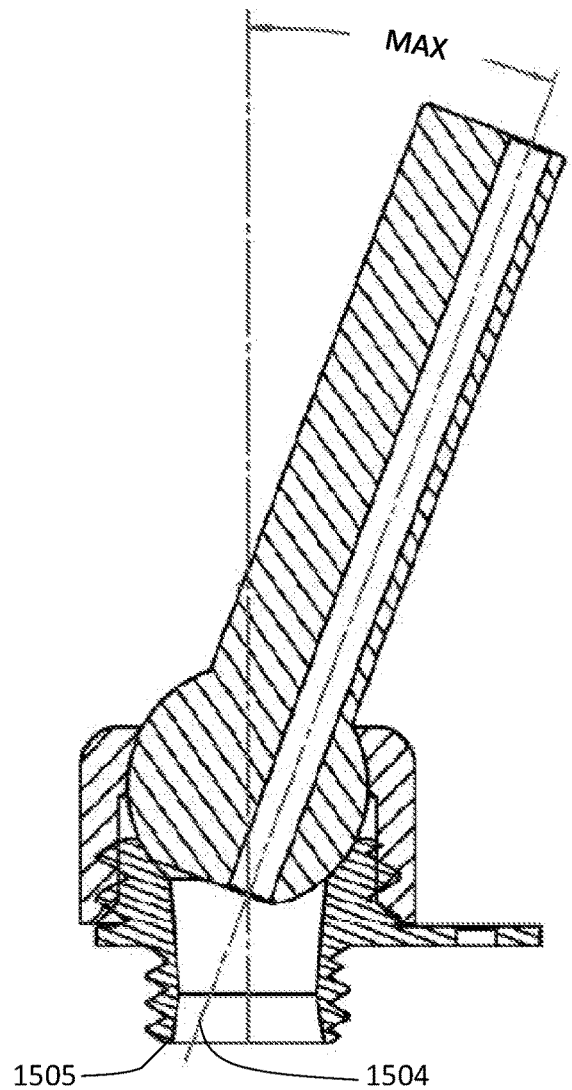
FIG. 15A
FIG. 15B

METHODS FOR BIOMEDICAL TARGETING AND DELIVERY AND DEVICES AND SYSTEMS FOR PRACTICING THE SAME

CROSS-REFERENCE TO RELATED APPLICATIONS

This application is a continuation of U.S. application Ser. No. 16/562,260, filed on Sep. 5, 2019, which application is a continuation of U.S. application Ser. No. 16/222,763, filed on Dec. 17, 2018, now U.S. Pat. No. 10,426,375, which application is a continuation of U.S. application Ser. No. 16/039,044, filed Jul. 18, 2018, now U.S. Pat. No. 10,426,374, which is a continuation of PCT/US2017/049191, filed Aug. 29, 2017, which claims the benefit of U.S. Provisional Patent Application No. 62/381,423, filed Aug. 30, 2016, which application is incorporated herein by reference in its entirety.

STATEMENT REGARDING FEDERALLY SPONSORED RESEARCH

This invention was made with government support under Grant No. P01 CA118816 awarded by the National Institutes of Health. The government has certain rights in the invention.

BACKGROUND

Many biomedical applications using advanced drugs and therapeutic techniques still require that the drug be delivered or the therapy be applied to a precise location within the subject. Thus, proper therapeutic targeting remains an important aspect of many therapeutic procedures regardless of treatment modality.

Exemplary areas of biomedicine where precise targeting is advantageous include neurological medicine and neurosurgery. For example, treatment of central nervous system disorders can be challenging due to the protected compartmentalization of the brain and spinal cord by the blood-brain barrier. In many circumstances, microinjections into the brain parenchyma are important procedures to deliver drugs, viral vectors or cell transplants. Many brain diseases remain under treated because of a lack of sufficiently precise and easy to use brain targeting systems that can efficiently assist a healthcare provider in delivering a therapeutic agent locally to the disease site in the brain while minimizing residual damage to surrounding brain structures. Besides agent delivery, neuroablation within the brain and intracranial surgery facilitates the treatment of debilitating neurological disorders characterized by malfunctioning neurons such as epilepsy and malignant tissue such as brain tumors. Like precise agent delivery, these techniques require a high level of accuracy to be effective.

The benefit of precise targeting of therapeutic interventions is not limited to neurological disorders and may include essentially any treatment paradigm where the location of the affected tissues or the origin of disease producing cells is known.

SUMMARY

The present disclosure provides methods for targeting a biomedical system. Aspects of the subject methods include determining the trajectory of a targeting device using magnetic resonance imaging (MRI) of a MRI-visible style of a trajectory guide that is compatible with the targeting device. Targeted biomedical systems may be utilized for a variety of purposes including targeted delivery of a therapeutic, holding a therapeutic device, positioning of a therapeutic device and other uses. Also provided are devices and systems that can be used in practicing the described methods including but not limited to trajectory guides and adjustable targeting systems, as well as non-transitory computer readable medium storing instructions that, when executed by a computing device, cause a computing device to perform steps of the described methods.

Aspects of the present disclosure include a method of magnetic resonance imaging (MRI)-assisted targeting of a desired area of a subject, the method comprising: positioning an adjustable turret comprising a channel on a tissue surface of a subject; inserting a MRI-visible style of a trajectory guide within the channel of the adjustable turret; visualizing the MRI-visible style using an MRI imager; determining the trajectory of the channel based on the visualizing; and adjusting the adjustable turret based on the determined trajectory of the channel to target the desired area of the subject.

In some embodiments the adjustable turret is positioned ex vivo. In some embodiments, the method further comprises affixing a base to the tissue surface of the subject and mounting the adjustable turret to the base. In some embodiments, the base is positioned ex vivo. In some embodiments, the base comprises a flange and the affixing comprises mounting a fastener through the flange to affix the base to the tissue surface of the subject. In some embodiments, the method further comprises locking the adjustable turret in place following the adjusting. In some embodiments, the locking comprises tightening a locking collar to compress the adjustable turret between the locking collar and the base. In some embodiments, the locking comprises tightening a locking collar to compress the adjustable turret between a plurality of annular walls of the base. In some embodiments, the channel is not coaxial with the turret. In some embodiments, the adjusting comprises a roll adjustment relative to the long axis of the adjustable turret. In some embodiments, the adjusting comprises an angle adjustment relative to the long axis of the adjustable turret. In some embodiments, the adjustable turret comprises a plurality of channels. In some embodiments, the trajectory guide comprises a plurality of MRI-visible styles. In some embodiments, the trajectory guide has the same number of styles as the adjustable turret has channels.

Aspects of the present disclosure include a method of magnetic resonance imaging (MRI)-assisted delivery of an agent or an electrical current to a desired area of a subject, the method comprising: targeting the desired area of the subject according to any of the methods described above; removing the MRI-visible style from the channel following the adjusting; and delivering the agent or the electrical current through the channel to the desired area of the subject.

In some embodiments, the method comprises MRI-assisted delivery of an agent and the delivering comprises inserting a delivery device containing the agent into the channel. In some embodiments, the delivery device comprises a needle or cannula. In some embodiments, the agent is a gene therapy vector. In some embodiments, the delivery device comprises a depth stop positioned at a point along the length of the delivery device to prevent inserting the delivery device into the channel past said point. In some embodiments, the method comprises MRI-assisted delivery of an electrical current and the delivering comprises inserting an electrode into the channel. In some embodiments, the electrode comprises a depth stop positioned at a point along the length of the electrode to prevent inserting the electrode into the channel past said point.

Aspects of the present disclosure include a method of magnetic resonance imaging (MRI)-assisted delivery of an agent or an electrical current to a desired area of a subject, the method comprising: positioning an adjustable turret comprising a plurality of channels on a tissue surface of a subject; inserting each of a plurality of MRI-visible styles of a trajectory guide within each of the plurality of channels of the adjustable turret;
   visualizing the plurality of MRI-visible styles using an MRI imager; determining the trajectory of two or more channels of the plurality of channels based on the visualizing; identifying a channel of the two or more channels with the trajectory closest to the desired area of the subject; and delivering the agent or the electrical current through the channel with the trajectory closest to the desired area of the subject.

In some embodiments, the method further comprises adjusting the adjustable turret based on the determined trajectory of the identified channel to target said channel to the desired area of the subject.

Aspects of the present disclosure include a trajectory guide for magnetic resonance imaging (MRI)-assisted targeting of a desired area of a subject, comprising: a solid support comprising a flat surface; a MRI-visible style comprising a lumen comprising a contrast agent, wherein the MRI-visible style is affixed at one end to the flat surface and dimensioned for insertion into a channel of an adjustable turret affixed to a tissue surface of a subject thereby allowing targeting of the channel by visualizing the trajectory of the inserted MRI-visible style using an MRI imager.

In some embodiments, the trajectory guide comprises a plurality of MRI-visible styles. In some embodiments, the plurality of MRI-visible styles comprises two or more styles that are affixed symmetrically to the flat surface with respect to the geometric center of the flat surface. In some embodiments, the plurality of MRI-visible styles comprises at least one style that is affixed asymmetrically to the flat surface with respect to one or more styles of the plurality. In some embodiments, at least one MRI-visible style is affixed perpendicular to the flat surface. In some embodiments, at least one MRI-visible style is affixed at a flared angle to the flat surface. In some embodiments, the solid support comprises an opening, opposite the flat surface, adjoining a void within the solid support that is contiguous with the lumen of the MRI-visible style thereby allowing access to the void and the lumen. In some embodiments, the trajectory guide further comprises a cap for closing the opening. In some embodiments, the cap and the opening comprise compatible threading. In some embodiments, the contrast agent comprises gadolinium.

Aspects of the present disclosure include, an adjustable targeting system, the system comprising: an adjustable turret comprising a distal end, a spherical end and one or more channels running from the distal end to the spherical end; a base, comprising: a plurality of annular walls forming a socket dimensioned to receive the spherical end, threading on an external surface of the annular walls; a plurality of slots positioned between the plurality of annular walls; and a flange orthogonal to at least one of the annular walls for affixing the base to a tissue surface of a subject; and a locking collar comprising threading on an internal surface compatible with the threading on the external surface of the base, wherein turning the locking collar a first direction compresses the spherical end to lock the adjustable turret in a desired trajectory and turning the locking collar a second direction decompresses the spherical end to allow for retargeting of the trajectory of the adjustable turret.

In some embodiments, turning the locking collar the first direction compresses the spherical end between the base and the locking collar to lock the adjustable turret in a desired trajectory. In some embodiments, turning the locking collar the first direction compresses the spherical end between the plurality of annular walls of the socket to lock the adjustable turret in a desired trajectory. In some embodiments, the adjustable targeting system is configured such that when affixed to the tissue surface of the subject the base and the locking collar are ex vivo. In some embodiments, the adjustable targeting system is configured such that when affixed to the tissue surface of the subject the adjustable turret is ex vivo. In some embodiments, the spherical end comprises a flat portion opposite the distal end that comprises openings to the one or more channels. In some embodiments, the spherical end and the flat portion are dimensioned such that, when inserted into the socket, the flat portion is flush with the bottom surface of the base. In some embodiments, the locking collar comprises a knurled external surface to provide grip. In some embodiments, the base comprises a plurality of flanges orthogonal to at least one of the annular walls. In some embodiments, the system further comprises a trajectory guide according to any of those described above. In some embodiments, the system further comprises an MRI imager positioned to image a MRI-visible style of the trajectory guide when the MRI-visible style is inserted into a channel of the adjustable turret.

Aspects of the present disclosure include an adjustable targeted delivery system, the system comprising: an adjustable targeting system according to any of those described above; and a delivery device or electrode dimensioned for insertion into the one or more channels of the adjustable turret.

In some embodiments, the delivery device or electrode comprises a depth stop positioned at a point along the length of the delivery device or electrode to prevent inserting the delivery device into the one or more channels past said point.

Aspects of the present disclosure include, a non-transitory computer readable medium storing instructions that, when executed by a computing device, cause the computing device to perform the steps of: receiving a magnetic resonance image (MRI) of a trajectory guide MRI-visible style inserted within a channel of an adjustable turret; determining the trajectory of the channel based on the received MRI; comparing the determined trajectory to a desired user input trajectory; calculating a recommended adjustment of the adjustable turret necessary to align the determined trajectory with the desired user input trajectory based on the comparing; and displaying the recommended adjustment.

Aspects of the present disclosure include an automated adjustable targeting system, the system comprising: an adjustable targeting system according to those described above; an actuator connected to the adjustable turret and controlled by a processor programed with instructions that, when executed by the processor, cause the processor to: determine the trajectory of a channel of the adjustable turret based on a received magnetic resonance image (MRI) of a trajectory guide MRI-visible style inserted within the channel; compare the determined trajectory to a desired user input trajectory; calculate an adjustment of the adjustable turret necessary to align the determined trajectory with the desired user input trajectory based on the comparing; and trigger the actuator to execute the adjustment thereby aligning the determined trajectory with the desired user input trajectory.

BRIEF DESCRIPTION OF THE FIGURES

FIGS. 5A-5B depict targeting device turrets having parallel and non-parallel channels.

FIGS. 6A-6B depict a targeting guide and a cutaway thereof according to an embodiment described herein.

FIGS. 7A-7B depict a targeting guide having a plurality of MRI-visible styles according to an embodiment described herein.

FIGS. 8A-8B depict adjustable turrets of a targeting device as described herein.

FIGS. 9A-9B depict an assembled and unassembled multi-component targeting device as described herein.

FIGS. 14A-14C depict an assembled ex vivo targeting system according to an embodiment described herein.

FIGS. 15A-15B depict a targeting system, as described herein, having a base with an in vivo portion.

DEFINITIONS

Figure 1:
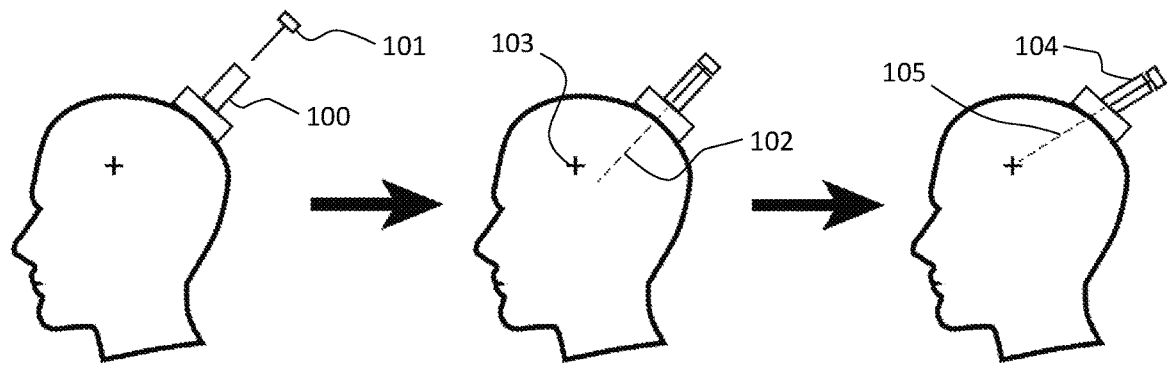
FIG. 1 depicts a method of targeting a device to a desired region according to an embodiment described herein.

As used herein, "treatment" or "treating" refers to inhibiting the progression of a disease or disorder, or delaying the onset of a disease or disorder, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse effect attributable to the disease or disorder. "Treatment," as used herein, covers any treatment of a disease or disorder in a mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated with neurological conditions.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute.

The term "inputting", as used herein, is used to refer to any way of entering information into a computer, such as, e.g., through the use of a user interface. For example, in certain cases, inputting can involve selecting a target or trajectory that is already present or identified on a computer system. In other cases, inputting can involve target or trajectory to a computer system, e.g., by defining a target or trajectory on an image within the computer system with or without first generating the image on a device capable of interfacing with a computer. As such, inputting can be done using a user interface, using a device configured to send information to the computer system, such as an image capture device, or any combination thereof.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based). Data processing units may, in some instances, be specialized for particular purpose, such as, e.g., an image processing unit specialized to receive and process image data.

As used herein, the term "executing" is used to refer to an action that a user takes to initiate a program.

DETAILED DESCRIPTION

The present disclosure provides methods for targeting a biomedical system. Aspects of the subject methods include determining the trajectory of a targeting device using magnetic resonance imaging (MRI) of a MRI-visible style of a trajectory guide that is compatible with the targeting device. Targeted biomedical systems may be utilized for a variety of purposes including targeted delivery of a therapeutic, holding a therapeutic device, positioning of a therapeutic device and other uses. Also provided are devices and systems that can be used in practicing the described methods including but not limited to trajectory guides and adjustable targeting systems, as well as non-transitory computer readable medium storing instructions that, when executed by a computing device, cause a computing device to perform steps of the described methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure provides methods for targeting a biomedical system. By "biomedical system" is meant any device or system of components used in medical or therapeutic applications including but not limited to treatment of a subject, diagnosis of a condition of a subject, biomedical research performed on a subject, and the like. Aspects of the subject methods generally, but not exclusively, include positioning a targeting device on the surface of a subject and establishing, aligning and/or adjusting the trajectory of the targeting device for one or more downstream applications that rely on the trajectory of the targeting device for proper placement of a medical device on or within the subject. In some instances, aspects of the subject methods may also include utilizing the herein described devices, or components thereof, as a holder for therapeutic administration devices including but not limited to e.g., drug delivery devices, viral vector delivery devices, nanoparticle delivery devices, cell administration delivery devices, cell delivery devices, and the like. The actual configuration of a targeting device of the subject disclosure will vary.

In some instances, a targeting device of the subject disclosure may include an adjustable turret having one or more channels, the trajectory of which is relied upon for proper positioning of a medical device inserted into one or more of the channels. According to some embodiments, the targeting device may be attached to the surface of a subject and adjusting the adjustable turret allows for adjusting the trajectory of the one or more channels of the turret to better target a desired area of the subject or to avoid an obstacle within the subject.

A targeting device may be initially positioned on a tissue surface of a subject. The initial position of the targeting device on the subject will vary depending on a number of factors including the position of one or more desired target areas of the subject, the position of one or more obstacles within the subject, and the like. In some instances, the tissue surface of the subject to which the targeting device is attached, establishing the initial position, is chosen because it is the tissue surface closest to a desired area on or into which a medical device is to be positioned. In some instances, the initial position is chosen because it is an accessible tissue surface, which may or may not be the closest accessible tissue surface to a desired area on or into which a medical device is to be positioned. In some instances, the initial positioning of the targeting device takes into account the underlying position of obstacles or likely underlying position of likely obstacles. For example, in some instances, the tissue surface closest to a desired area of a subject may not be used because doing so may require that the medical device be inserted through an obstacle or increase the chances that the medical device be inserted through an obstacle. In some instances, the initial positioning may not take into account the position of obstacles or the likely position of obstacles and the targeting device may be positioned and any obstacles may be subsequently avoided during targeting, e.g., as described further herein.

In some instances, the tissue surface upon which the targeting device is initially affixed may be first prepared for affixing the targeting device. Various methods of preparing the surface may be employed including but not limited to e.g., shaving or otherwise removing hair from the surface, cleaning and/or sterilizing the surface (e.g., by applying an alcohol, an alcohol-based cleaner, an iodine based-cleaner (e.g., povidone-iodine) solution, chlorhexidine gluconate, or the like), removing one or more layers of skin from the surface, covering the surface with a protective cover (e.g., a plastic adhesive drape), etc. In some instances, the surface may be prepared according to the current Association of Surgical Technologists (AST) Standards of Practice for Skin Prep of the Surgical Patient (e.g., as available online at www(dot)ast(dot)org). In some instances, the surface of the subject may not be prepared or may be minimally prepared prior to placing the targeting device including e.g., when used in an emergency application or field setting.

In some instances, the targeting device includes a base, either removable or non-removable, that can be used to affix the targeting device to a tissue surface of a subject. Various methods may be employed for attaching the base to the tissue surface of the subject. For example, in some instances, the base may be attached to the subject through the use of one or more adhesives including but not limited to surgical adhesives, dental acrylic, surgical/skin tape, etc. However, the use of adhesives is not necessarily required and, in some instances, the base is attached without the use of adhesive. In some instances, whether or not adhesives are used, the base may be attached to the subject through one or more fasteners including but not limited to e.g., sutures, buttons, staples, clips, screws, etc. As described in more detail below, in some instances, the base of the targeting device may include one or more features to facilitate attachment of the base to the subject including but not limited to e.g., a flange, a notch, an adhesion surface, etc. In some instances, a fastener may be placed through such a feature including e.g., where a screw is placed through a flange to attach the base to the subject, e.g., by screwing the base to a solid tissue of the subject including e.g., cartilage, bone, etc.

The base of the device may be attached directly to the tissue surface of the subject or may be attached indirectly including e.g., through the use of one or more intermediate structures including e.g., an attachment plate, an attachment frame, etc. Intermediate structures may be used in various situations including e.g., where the tissue to which the base would be otherwise attached is insufficient (e.g., of insufficient size, of insufficient density or rigidity for a desired method of attachment, etc.) for attachment of the base. For example, an intermediate structure (e.g., a frame or a plate) could be used when the base is to be positioned over a soft tissue of the subject, e.g., the eye of a subject, for device insertion into or near the soft tissue, e.g., the eye. However, such situations do not necessarily require an intermediate structure and in some instances e.g., the base could be attached directly to a small or less dense tissue of the subject including e.g., the eye.

In some instances, the targeting device may be attached to the subject such that all or nearly all components of the device remain outside the subject. In some instances throughout the instant disclosure such attachment may be referred to as substantially ex vivo, ex vivo and/or completely ex vivo. For example, the device may be attached such that the base is flush or nearly flush with the surface of the subject but remains substantially ex vivo or completely ex vivo. In some instances, the device may be attached such that the turret is flush or nearly flush with the surface of the subject but remains ex vivo. Components of certain devices that are intentionally inserted into the subject, including e.g., a delivery device, an electrode, a camera, attachment fasteners, etc., are generally not considered when a device is described as substantially ex vivo and/or completely ex vivo. As such, in some instances, a device may be simply described as ex vivo without addressing the inserted component or may be specifically described as ex vivo excluding the intentionally inserted component(s).

Following the attachment of the targeting device to the subject an adjustable turret of the device, and the channel(s) thereof, will generally have or be placed in an initial position or orientation. For example, in some instances, the turret may be arbitrarily positioned initially including e.g., arbitrarily positioned perpendicular to the attachment surface. In some instances, the turret may be initially positioned to approximate a desired trajectory. The initial position of the turret generally refers to the position of the turret following attachment to the subject but prior to any imaging-based adjustments of the turret.

Aspects of the instant methods include using a trajectory guide to determine the trajectory of one or more channels of an adjustable turret. As used herein the term "trajectory guide" generally refers to a device, described in more detail below, having one or more MRI-visible styles that can be inserted into one or more channels of an adjustable turret and imaged using an MRI to allow for a determination of the trajectory of the channel to be made. Thus, MRI visualization of the styles of a trajectory guide allow for simultaneous visualization of both the trajectory of the channel(s) and the target area and/or any obstacles within or near the trajectory.

Referring now to the example presented in FIG. 1, a targeting device of the instant disclosure is attached to the head of a subject. Then, to determine the trajectory of a channel within an adjustable turret (100) a style of a trajectory guide (101) is inserted into the channel and the system is subsequently MRI imaged. Following the imaging, the initial trajectory (102) of the channel may be determined based on the MRI-visible style and the relative positions of the initial trajectory and a targeted area of the subject's brain (103) may be determined. Once any difference between the position of the trajectory and the position of the targeted area of the brain are known, an adjustment may be made to bring the trajectory and the targeted position of the brain into alignment. For example, an angle adjustment of the adjustable turret (104) may be made to result in an adjusted trajectory (105) that aligns the adjusted trajectory or more closely aligns the adjusted trajectory with the target area.

Figure 2:
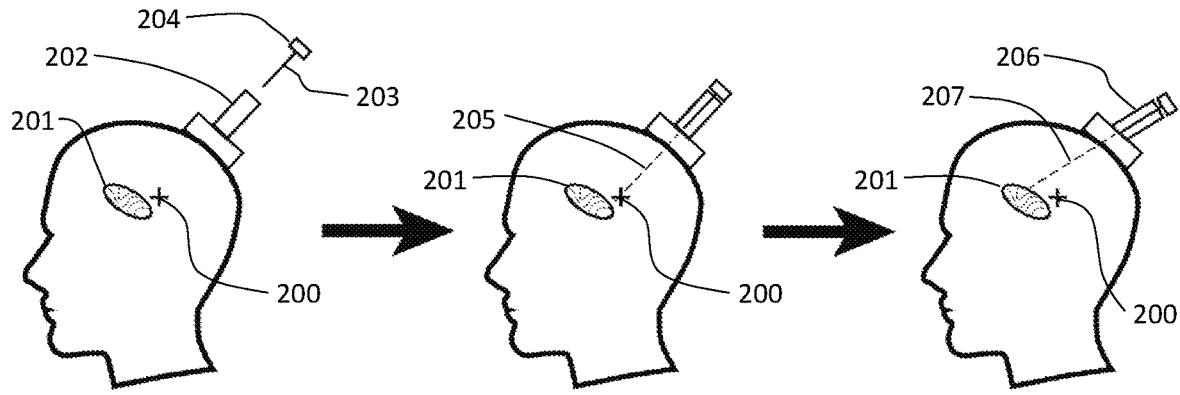
FIG. 2 depicts a method of targeting a device to a desired region while avoiding an obstacle according to an embodiment described herein.

Adjustments of a targeting device are not limited to those used to improve the targeting of a desired area of subject. For example, as depicted in FIG. 2, in some instances, targeting adjustments may be made to avoid an obstacle (200). In the embodiment depicted, a desired area of a subject's brain (201) is targeted using a targeting device having an adjustable turret (202). The MRI-visible style (203) of a targeting guide (204) is inserted into the adjustable turret (202) and the initial trajectory is determined (205). In the embodiment depicted, although the determined trajectory (205) is sufficient to target the desired area of the subject's brain (201) it is discovered that an obstacle (200) is in the path of the trajectory. Accordingly, an angle adjustment of the adjustable turret is made (206) that results in a desired trajectory (207) that sufficiently targets the desired area of a subject's brain (201) while avoiding the obstacle (200). In some instances, the necessary adjustment to achieve the desired trajectory is calculated prior to making the adjustment, e.g., so that a minimal number of adjustments must be made to achieve the desired trajectory, in what may be referred to as a "calculated" or "predetermined" approach. In some instances, the adjustment is made without calculating what adjustment is necessary and the adjusted trajectory is analyzed to determine if it achieves a desired trajectory (e.g., targets the desired area, avoids one or more obstacles, etc.) in what is commonly referred to as a "guess-and-check" approach.

Depicted in FIG. 1 and FIG. 2 are angle adjustments where an angle adjustment can be defined as modifying the angle of the adjustable turret relative to the long axis of the adjustable turret about a pivot point defined by the portion of the turret that rests within the base of the trajectory device. Accordingly, an angle adjustment may be measured using any convenient means and may be represented as the change in degrees between a starting trajectory and a modified trajectory. Useful angle adjustments will vary and will depend on a number of factors including e.g., the initial trajectory, the specific configuration of the targeting device, the size of the area to be targeted, etc. In some instances, an angle adjustment may range from 0.1° or less to 60° of more where the maximum angle adjustment may be limited by the configuration of the targeting device including components or parameters of the targeting device that physically prevent greater adjustment including but not limited to e.g., the size of the rounded end of the adjustable turret, the diameter of the turret, the size and shape of a locking ring, etc. In some instances, an angle adjustment may range from 0.1° to 60° including but not limited to e.g., 0.1° to 55°, 0.1° to 50°, 0.1° to 45°, 0.1° to 40°, 0.1° to 35°, 0.1° to 30° and the like.

As will be readily understood, adjustments of the adjustable turret are not limited to angle adjustments and may also include, e.g., roll adjustments. As used herein, the term "roll adjustment" generally refers to rotating the adjustable turret about its long axis. While roll adjustments may not change the trajectory of a channel that is coaxial with the adjustable turret, roll adjustments will modify the trajectory of channels that are not coaxial with the turret. In making roll adjustments the adjustable turret may be rotated essentially any amount up to 360° including but not limited to e.g., 1°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, 185°, 190°, 195°, 200°, 205°, 210°, 215°, 220°, 225°, 230°, 235°, 240°, 245°, 250°, 255°, 260°, 265°, 270°, 275°, 280°, 285°, 290°, 295°, 300°, 305°, 310°, 315°, 320°, 325°, 330°, 335°, 340°, 345°, 350°, 355°, and the like.

Determinations of the trajectory of a channel of an adjustable turret made using a trajectory guide may be performed manually or automatically with the choice of manual or automatic adjusting being dependent on a number of factors including but not limited to e.g., the level accuracy necessary, whether the adjustment is made manually or automatically, the number of adjustments likely to be performed (e.g., during a particular targeting session), etc.

Manual determinations of the trajectory of a channel of an adjustable turret may be performed by a variety of approaches. In one embodiment, on a computer displayed or printed image of the MRI-visible style the path of the MRI-visible style is traced to determine the trajectory. In some instances, to determine the difference between a determined trajectory and a desired trajectory two lines are drawn: one defined by the path of the MRI-visible style and the other defined by the target and rounded end of the adjustable turret. The angle between the two lines is determined, e.g., through the use of a measuring device e.g., a protractor, or through computer assisted measuring, e.g., software programming that measures the angle, to determine the difference between the determined trajectory and the desired trajectory.

In some instances, determination of the trajectory of a channel of an adjustable turret may be automated. For example, a processor may be programmed to recognize the MRI-visible style from a digital MRI image and automatically plot the trajectory of the style. The plotted trajectory may or may not be displayed on the digital MRI image. In some instances, the automatically plotted trajectory is displayed on a digital MRI image such that a user may make a determination as to whether the plotted trajectory achieves the desired trajectory (e.g., targets the desired area, avoids one or more obstacles, etc.). A user may, in some instances, provide an input to the computer system to indicate whether a desired trajectory and/or what adjustment may be necessary to achieve a desired trajectory.

In some instances, an automatically plotted trajectory is automatically analyzed according to instructions programmed into the computer system to determine whether a desired trajectory is achieved. For example, a user may provide an input representing a desired target area or one or more obstacles to be avoided and the computer system may automatically calculate the trajectory and automatically determine whether the calculated trajectory targets the desired area and/or avoids one or more obstacles. The computer system may then, following the automatic determination, indicate to the user whether the calculated trajectory is sufficient and, if not, the computer system may or may not be further programed to suggest an adjustment to the trajectory sufficient to target the desired area and/or avoid one or more obstacles. In some instances, an automated system may be further programed to automatically make the necessary adjustment to achieve a desired trajectory.

As will be readily understood, the above described trajectory determinations, whether manual or automated, may be equally applied in some instances to a plurality of trajectories. Multiple trajectories may be determined in series, i.e., one after the other, e.g., where a process of determining a trajectory of a channel, making an adjustment and re-determining the trajectory is repeated, e.g., until a desired trajectory of the channel is achieved. In some instances, multiple trajectories of a plurality of channels may be determined in parallel, i.e., essentially simultaneously. For example, where a trajectory guide having a plurality of MRI-visible styles is employed, the trajectory of two or more channels may be determined at one time based on two or more styles, including all of the styles, of the plurality.

Figure 3:
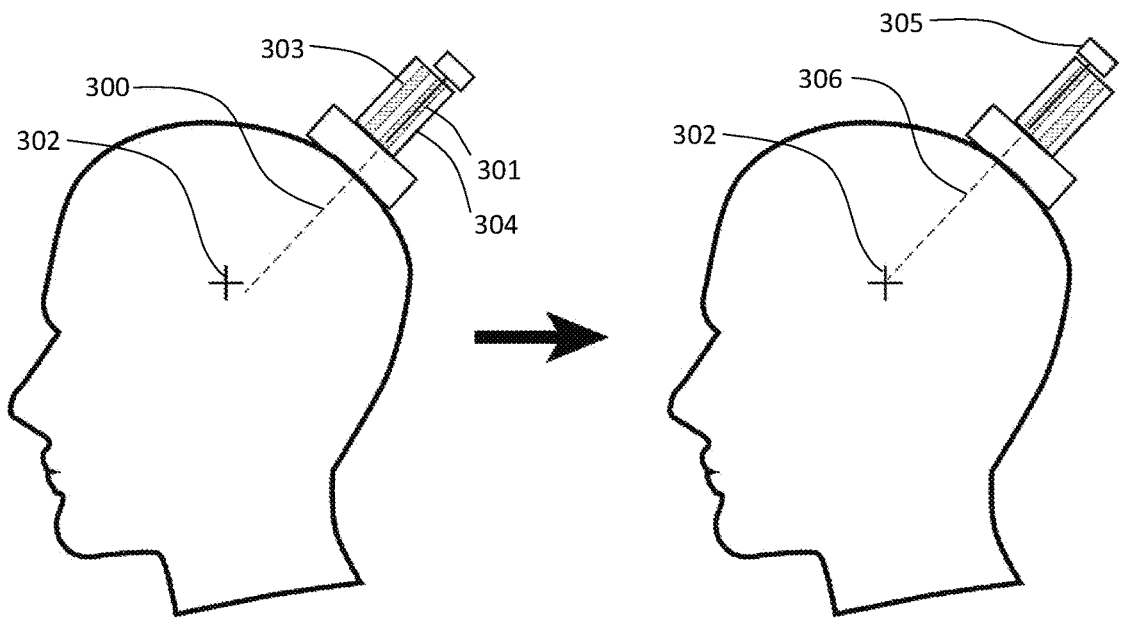
FIG. 3 depicts channel selection of a multi-channel targeting device according to an embodiment of the method described herein.

In some instances, e.g., when multiple trajectories for a plurality of channels are determined, the targeting of a device may be modified by choosing one channel over another based on comparing the determined trajectories of the channels. For example, as depicted in FIG. 3, the trajectory (300) of a first channel (301) may be determined and that the trajectory does not sufficiently target a desired area of a subject's brain (302) may be recognized. At which point a second channel (303) of the adjustable turret (304) may be investigated to determine if it achieves a desired trajectory to the target area. Accordingly, the targeting guide (305) may be moved to the second channel (303) and the trajectory (306) of the second channel may be determined. Where the second channel trajectory (306) is sufficient to target the desired area of the subject's brain (302) then the second channel may be chosen and no further adjustment, e.g., of the adjustable turret, may be necessary. Alternatively, in some instances, neither channel may directly target the desired area and thus the channel having the trajectory that most closely targets the desired area may be chosen and further adjustment of the adjustable turret may be employed to refine the targeting.

As will be readily understood, where an adjustable turret having a plurality of channels and a trajectory guide having a plurality of MRI-visible styles are employed, removing the style from a first channel and placing the style into a second channel, as described in the above embodiment, may not be necessary essentially because some or all of the plurality of channels may simultaneously contain MRI-visible styles allowing for parallel determinations of channel trajectory to be performed. Accordingly, in some instances, a plurality of trajectories may be determined in parallel for an adjustable turret having a plurality of channels and the channel having the trajectory that best targets the desired area may be chosen without removing and replacing the trajectory guide.

Channel selection using an adjustable turret having a plurality of channels may be combined with any of the turret adjustments described herein. For example, in some instances, a channel may be selected having a trajectory nearest the desired trajectory and a roll adjustment may be performed to refine the trajectory. In some instances, a channel may be selected having a trajectory nearest the desired trajectory and an angle adjustment may be performed to refine the trajectory. In some instances, a channel may be selected having a trajectory nearest the desired trajectory and a roll and an angle adjustment may be performed to refine the trajectory.

Following the selection of a channel, an adjustment of the turret or a combination thereof, the selected/adjusted trajectory may be verified. Verification of the trajectory may be performed by a variety of means including but not limited to e.g., determining the trajectory using a trajectory guide and plotting the trajectory on a MRI image of the subject. The plotted trajectory may be checked to verify that the desired area is, in fact, targeted, that the plotted trajectory avoids any obstacles, etc. Where verification confirms that the plotted trajectory is, in fact, a sufficient or desired trajectory then the device may be considered to be sufficiently targeted and downstream uses of the targeted device may be performed. Where verification is unable to confirm that the plotted trajectory is sufficient then iterative adjustments may be employed until a desired trajectory is achieved.

At various points within the method, the position of the adjustable turret may be locked to prevent further adjustment. For example, in some instances, the adjustable turret may be locked in its initial position, e.g., before the initial trajectory of one or more channels is determined. In some instances, the position of the adjustable turret may be locked following adjustment and/or when a trajectory of a channel of the adjustable turret is verified as sufficiently targeted. Locking of the adjustable turret will generally include placing the adjustable turret in a state that does not allow for further adjustment, either angle adjustment and/or roll adjustment, of the turret under normal conditions. In some instances, locking of the turret may involve the use of a locking collar, as described in more detail below, including but not limited to e.g., a locking collar that compresses the round end of the adjustable turret between the base and the locking collar, thus preventing movement.

As briefly discussed above, at various points in the herein described methods the MRI-visible style(s) of the trajectory guide may be removed from the channel(s) of the adjustable turret and/or replaced as desired. Generally, the position of the adjustable turret may be locked prior to removing the MRI-visible style(s), e.g., to maintain a determined trajectory. After channel selection, turret adjustment or combinations thereof to identify or arrive at a sufficient or desired trajectory, the MRI-visible styles will generally be removed to allow access to the targeted channel and insertion of a device into the targeted channel, e.g., as part of a therapeutic method making use of the targeting device.

Therapeutic Methods

Aspects of instant methods include, in some instances, magnetic resonance imaging (MRI)-assisted delivery to a desired area of a subject using one or more targeted channels of a targeting device as described above. Any desired therapeutic agent or therapeutic device may be targeted and delivered to a desired area of a subject according to the methods described herein. Non-limiting examples of agents and therapeutic devices that may be delivered through a targeted channel as described herein include but are not limited to e.g., drugs, nanoparticles, biological agents (e.g., cells, virus, etc.), electrical probes (e.g., electrodes), thermal probes (e.g., heat probes, cold probes, etc.), imaging devices (e.g., endoscopes, lights, etc.), surgical implements, and the like.

Subjects to which the methods of the instant disclosure are applicable include veterinary subjects (e.g., dogs, cats, horses, etc.) and research animal subjects (e.g., mice, rats, rabbits, pigs, goats, sheep, primates, etc.) as well as human subjects. The methods of the invention are applicable to all primates, including e.g., simians. In some embodiments the methods are applied to humans. In other embodiments the methods are applied to non-human primates.

A primate is a member of the biological order Primates, the group that contains lemurs, the Aye-aye, lorisids, galagos, tarsiers, monkeys, and apes, with the last category including great apes. Primates are divided into prosimians and simians, where simians include monkeys and apes. Simians are divided into two groups: the platyrrhines or New World monkeys and the catarrhine monkeys of Africa and southeastern Asia. The New World monkeys include the capuchin, howler and squirrel monkeys, and the catarrhines include the Old World monkeys such as baboons and macaques and the apes.

Any desired area of a subject may be targeted according to the methods described herein. In some instances, the desired area may a tissue, including but not limited to a tissue of endodermal origin, a tissue of ectodermal origin, a tissue mesodermal origin. Both neural and non-neural tissues may be targeted. In some instances, neural tissues of the central nervous system (CNS) may be targeted including e.g., tissues of the brain and tissues of the spinal cord. In some instances, neural tissues of the peripheral nervous system may be targeted.

Non-neural tissues that may be targeted include but are not limited to the skin/epidermis, tissues of the eye, tissues of the olfactory system, tissues of the ear (including inner and outer ear), tissues of the mouth and throat, non-neural tissues of the neck (including e.g., muscles, connective tissues, etc.), tissues of the heart, tissues of the lungs, tissues of stomach, tissues of the intestine (e.g., small intestine, large intestine, colon, etc.), tissues of the liver, tissues of the kidney, tissues of the endocrine system, tissues of the lymphatic system, tissues of the bone (including e.g., the bone marrow), tissues of the vascular system (e.g., arteries, veins, etc.), tissues of the pancreas, tissues of the arms and legs (e.g., muscles, connective tissues in the joints, etc.).

In some instances, the methods of the instant application may be applied for effective delivery/localization of an agent to a region of interest in the mammalian nervous system, including the central nervous system or the peripheral nervous system. Essentially any region of interest of the nervous system may be targeted according to the methods as described herein, including but not limited to e.g., the brain, the spinal cord, the spinal ganglia, etc.

In some instances, the methods of the instant application may be applied for effective delivery/localization of an agent to a region of interest in the mammalian brain. Essentially any region of interest of the brain may be targeted according to the methods as described herein.

In some instances, one or more brain lobes or a particular area within a brain lobe may be targeted, including but not limited to e.g., the frontal lobe (either the entire frontal lobe or portions thereof including but not limited to e.g., Superior Frontal, Rostral Middle Frontal, Caudal Middle Frontal, Pars Opercularis, Pars Triangularis, and Pars Orbitalis, Lateral Orbitofrontal, Medial Orbitofrontal, Precentral, Paracentral, Frontal Pole, combinations thereof, and the like), parietal lobe (either the entire parietal lobe or portions thereof including but not limited to e.g., Superior Parietal, Inferior Parietal, Supramarginal, Postcentral, Precuneus, combinations thereof, and the like), temporal lobe (either the entire temporal lobe or portions thereof including but not limited to e.g., Superior Temporal, Middle Temporal, Inferior Temporal, Banks of the Superior Temporal Sulcus, Fusiform, Transverse Temporal, Entorhinal, Temporal Pole, Parahippocampal, combinations thereof, and the like) and occipital lobe (either the entire occipital lobe or portions thereof including but not limited to e.g., Lateral Occipital, Lingual, Cuneus, Pericalcarine, combinations thereof, and the like).

In some instances, one or more brain structures or a particular area within a brain structure may be targeted including but not limited to e.g., Hindbrain structures (e.g., Myelencephalon structures (e.g., Medulla oblongata, Medullary pyramids, Olivary body, Inferior olivary nucleus, Respiratory center, Cuneate nucleus, Gracile nucleus, Intercalated nucleus, Medullary cranial nerve nuclei, Inferior salivatory nucleus, Nucleus ambiguous, Dorsal nucleus of vagus nerve, Hypoglossal nucleus, Solitary nucleus, etc.), Metencephalon structures (e.g., Pons, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centres, Pneumotaxic centre, Apneustic centre, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Fourth ventricle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, etc.)), Midbrain structures (e.g., Tectum, Corpora quadrigemina, inferior colliculi, superior colliculi, Pretectum, Tegmentum, Periaqueductal gray, Parabrachial area, Medial parabrachial nucleus, Lateral parabrachial nucleus, Subparabrachial nucleus (Kölliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Crus cerebri, Mesencephalic cranial nerve nuclei, Oculomotor nucleus (III), Trochlear nucleus (IV), Mesencephalic duct (cerebral aqueduct, aqueduct of Sylvius), etc.), Forebrain structures (e.g., Diencephalon, Epithalamus structures (e.g., Pineal body, Habenular nuclei, Stria medullares, Taenia thalami, etc.) Third ventricle, Thalamus structures (e.g., Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, etc.), Hypothalamus structures (e.g., Anterior, Medial area, Parts of preoptic area, Medial preoptic nucleus, Suprachiasmatic nucleus, Paraventricular nucleus, Supraoptic nucleus (mainly), Anterior hypothalamic nucleus, Lateral area, Parts of preoptic area, Lateral preoptic nucleus, Anterior part of Lateral nucleus, Part of supraoptic nucleus, Other nuclei of preoptic area, median preoptic nucleus, periventricular preoptic nucleus, Tuberal, Medial area, Dorsomedial hypothalamic nucleus, Ventromedial nucleus, Arcuate nucleus, Lateral area, Tuberal part of Lateral nucleus, Lateral tuberal nuclei, Posterior, Medial area, Mammillary nuclei (part of mammillary bodies), Posterior nucleus, Lateral area, Posterior part of Lateral nucleus, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, etc.), Subthalamus structures (e.g., Thalamic nucleus, Zona incerta, etc.), Pituitary gland structures (e.g., neurohypophysis, Pars intermedia (Intermediate Lobe), adenohypophysis, etc.), Telencephalon structures, white matter structures (e.g., Corona radiata, Internal capsule, External capsule, Extreme capsule, Arcuate fasciculus, Uncinate fasciculus, Perforant Path, etc.), Subcortical structures (e.g., Hippocampus (Medial Temporal Lobe), Dentate gyrus, Cornu ammonis (CA fields), Cornu ammonis area 1, Cornu ammonis area 2, Cornu ammonis area 3, Cornu ammonis area 4, Amygdala (limbic system) (limbic lobe), Central nucleus (autonomic nervous system), Medial nucleus (accessory olfactory system), Cortical and basomedial nuclei (main olfactory system), Lateral[disambiguation needed] and basolateral nuclei (frontotemporal cortical system), Claustrum, Basal ganglia, Striatum, Dorsal striatum (aka neostriatum), Putamen, Caudate nucleus, Ventral striatum, Nucleus accumbens, Olfactory tubercle, Globus pallidus (forms nucleus lentiformis with putamen), Subthalamic nucleus, Basal forebrain, Anterior perforated substance, Substantia innominata, Nucleus basalis, Diagonal band of Broca, Medial septal nuclei, etc.), Rhinencephalon structures (e.g., Olfactory bulb, Piriform cortex, Anterior olfactory nucleus, Olfactory tract, Anterior commissure, Uncus, etc.), Cerebral cortex structures (e.g., Frontal lobe, Cortex, Primary motor cortex (Precentral gyrus, M1), Supplementary motor cortex, Premotor cortex, Prefrontal cortex, Gyri, Superior frontal gyrus, Middle frontal gyrus, Inferior frontal gyrus, Brodmann areas: 4, 6, 8, 9, 10, 11, 12, 24, 25, 32, 33, 44, 45, 46, 47, Parietal lobe, Cortex, Primary somatosensory cortex (S1), Secondary somatosensory cortex (S2), Posterior parietal cortex, Gyri, Postcentral gyrus (Primary somesthetic area), Other, Precuneus, Brodmann areas 1, 2, 3 (Primary somesthetic area); 5, 7, 23, 26, 29, 31, 39, 40, Occipital lobe, Cortex, Primary visual cortex (V1), V2, V3, V4, V5/MT, Gyri, Lateral occipital gyrus, Cuneus, Brodmann areas 17 (V1, primary visual cortex); 18, 19, Temporal lobe, Cortex, Primary auditory cortex (A1), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas: 9, 20, 21, 22, 27, 34, 35, 36, 37, 38, 41, 42, Medial superior temporal area (MST), Insular cortex, Cingulate cortex, Anterior cingulate, Posterior cingulate, Retrosplenial cortex, Indusium griseum, Subgenual area 25, Brodmann areas 23, 24; 26, 29, 30 (retrosplenial areas); 31, 32, etc.)).

In some instances, one or more neural pathways or a particular portion of a neural pathway may be targeted including but not limited to e.g., neural pathways of those brain lobes and structures described above, Superior Longitudinal Fasciculus, Arcuate fasciculus, Cerebral peduncle, Corpus callosum, Pyramidal or corticospinal tract, Major dopamine pathways dopamine system, Mesocortical pathway, Mesolimbic pathway, Nigrostriatal pathway, Tuberoinfundibular pathway, Serotonin Pathways serotonin system, Raphe Nuclei, Norepinephrine Pathways, Locus coeruleus, etc.

In some instances, diseased and/or disease causing tissue may be targeted. Any disease and/or disease causing tissue may be targeted according to the instant methods including but not limited to e.g., diseased neural tissue, solid tumors, neural or CNS tumors, and the like. As used herein, a "CNS tumor" or "tumor of the CNS" refers to a primary or malignant tumor of the CNS of a subject, e.g., the aberrant growth of cells within the CNS. The aberrantly growing cells of the CNS may be native to the CNS or derived from other tissues.

In some instances, targted tumors may include but are not limited to e.g., gliomas e.g., glioblastoma multiforme (GBM), astrocytoma, including fibrillary (diffuse) astrocytoma, pilocytic astrocytoma, pleomorphic xanthoastrocytoma, and brain stem glioma, oligodendroglioma, ependymoma and related paraventricular mass lesions, neuronal tumors, poorly differentiated neoplasms, including medulloblastoma, other parenchymal tumors, including primary brain lymphoma, germ cell tumors, pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma).

Diseased neural tissues that may be targeted include but are not limited to e.g., neural tissue disease due to one or more of meningitis, encephalitis, multiple sclerosis (MS), stroke, brain tumors, epilepsy, Alzheimer's disease, AIDS related dementia, Parkinson's disease.

The methods of the instant disclosure may be applied to delivery of therapeutic agents to a targeted region of a subject, including e.g., the brain of a subject. Agents of interest include, without limitation, proteins, drugs, antibodies, antibody fragments, immunotoxins, chemical compounds, protein fragments, viruses, nucleic acids (e.g., (expression vectors, gene therapy vectors, small hairpin nucleic acids, interfering nucleic acids, aptamers, etc.) and toxins.

In some instances, the methods of the instant disclosure may include the delivery of a gene therapy vector including but not limited to e.g., delivery of an adenovirus (AAV) gene therapy vector.

In some instances, the methods of the instant disclosure may include the delivery of cell therapies. As used herein, the term "cell therapy" generally includes therapies derived from the delivery of living cells, whether or not recombinantly engineered, to a subject. Useful cells delivered in cell therapies include but are not limited to e.g., stem cells (e.g., adult stem cells (e.g., mesenchymal stem cells, adipose stem cells, muscle satellite cells, neural stem cells, liver stem cells, hematopoietic stem cells, etc.), embryonic stem cells, induced pluripotent stem cells (iPS), etc.) and terminally or partially differentiated cell types. Useful cell types also include e.g., engineered immune cell type such as e.g., engineered T cells.

Therapeutic agents, including cellular therapeutics, are administered according to the methods described herein at any effective concentration. An effective concentration of a therapeutic agent is one that results in decreasing or increasing a particular pharmacological effect. One skilled in the art would know how to determine effective concentration according to methods known in the art, as well as provided herein.

Dosages of the therapeutic agents will depend upon the disease or condition to be treated, and the individual subject's status (e.g., species, weight, disease state, etc.) Dosages will also depend upon how the agents are being administered where precise targeted delivery may in some instances allow for an effective dose that is smaller than a systemic dose or even a dose delivered to the general area (e.g., the brain generally) but not specifically targeted. Effective dosages are known in the art or can be determined empirically. Furthermore, the dosage can be adjusted according to the typical dosage for the specific disease or condition to be treated. Often a single dose can be sufficient; however, the dose can be repeated if desirable. The dosage should not be so large as to cause adverse side effects. Generally, the dosage will vary with the age, condition, sex and extent of the disease in the patient and can be determined by one of skill in the art according to routine methods (see e.g., Remington's Pharmaceutical Sciences). The dosage can also be adjusted by the individual physician in the event of any complication.

The therapeutic agent can typically include an effective amount of the respective agent in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

For the delivery of a therapeutic agent according to the instant methods, generally a targeting device will be targeted to a desired area as described above using a targeting guide. Following targeting, the targeting guide may be removed, removing the style(s) from the channel(s) of the targeted device and replacing one or more styles with a therapeutic delivery device. Once in place within the channel of the targeting device the therapeutic delivery device may be deployed and/or activated, e.g., to cause the therapeutic to be released, injected, dispersed, etc. Following delivery, the delivery device may be removed or may be left in place, e.g., where a dosage protocol calls for repeated dosing. In some instances, following one or more doses, the targeting device may remain in place and targeting may be checked, and adjusted if necessary, using a targeting guide prior to subsequent dosing.

The subject methods are not limited to therapeutic delivery and also include targeted surgical applications such as e.g., targeted cell ablation, targeted electrical stimulation, etc. In some instances, a targeting device may be applied as described herein to direct a probe, e.g., an ablation probe, an electrode, etc., to a desired area of the subject and the probe may be activated to provide for targeted ablation (e.g., targeted neuroablation), targeted stimulation (e.g., targeted neurostimulation), etc.

The subject methods are not limited to therapeutic delivery and surgical applications and also include targeted diagnostics. In some instances, a diagnostic device may be deployed through a targeting device according to the methods as described herein for precise diagnostic protocols. For example, in some instances, a biopsy collection device (e.g., a fine needle aspirate device) may be applied using a targeting system and method described herein to precisely target and collect a desired biopsy. In some instances, a diagnostic imaging instrument, e.g., an endoscope, may be applied using a targeting system and method described herein to precisely target and collect a desired image for diagnostic purposes. Useful endoscopes include but are not limited to e.g., those commercially available from Medigus Ltd (Omer, Israel) including but not limited to e.g., the micro ScoutCam endoscope cameras.

Devices and Systems

The instant disclosure provides devices and systems useful in methods for targeting a biomedical device or therapy to a desired area of a subject, including devices and systems useful in practicing those methods as described herein. Devices described herein include trajectory guides, adjustable turret targeting systems, and components thereof. In some instances, the described systems may include imaging devices, biomedical systems, etc. The described devices, systems and components thereof may, as appropriate, be manually controlled or fully or partially automated as described in more detail herein.

In some instances, the herein described devices, or components thereof, may serve as a holder for therapeutic administration devices including but not limited to e.g., drug delivery devices, viral vector delivery devices, nanoparticle delivery devices, cell administration delivery devices, cell delivery devices, and the like.

The instant disclosure includes trajectory guides. Trajectory guides of the instant disclosure will generally include at least one MRI-visible style attached to base, where imaging the MRI-visible style allows for the determination of the trajectory of a device into which the MRI-visible style is placed. MRI-visible styles of a trajectory guide may be flexible, rigid or semi-rigid, depending on the particular context. A MRI visible style may, in some instances, be constructed from a tube, including flexible tubes and rigid tubing, and may have a cap at the distal end and be open or closed at the proximal end attached to the base. A cavity or lumen within the MRI-visible style may facilitate filling the MRI-visible style with a contrast agent. In some instances, other configurations of an MRI-visible style may be employed including e.g., where the MRI-visible style is constructed of an MRI-visible material, including e.g., a material embedded with an MRI-contrast agent, with or without a coating.

Any convenient MRI contrast agent may find use in MRI-styles described herein including but not limited solid (e.g., particle), liquid and gel contrast agents. Accordingly, depending on the application, e.g., whether the style is rigid or flexible, contrast agents used may vary and may include but are not limited to e.g., Gadolinium(III) containing MRI contrast agents (e.g., gadobenate, gadobutrol, gadocoletic acid, gadodiamide, gadofosveset, gadomelitol, gadomer 17, gadopentetate, gadopentetic acid dimeglumine, gadoterate, gadoteridol, gadoversetamide, gadoxetate, gadoxeticacid, etc.), iron oxide containing MRI contrast agents (e.g., Feridex, Resovist, Sinerem, Lumirem, PEG-fero (a.k.a., Feruglose), etc.), iron platinum containing MRI contrast agents (e.g., iron-platinum-based nanoparticles), manganese containing MRI contrast agents (e.g., Mn-based nanoparticles), and the like.

Referring now to FIG. 6A, in one embodiment, a trajectory guide of the instant disclosure may include a single MRI-visible style (600) attached to a base (601). The base of the trajectory guide will generally have a surface, e.g., a flat surface or an essentially flat surface, to which one or more MRI-visible styles at attached. In some instances, the surface may contain one or more holes or one or more wells into which the one or more styles may be inserted. In the embodiment depicted, the MRI-visible style is constructed of a tube having a cap at the distal end (602), allowing the tube to be filled with a contrast agent. As can be seen in the cross-sectional depiction in FIG. 6B, the MRI-visible style (600) has an internal lumen (603) which may be filled, e.g., with an MRI-visible contrast agent. In some instances, the base may include a void or cavity (604) that is contiguous or confluent with the lumen of the MRI-visible style (603), e.g., by a direct connection of the void and lumen or by means of an intermediate connection such as, e.g., a passage (605) as depicted in FIG. 6B.

In some instances, trajectory guides of the instant disclosure may include a plurality of MRI-visible styles, e.g., as present in the embodiment depicted in FIG. 7A, which includes a base (700) and seven MRI-visible styles (701) attached orthogonally to the base. The actual number of MRI-visible styles may vary depending on a number of factors including but not limited to e.g., the overall size of the trajectory guide, the dimensions of the targeting device to which the trajectory guide is made compatible, the requirements of the desired targeting application and the like. As such, the number of MRI-visible styles of a targeting guide may range from 1 to 64 or more including but not limited to e.g., 1 to 64, 1 to 55, 1 to 50, 1 to 45, 1 to 40, 1 to 36, 1 to 30, 1 to 24, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 2 to 64, 2 to 55, 2 to 50, 2 to 45, 2 to 40, 2 to 36, 2 to 30, 2 to 24, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 2 to 7, 2 to 6, 2 to 5, 2 to 4, 5 to 64, 5 to 55, 5 to 50, 5 to 45, 5 to 40, 5 to 36, 5 to 30, 5 to 24, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, 10 to 64, 10 to 55, 10 to 50, 10 to 45, 10 to 40, 10 to 36, 10 to 30, 10 to 24, 10 to 20, 10 to 19, 10 to 18, 10 to 17, 10 to 16, 10 to 15, 10 to 14, 10 to 13, 10 to 12, 12, 11, 10, 9, 8, 7, 6, 5, 4, 3, 2, 1, etc.

The trajectory guide embodiment of FIG. 7A, is further depicted in FIG. 7B, but with the closeable cap (703) removed. Removal of the cap (703) may allow access to a cavity in the base (704) allowing for the filling and/or replacing of contrast agent. The cap may be affixed to the base by any suitable means including e.g., a compression fitting or, as depicted compatible threading in the cap (705) and base (706). Furthermore, the trajectory guide may or may not make use of one or more gaskets or O-rings, such as e.g., the gasket (707) depicted in FIG. 7B that provides a seal between the cap and base to prevent leakage of the contrast agent. In some instances, component parts of a trajectory guide may be machined such that a gaskets and/or O-rings are not necessary.

In some instances, the trajectory guide may not include a removable cap. For example, in some embodiments the trajectory guide may be configured such that access to one or more lumens of one or more MRI-visible styles is unnecessary and such configurations may not include a removable cap or may not otherwise provide access to the lumen(s) of the MRI-visible styles. In some instances, where an MRI-visible style does not include a removable cap on the base, access to the lumen of the MRI-visible style(s) may be achieved through one or more removable caps on the distal end of the MRI-visible styles. Depending on the particular configuration and the MRI contrast agent employed, in some instances, the contrast agent may need to be periodically replaced and in other instances the MRI-contrast agent may not need to be replaced.

The MRI-visible style(s) of a trajectory guide may vary in size along various dimensions, including e.g., length, width, diameter, etc., and may, in some instances, be configured and/or dimensioned for insertion into a channel of an adjustable turret of a targeting device, as described in more detail below. For example, the length of the MRI-style, as measured from the base of the targeting guide to the distal end, may be essentially the same as the length of the channel into which it is inserted or shorter. The gauge of the MRI-style may be dimensioned such that the style may be inserted into a channel an adjustable turret of a targeting device to allow for determining the trajectory of the channel. For example, the gauge of the style may be sufficiently large to conform to the trajectory of the channel but also sufficiently small to allow for easy insertion of the style into the channel.

As such, the dimensions of the MRI-visible style(s) of a trajectory guide may vary. In some instances, the length of the MRI-visible style(s) may range from 1 cm or less to 10 cm or more including but not limited to e.g., 1 cm to 10 cm, 2 cm to 10 cm, 3 cm to 10 cm, 4 cm to 10 cm, 5 cm to 10 cm, 1 cm to 9 cm, 1 cm to 8 cm, 1 cm to 7 cm, 1 cm to 6 cm, 1 cm to 5 cm, 2 cm to 5 cm, 3 cm to 6 cm, 2 cm to 4 cm, 3 cm to 5 cm, 1 cm, 2 cm, 3 cm, 4 cm, 5 cm, and the like. In some instances, the gauge of the MRI-visible style(s) may range from 42 gauge or less to 6 gauge or more, according to British Standard Wire Gauge (SWG) measurements, including but not limited to e.g., 42 gauge, 41 gauge, 40 gauge, 39 gauge, 38 gauge, 37 gauge, 36 gauge, 35 gauge, 34 gauge, 33 gauge, 32 gauge, 31 gauge, 30 gauge, 29 gauge, 28 gauge, 27 gauge, 26 gauge, 25 gauge, 24 gauge, 23 gauge, 22 gauge, 21 gauge, 20 gauge, 19 gauge, 18 gauge, 17 gauge, 16 gauge, 15 gauge, 14 gauge, 13 gauge, 12 gauge, 11 gauge, 10 gauge, 9 gauge, 8 gauge, 7 gauge, 6 gauge, and the like.

As described above, the trajectory guide and/or the MRI-visible style(s) thereof may be dimensioned to be compatible with an adjustable turret of the targeting device as described herein. Any portion or component of the trajectory guide and/or MRI-visible style(s) may be dimensioned to be compatible with an adjustable turret including, e.g., the diameter or gauge of the style(s) may be dimensioned to be compatible with the channel(s) of the adjustable turret. In some instances, the channel(s) and style(s) are configured to be compatible in length. In some instances, the base of the trajectory guide is configured to be compatible with a surface of the adjustable turret having the openings to the channels into which the style(s) are inserted. The turret and the trajectory guide need not be compatibly dimensioned in all aspects and, in some instances may differ, e.g., differ in length of the styles and the length of the channels, differ in the size of the flat surface of the base of the trajectory guide and the flat surface of the turret having the channel holes, etc. Provided it does not negatively impact the functioning of the device any corresponding components of the turret and the trajectory guide may or may not be compatible dimensioned.

Aspects of the instant disclosure include an adjustable turret of a targeting device. In general, adjustable turrets of the instant disclosure will include a distal end and rounded end, e.g., a spherical or essentially spherical end. Adjustable turrets as described will also generally include at least one channel running from the distal end to the rounded end allowing for insertion of the style(s) of a trajectory guide for targeting and insertion of one or more biomedical devices for various purposes including e.g., agent delivery, device delivery, imaging, etc. In some instances, an adjustable turret may have a single channel. In other instances, an adjustable turret may have a plurality of channels. As such, the number of channels in an adjustable turret may range, e.g., from 1 to 64 or more including but not limited to e.g., 1 to 64, 1 to 55, 1 to 50, 1 to 45, 1 to 40, 1 to 36, 1 to 30, 1 to 24, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 2 to 64, 2 to 55, 2 to 50, 2 to 45, 2 to 40, 2 to 36, 2 to 30, 2 to 24, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 2 to 7, 2 to 6, 2 to 5, 2 to 4, 5 to 64, 5 to 55, 5 to 50, 5 to 45, 5 to 40, 5 to 36, 5 to 30, 5 to 24, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, 10 to 64, 10 to 55, 10 to 50, 10 to 45, 10 to 40, 10 to 36, 10 to 30, 10 to 24, 10 to 20, 10 to 19, 10 to 18, 10 to 17, 10 to 16, 10 to 15, 10 to 14, 10 to 13, 10 to 12, 12, 11, 10, 9, 8, 7, 6, 5, 4, 3, 2, 1, etc.

The size of the rounded end of the adjustable turret may vary. For example, in some instances, an essentially spherical rounded end of an adjustable turret may range from 1 cm to 10 cm or more in diameter including but not limited to e.g., from 1 cm to 10 cm, from 2 cm to 10 cm, from 3 cm to 10 cm, from 4 cm to 10 cm, from 5 cm to 10 cm, from 6 cm to 10 cm, from 7 cm to 10 cm, from 8 cm to 10 cm, from 9 cm to 10 cm, from 1 cm to 9 cm, from 1 cm to 8 cm, from 1 cm to 7 cm, from 1 cm to 6 cm, from 1 cm to 5 cm, from 1 cm to 4 cm, from 1 cm to 3 cm, from 1 cm to 2 cm, etc. Similarly, the length, along the long axis, of the adjustable turret will also vary where such length will also correspond or nearly correspond to the length of one or more channels of the turret. In some instances, the length of the adjustable turret may range from 1 cm or less to 10 cm or more including but not limited to e.g., from 1 cm to 10 cm, from 2 cm to 10 cm, from 3 cm to 10 cm, from 4 cm to 10 cm, from 5 cm to 10 cm, from 6 cm to 10 cm, from 7 cm to 10 cm, from 8 cm to 10 cm, from 9 cm to 10 cm, from 1 cm to 9 cm, from 1 cm to 8 cm, from 1 cm to 7 cm, from 1 cm to 6 cm, from 1 cm to 5 cm, from 1 cm to 4 cm, from 1 cm to 3 cm, from 1 cm to 2 cm, from 2 cm to 9 cm, from 2 cm to 8 cm, from 2 cm to 7 cm, from 2 cm to 6 cm, from 2 cm to 5 cm, from 2 cm to 4 cm, from 3 cm to 9 cm, from 3 cm to 8 cm, from 3 cm to 7 cm, from 3 cm to 6 cm, from 3 cm to 5 cm, from 3 cm to 4 cm, etc. The difference in size of the distal end of the turret and the rounded end of the turret will also vary. For example, where the rounded end is essentially spherical and the distal end is essentially cylindrical, the ratio between the largest diameter at the spherical end and the diameter of the cylinder may range from more than 10:1 to than 1:1 including but not limited to e.g., 10:1, 9:1, 8:1, 7:1, 6:1, 5:1, 4:1, 3:1, 2:1, and the like.

An adjustable turret may or may not be configured to have the same number of channels as a corresponding trajectory guide. In addition, an adjustable turret may or may not be configured such that the channel(s) of the trajectory guide are in the same configuration as the style(s) of the trajectory guide. Accordingly, all, some or any one channel of an adjustable turret may be symmetrically or asymmetrically arranged with respect to the geometric center of the distal surface of the trajectory guide, i.e., the surface having the opening(s) to the channel(s). Accordingly, all, some or any one style of a trajectory guide may be symmetrically or asymmetrically arranged with respect to the geometric center of the surface to which they are attached, i.e., the surface of the base to which they are attached. In addition, in some instances, the arrangement of channels in an adjustable turret and the arrangement of styles in a corresponding trajectory guide may be configured to be compatible, whether or not the turret contains a channel or channels which are asymmetrically arranged or the trajectory guide contains a style or styles which are asymmetrically arranged.

Figure 4A:
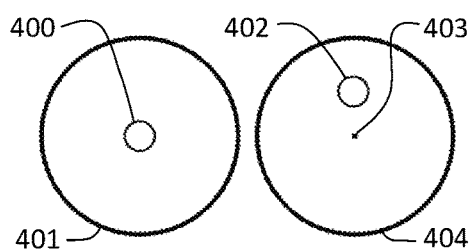
FIGS. 4A-4F provide exemplary arrangements of channels within a turret or styles of a trajectory guide as described herein.

Any convenient arrangement of channels and/or styles may find use in the methods and devices of the subject disclosure. For simplicity various non-limiting arrangements will be described below in reference to the channels of an adjustable turret; however, it will be readily understood that such arrangement may be equally applied to the styles of a trajectory guide. In embodiments having a single channel, the channel may be arranged in the turret at any convenient location including, e.g., as depicted in FIG. 4A, the channel (400) may be positioned at the geometric center of the turret (401), i.e., coaxial with the long axis of the turret, or the channel (402) may be positioned away from the geometric center (403) of the turret (404), i.e., not coaxial with the long axis of the turret.

Figure 4B:
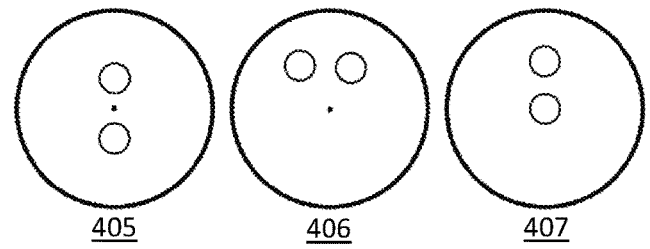
Figure 4C:
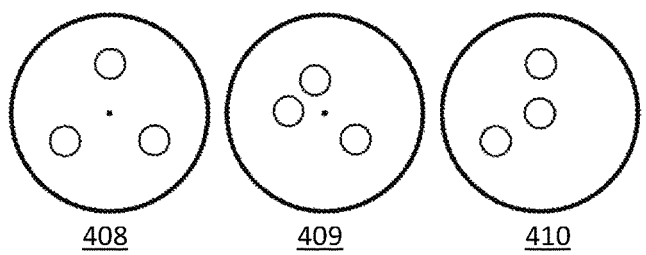

As depicted in the non-limiting examples of FIG. 4B, in embodiments having a plurality of channels, two channels of the plurality may be positioned symmetrically with respect to the geometric center of the turret (405), or may be equidistant from the geometric center of the turret but offset from the center (406), or one of the two channels may be positioned at the center of the turret (407). As depicted in the non-limiting examples of FIG. 4C, in embodiments having three or more channels, three of the channels may be positioned symmetrically about the geometric center of the turret (408), or asymmetrically about the geometric center of the turret (409), or one of the three may be positioned at the center of the turret (410).

Figure 4D:
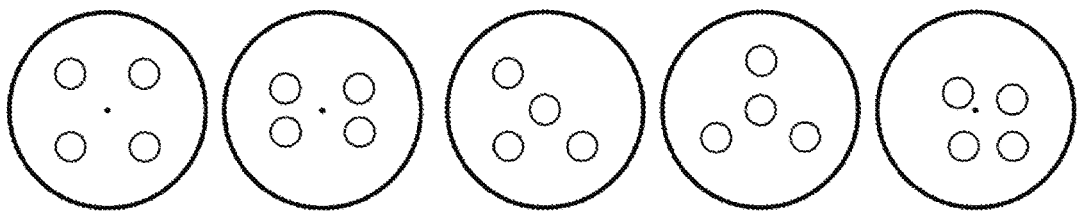
Figure 4E:
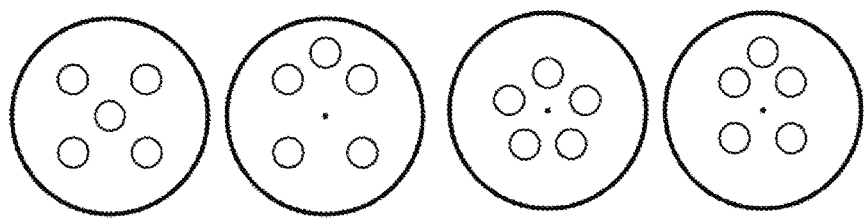
Figure 4F:
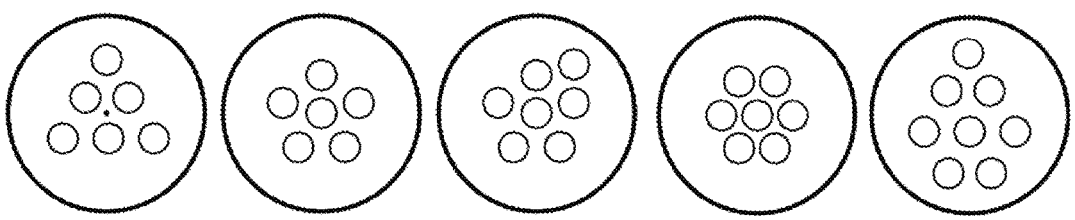

Further exemplary depictions of possible arrangements of channels are provided for turrets having four channels (FIG. 4D), five channels (FIG. 4E) and six or more channels (FIG. 5F). It will be understood, that the examples provided are not intended to be limiting as to the arrangement of channels, and correspondingly, to the arrangement of styles. It will be understood that such arrangements may vary greatly and be configured and reconfigured according to the particular desired use of the subject targeting system. Furthermore, although described above with regard to the geometric center of the turret, the symmetry of the arrangement of channels and/or styles may be referred to relative to any other component of aspect thereof of the system including e.g., another channel or channels of the system, another style or styles of the system, any axis, plane or center of a surface of a component of the system, etc.

The channel(s) of the adjustable turret and/or the style(s) of the trajectory guide may or may not be arranged parallel to the long axis of the turret or guide, respectively. Similarly, the channels of an adjustable turret having a plurality of channels may or may not be arranged parallel to one another and/or the styles of a trajectory guide having a plurality of styles may or may not be arranged parallel to one another. In some instances, e.g., as depicted in FIG. 5A, the channels (500) of an adjustable turret (501) may be configured parallel to the long axis of the adjustable turret such that their trajectories remain essentially parallel. In some instances, e.g., as depicted in FIG. 5B, the channels (502) of an adjustable turret (503) may be configured such that they are not parallel, either to the long axis of the adjustable turret or one another or both, and their trajectories are correspondingly not parallel.

In some instances, a channel that is arranged within an adjustable turret not parallel to the long axis of the adjustable turret may be referred to as flared and/or having a flared trajectory. As used herein the term "flared" will generally refer to a trajectory, e.g., of a channel or style, that is not parallel with the long axis of the device to which it is attached and having an acute angle relative to the long axis. Components of the subject devices may be flared to various magnitudes, e.g., as measured by the angle of deviation from the long axis of the device. For example in some instances a component, e.g., a channel or a style, may be flared by 1 degree or more, including but not limited to e.g., 2 degrees or more, 3 degrees or more, 4 degrees or more, 5 degrees or more, 6 degrees or more, 7 degrees or more, 8 degrees or more, 9 degrees or more, 10 degrees or more, 15 degrees or more, 20 degrees or more, etc., but generally not flared more than about 40 degrees. A device may but need not have only parallel or flared components and, as such, in some instances parallel and flared components may be combined.

Turning now to the adjustable turret depicted in FIG. 8A. In the depicted embodiment, the adjustable turret has essentially a spherical portion (800) and a cylindrical portion (801) and a plurality of channels (802) running from the flat surface on the distal end (803) of the cylindrical portion to the opposite end on the spherical portion. The rounded portion of the adjustable turret may or may not have a flat surface corresponding to the point at which the channels exit the turret. For example, as depicted in FIG. 8B, in some instances, a spherical end (804) of an adjustable turret has a flat surface (805) at that contains the channel openings (806).

In some instances, the adjustable turret may include one or more means for securing items inserted into one or more of the channels. For example, as depicted in the embodiment of FIGS. 8A and 8B, an adjustable turret may include one or more screws (807) and corresponding screw holes that extend into one or more channels such that, when tightened, the screws secure within the channel any device or other component that has been inserted into the channel. Correspondingly, e.g., when the device or other component is to be removed, the screw or other fastener may be loosened allowing removal.

In some instances, all or a portion of the adjustable turret may be made to be MRI-visible, e.g., by embedding a contrast agent in the adjustable turret, by filling a cavity of the adjustable turret with a contrast agent, etc. In some instances, where all or a portion of the adjustable turret is made to be MRI-visible the MRI-visible portion of the adjustable turret may serve the targeting purposes of the herein described MRI-visible style. For example, where the entire adjustable turret is made to be MRI-visible, visualizing the turret with an MRI device may allow for a determination of trajectory and/or trajectory adjustments. In another example, where the adjustable turret includes an MRI-visible portion or an embedded MRI-visible element or a cavity filled with a contrast agent that is parallel with one or more channels of the adjustable turret, the MRI-visible portion or embedded MRI-visible element or cavity filled with contrast agent may allow for a determination of trajectory and/or trajectory adjustments. In one embodiment, an adjustable turret as described herein may include an MRI-visible portion along the long-axis of the adjustable turret parallel with and/or adjacent to one or more channels of the adjustable turret.

MRI-visible portions along the long-axis of an adjustable turret may vary in length and may e.g., run the entire length of the adjustable turret, less that the entire length of the adjustable turret, more than half of the length of the adjustable turret, about half of the length of the adjustable turret, less than half the length of the adjustable turret, about 100% of the length of the adjustable turret, from about 90% to about 100% of the length of the adjustable turret, from about 50% to about 100% of the length of the adjustable turret, from about 75% to about 100% of the length of the adjustable turret, about 50% of the length of the adjustable turret, from about 10% to about 50% of the length of the adjustable turret, from about 25% to about 50% of the length of the adjustable turret, from about 25% to about 75% of the length of the adjustable turret, from about 10% to about 90% of the length of the adjustable turret, about 10% of the length of the adjustable turret, and the like.

In some instances, an adjustable turret of the instant disclosure may include an MRI-visible band. By "MRI-visible band", as used herein, is meant a circular or semi-circular or elliptical strip of MRI-visible material (including e.g., a cavity filled with a contrast agent) that encircles the circumference or a portion thereof (including e.g., half of, or a majority thereof, etc.) of the adjustable turret. An MRI-visible band may be arranged perpendicular to the long-axis of the adjustable turret. An MRI-visible band may be placed at any position along the long-axis of the adjustable turret. An MRI-visible band may server various functions in determining the position of the adjustable turret or a channel thereof or a device inserted into a channel of the adjustable turret. For example, in some instances, visualization of an MRI-visible band using an MRI imager allows for performing depth calculations related to the position of the adjustable turret or a channel thereof or a device inserted into a channel of the adjustable turret.

As an illustration, in one embodiment, a device is inserted into a channel of an adjustable turret having an MRI-visible band and one end of the device or a specific position along the length of the device is aligned with the band. Next the adjustable turret is MRI imaged and a depth calculation is performed involving a measurement of the distance between a target area and the MRI-visible band. Such a depth calculation may allow a user to determine how much of a device to insert into a channel of an adjustable turret such that the device reaches the desired target area. Other configurations using an MRI-visible band for depth calculation and other purposes will be readily apparent.

The adjustable turret of the instant devices and systems may be configured to be compatible with other components, e.g., for securing the adjustable turret between adjustments and/or securing the adjustable turret to a subject. In some instances, an adjustable turret may be part of a multi-component targeting device, e.g., as depicted in FIG. 9A. In the embodiment of FIG. 9A, the multi-component targeting device has an adjustable turret (900), e.g., as described above, a base component (901) and a locking component (902). As can be seen in FIG. 9B, which provides an exploded version of the embodiment depicted in FIG. 9A, the base component (903) may be configured to receive the rounded end of the adjustable turret (904), e.g., the rounded end of the adjustable turret may "snap into" the base component.

The locking component (905) may be configured to allow the distal end, e.g., the cylindrical end, of the adjustable turret (906) to pass freely through the inner diameter of the locking component. The inner diameter of the locking component will generally be configured to be smaller than the diameter of the rounded end of the adjustable turret (904). Such a configuration of relative sizes will generally allow for the locking component to compress the rounded end of the adjustable turret when the multi-component device is assembled, e.g., by means of compatible threading on the exterior surface of the base (907) and interior surface threading on the locking component (908).

Accordingly, by turning the locking collar one direction, i.e., tightening the locking collar, the round end of the turret is compressed between the locking collar and the base and adjustment of the turret is restricted. Turning the locking collar the opposite direction, i.e., loosening the locking collar, the compression of the round end of the turret between the locking collar and the base is released and adjustment of the turret is possible.

The locking collar need not necessarily contact the round end of the turret to effectively compress the round end of the turret and restrict adjustment. For example, in some instances, the locking collar is configured such that the locking collar contacts only the based and does not contact the round end of the adjustable turret. In such instances, turning the locking collar may compress the base, including but not limited to e.g., a plurality of annular walls of the base as described in more detail below, into the round end of the turret without directly contacting the round end of the turret. As such, in some instances, the smallest inner diameter of the locking collar may be larger than the largest diameter of the round end of the adjustable turret. However, depending on the configuration of the base, including but not limited to e.g., the configuration of the plurality of annular walls of the base, the smallest inner diameter of the locking collar need not necessarily be larger than the largest diameter of the round end of the adjustable turret.

In some instances, the locking collar is configured such that, when the components of the systems are engaged, the locking collar does not or only minimally impacts the maximum turret angle adjustment. Accordingly, even when the components of the device are assembled, significant angle adjustment near the otherwise maximum adjustment of the turret is possible.

In some embodiments, the locking collar may have a lower end that engages the base and an upper end opposite the base where the upper end has a diameter sufficiently large such that, at maximum angle adjustments, the turret does not contact the upper end. For example, as illustrated in FIG. 14C which shows a cutaway of one embodiment of the multicomponent device, the locking collar (1400) has a lower end (1404) that engages the base (1405) and an upper end (1401) that is essentially a ring with an inner diameter (1402) that matches or exceeds the maximum angle adjustment "X" of the turret (1403). Thus, in some instances, the upper end of the locking collar will have a diameter that is larger than the diameter of the lower end of the locking collar.

In some instances, the locking collar may include a flat surface surrounding the upper ring shaped end that is configured for turning the locking collar, i.e., tightening and loosening the locking collar. For example, in the embodiment depicted in FIG. 14A, the locking collar has a flat surface (1406) configured for turning the locking collar. Such flat surfaces may or may not be textured. For example, in some instances the flat surface of the locking collar may be knurled to facilitate grip on the locking collar to facilitate turning the locking collar. Texturing and/or knurling is not limited to the flat surface of the locking collar as described and, in some instances, any other surface of any component of the device may be correspondingly textured and/or knurled to facilitate grip where appropriate.

The individual components of the systems may be configured such that one or more components, including all of the components of the assembled system are substantially ex vivo. In some instances, the base is attached to the subject such that the base remains substantially and/or completely ex vivo. In some instances, the turret is attached to the subject such that the turret remains substantially and/or completely ex vivo. For example, as depicted in FIGS. 14A, and 14B which provides a 90 degree rotated view of the embodiment of FIG. 14A, the assembled unit, attached to a subject at the base (1407), remains on the outside of the subject. In some instances, the base is attached to the subject and the assembled unit is configured such that the rounded end of the turret is positioned substantially flush with the surface of the subject to which the base is attached. Where the turret has a flat surface on the rounded end which contains the channel opening(s) and when the turret is aligned perpendicular to the base, the plane of the flat surface will be substantially parallel or substantially coplanar with the surface of the base that interfaces with the subject.

In instances herein where a component or the system is described as completely or substantially ex vivo such description excludes any fastener(s) that may be inserted into the subject to attach the component or system. Likewise, descriptions of a component or the system being substantially or completely ex vivo will exclude situations where the component of system is normally ex vivo but minimally breaks the plane separating ex vivo space from in vivo space in certain adjustment positions. For example, in some instances, when a maximal angle adjustment is applied to the turret a small portion of the turret may extend toward to the subject beyond the base (see e.g., FIG. 14A and FIG. 14B). However, as described herein such instances are still considered to be substantially and/or completely ex vivo.

In comparison, the base of a targeting system may be configured to extend into the subject and substantially break the plane separating ex vivo from in vivo. A depiction of such a situation is provide in FIG. 15A and the corresponding cross section of FIG. 15B. This situation includes a turret (1500), a locking collar (1501) and a base (1502) wherein the base includes a treaded portion that, when attached to a tissue surface of the subject, extends into the subject (1503). Accordingly, the instantly described situation is not completely or substantially ex vivo as a portion of the base is positioned in vivo. A consequence of this configuration, which can be seen in the cross section of FIG. 15B, is that at angle adjustments approaching maximum ("MAX") the trajectory (1504) of one or more channels of the turret can be blocked by the in vivo edge (1505) of the base. In contrast, as can be seen in the cross section of FIG. 14C, in embodiments where the base is substantially or completely ex vivo, interference of any edge of the base with the trajectory of one or more channels is minimized.

In some instances, the base of a targeting system may, when the system is assembled and attached to a subject, remain substantially or completely ex vivo but the round end of the turret may protrude into the subject and thus be in vivo. In such instances, the amount that the rounded end of the turret that is in vivo when assembled may vary depending on the particular turret and base configuration.

In some instances, a targeting system may include a trajectory guide and a multicomponent turret-based system that is substantially ex vivo. In some instances, the trajectory guide of such a system may be configured with styles of such a length that, when the styles are inserted into the channels of the turret the trajectory guide remains substantially or completely ex vivo. In some instances, the trajectory guide of such a system may be configured with styles of such a length that, when the styles are inserted into the channels of the turret the styles of the trajectory guide exceed beyond the rounded end of the turret and are thus positions at least partially in vivo.

The base configured to receive the round end of the adjustable turret may also serve to attach the assembled multi-component device to a tissue surface of a subject. Any convenient means of attaching the base to the surface of the subject may be employed and the base may be configured and/or modified to allow for such varied methods of attachment. In some instances, e.g., as depicted in the embodiment of the base of FIG. 10, the base may include an attachment flange (1000) or a plurality of attachment flanges which may be arranged in any convenient orientation including but not limited to orthogonal to one or more walls of the base. The number of flanges on a base of the subject devices will vary and may include but is not limited to e.g., 1 or more, 2 or more, 3 or more, 4 or more, 5 or more, 6 or more, etc.

Figure 10:
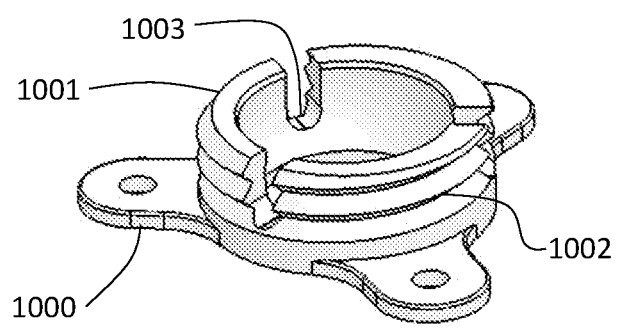
FIG. 10 depicts a base of a multi-component targeting device as described herein.

In some instances, the base may have a plurality of annular walls (1001) which collectively form a "socket" which receives the rounded end of the adjustable turret. The base may include threading on an external surface of the annular walls (1002) and a plurality of slots (1003) positioned between the annular walls. The configuration having slots between the treaded annular walls, e.g., as depicted in FIG. 10, allow for essentially uniform compression on the rounded end of the adjustable turret to be created when the locking collar is treaded to the base and tightened. While being dimensioned to receive the spherical end of the adjustable turret, the size of the base may vary. For example, in some instances, the area covered by the base may range from less than 1 $cm^2$ to 100 $cm^2$ or more including but not limited to e.g., 1 $cm^2$ to 100 $cm^2$, 1 $cm^2$ to 75 $cm^2$, 1 $cm^2$ to 50 $cm^2$, 1 $cm^2$ to 25 $cm^2$, 1 $cm^2$ to 20 $cm^2$, 1 $cm^2$ to 15 $cm^2$, 1 $cm^2$ to 10 $cm^2$, 1 $cm^2$ to 9 $cm^2$, 1 $cm^2$ to 8 $cm^2$, 1 $cm^2$ to 7 $cm^2$, 1 $cm^2$ to 6 $cm^2$, 1 $cm^2$ to 5 $cm^2$, 10 $cm^2$ to 100 $cm^2$, 25 $cm^2$ to 100 $cm^2$, 50 $cm^2$ to 100 $cm^2$, 75 $cm^2$ to 100 $cm^2$, etc.

Figure 11:
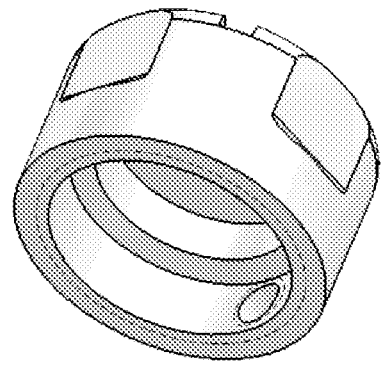
FIG. 11 depicts a cap configured for attachment to a base of a multi-component targeting device as described herein.

In some instances, the device or system may further include a cap to cover the device or system and/or keep any openings free of debris when not in use. Useful caps include but are not limited to e.g., a cap configured to cover the distal end of the turret, a cap configured cover the base, etc. In some instances, owing to the removability of the turret from the base, e.g., by "snapping out" the turret from the base, the turret may be removed leaving an exposed hole through the center of the base. In some instances, the system or device may include a cap configured to fit on top of the base when the turret is removed to cover any exposed hole within the center of the base. One embodiment of a cap configured to cover the base when the turret is removed is depicted in FIG. 11. Caps as described herein may be held in place by any convenient means, including e.g., compression force, a fastener, etc. As such, a cap may or may not be threaded. For example, in some instances, a cap is configured with internal threading compatible with the external threading on the annular walls of the base such that the cap may be screwed into place, e.g., when the device is not in use.

As described in some detail above, various components of the devices and systems described herein may be symmetrical or asymmetrical. Symmetry of components of the device and systems includes internal symmetry and symmetry relative to another component, e.g., where two components are positioned or attached symmetrically.

In some instances, the presence of an asymmetry in a component of a device or system may provide a reference point during imaging to orient the image, i.e., provide a reference point to differentiate one side of an imaged trajectory guide from another side of the imaged trajectory guide. Any asymmetry in the system, e.g., that can be seen visually or that can be identified on a MRI-image, may be utilized in orienting one or more components of the system.

Figure 12:
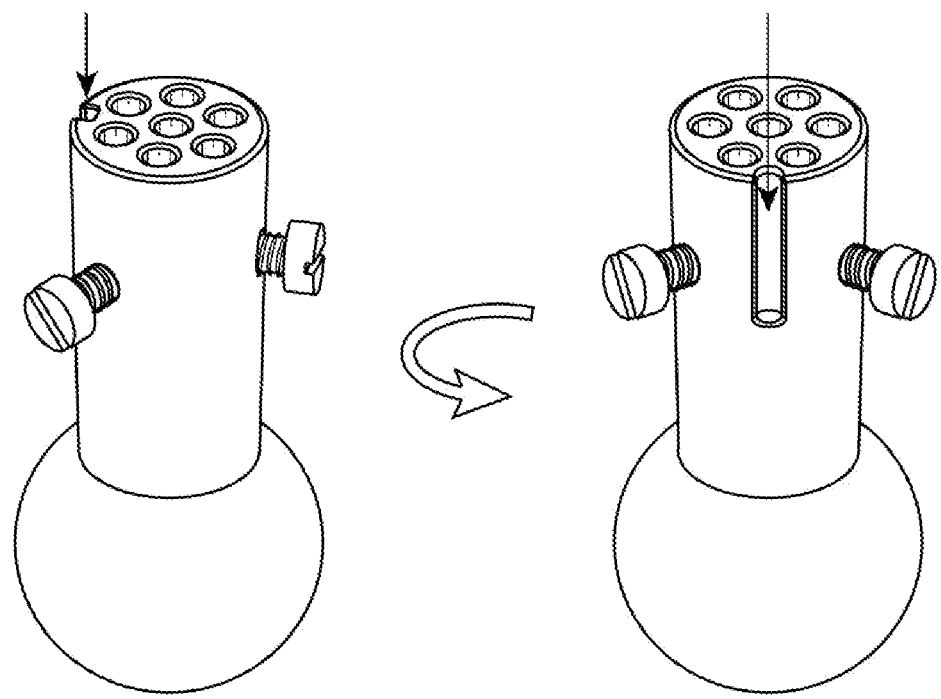
FIG. 12 depicts an adjustable turret of a targeting device having an asymmetry groove.

For example, in some instances, the turret may contain an asymmetry including but not limited to e.g., a groove or indentation, to serve as a reference point. As an example, in the embodiment of a turret depicted in FIG. 12, the turret is configured with a groove (arrow) in one position on the turret to serve as a reference point used to orient the turret and/or identify the particular channels of the turret. Other useful features that may serve as an asymmetry include but are not limited to e.g., flat sections, screw holes, screws, etc.).

Figure 13:
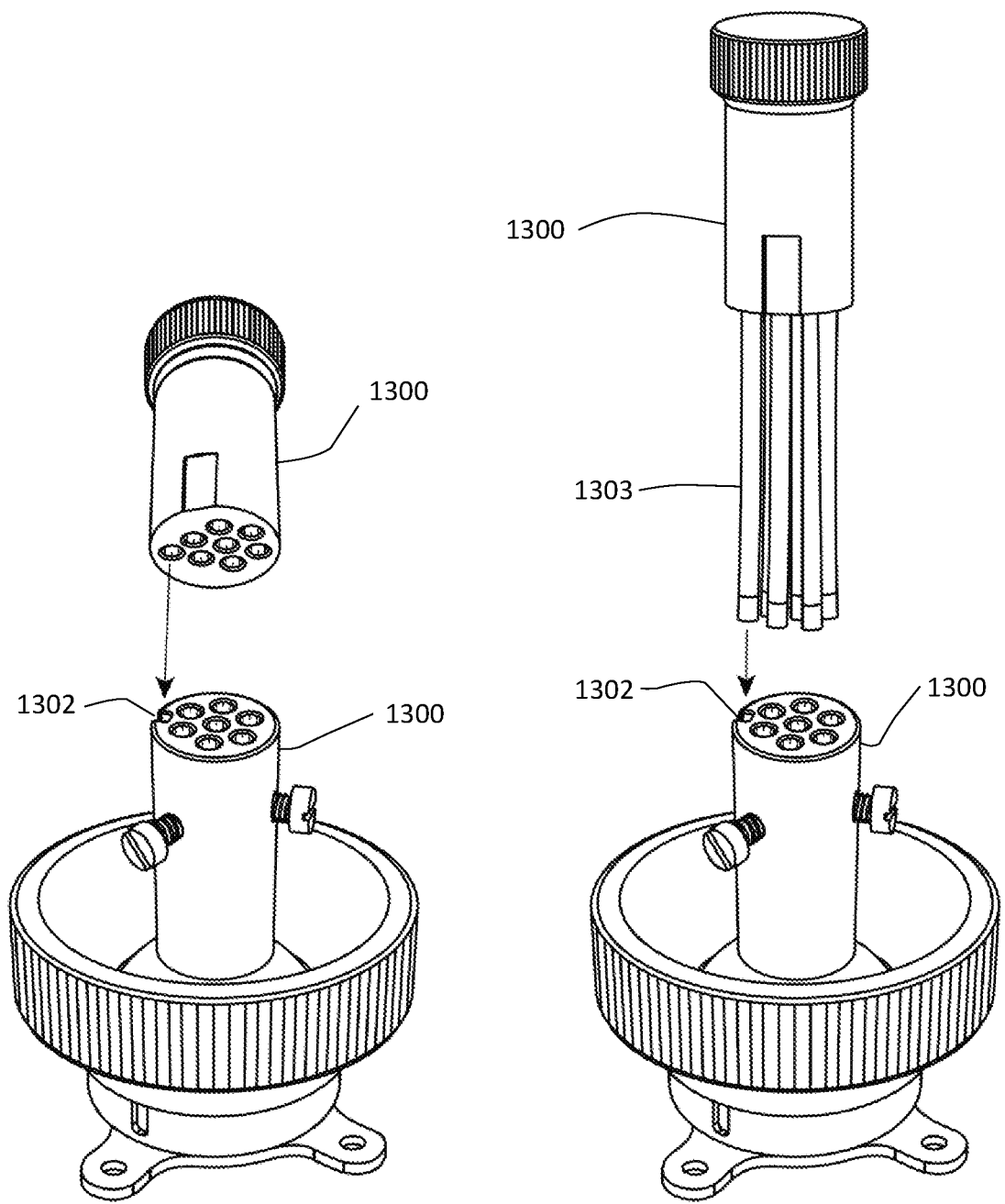
FIG. 13 depicts a trajectory guide and targeting device system according to an embodiment described herein.

In some instances, the styles of a trajectory guide may be arranged asymmetrically such that, when viewed on an MRI-imager the asymmetry may serve as a reference point and a means of indicating to a user or a computer to the orientation of the targeting guide. For example, in one embodiment, depicted in FIG. 13 the trajectory guide (1300) (pictured on the left without styles attached and on the right with styles attached) has an asymmetrical configuration of styles. All but one style of this asymmetric configuration corresponds to the symmetric channels of the adjustable turret (1301). The turret also contains an asymmetric groove (1302). In the embodiment depicted, the asymmetric style (1303) may be configured to align with the asymmetric groove (1302). Accordingly, when the styles of the trajectory guide are inserted into the channels and groove of the turret the asymmetric style provides orientation of the targeting system and identification of each channel of the turret using MRI imaging.

Systems of the instant disclosure may further include an MRI imager. As used herein the term "MRI imager" generally refers to any device that functions using the principles of nuclear magnetic resonance imaging that are well-known to the ordinary skilled artisan and include but are not limited to those devices commercially available in the relevant medical arts MRI.

Biomedical Systems

Aspects of the instant disclosure include targeted devices that may further include one or more biomedical systems for delivering a targeted therapy to a subject. The subject biomedical systems will include any suitable device for delivering or performing any of the therapeutic methods described above, provided the device or the operable portion thereof is able to be physically introduced through a channel of a targeting device as described herein.

In some instances, a biomedical system applied using a targeting device of the instant disclosure is a therapeutic delivery device, e.g., a drug delivery device. Any suitable drug delivery device may find use in the subject devices including but not limited to e.g., a needle, a cannula, an osmotic pump, a catheter, etc.

In some instances, a biomedical system applied using a targeting device of the instant disclosure is a therapy device for delivering electrical current or other energy (e.g., heat) to a desired area of a subject. Any suitable probe for therapeutic delivery may find use in the subject devices including but not limited to e.g., a heat probe, an electrode, etc.

In some instances, the biomedical device targeted through a channel of the subject targeting system may include a depth stop. As used herein, the term "depth stop" refers to any mechanism used to prevent the adverse and undesirable over-insertion of the biomedical device into the subject. In some instances, such depth stops may be configured of a sufficient diameter to prevent the biomedical device from proceeding into the subject when the depth stop contacts the adjustable turret of the targeting device.

In some instances, biomedical systems of the instant disclosure include an integrated system having a MRI-imaging unit a targeting device with a corresponding biomedical therapy device. In such systems, the MRI-imaging unit, and optionally the targeting and/or delivery device, may be communicably connected to a processing device, such as a processor.

Figure 16:
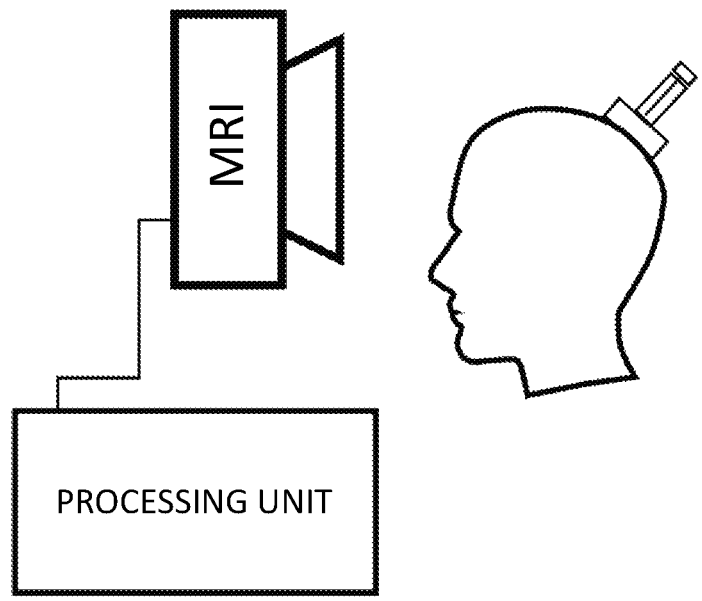
FIG. 16 depicts a targeting system as described herein.

For example, in the embodiment depicted in FIG. 16, a system of the instant disclosure may include a targeting device with a targeting guide in a positional relationship to an MRI-imager ("MRI") to allow the MRI-imager to image the targeting device, targeting guide and the desired region of treatment of the subject. The MRI-imager may further be connected to a processing unit configured to receive the images from the MRI-imager, process the images and output the results. In some instances, processing of the images may include determining the trajectory of one or more channels of the targeting device and displaying or otherwise reporting the result to a user. In some instances, the processor-connected MRI-imager outputs the MRI images of the trajectory guide but any determination of the trajectory is made manually.

Figure 17:
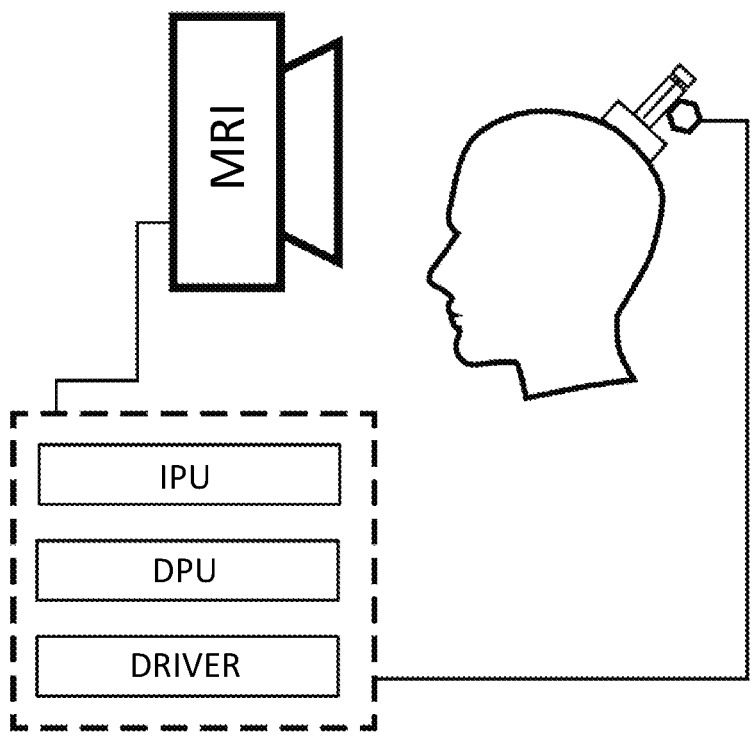
FIG. 17 depicts a targeting system as described herein.

The embodiment depicted in FIG. 17, extends the embodiment of FIG. 16, where the system further include a connection between the processing unit and the targeting device. A connection between the processor and the targeting device may be used for a variety of non-mutually exclusive purposes. For example, in some instances, the delivery of an agent, electrical current or other therapy may be computer controlled by the processor such that, upon proper targeting, the computer, with or without further user input, triggers delivery.

In some instances, the targeting adjustments of the targeting device may be computer controlled. For example, the targeting device may further include one or more computer controlled motors or actuators operably coupled to the adjustable turret such that targeting adjustments may be computer controlled. Computer controlled targeting adjustments may be dependent on user input defining the adjustment or the adjustment may be automated based on a computer calculated trajectory and adjustment. Whether the adjustment is manual or computer determined, the described systems will generally include at least a user input to define the target region of the subject.

The processor unit of FIG. 17, include an image processing unit (IPU) configured to receive the image from the MRI-imager, a data processing unit (DPU) configured to determine the trajectory from data received from the IPU, calculate the difference between the determined trajectory and a user inputted desired trajectory and signal any necessary adjustment. In some instances, a signaled necessary adjustment may be transferred to a computer driver ("DRIVER") that translates the signal to movement instructions such that either a user or motor/actuator driven components perform the necessary adjustment of the targeting device. The delivery of the therapy to the subject may also be user controlled or may be computer controlled e.g., by one or more drivers used to trigger a delivery signal.

Figure 18:
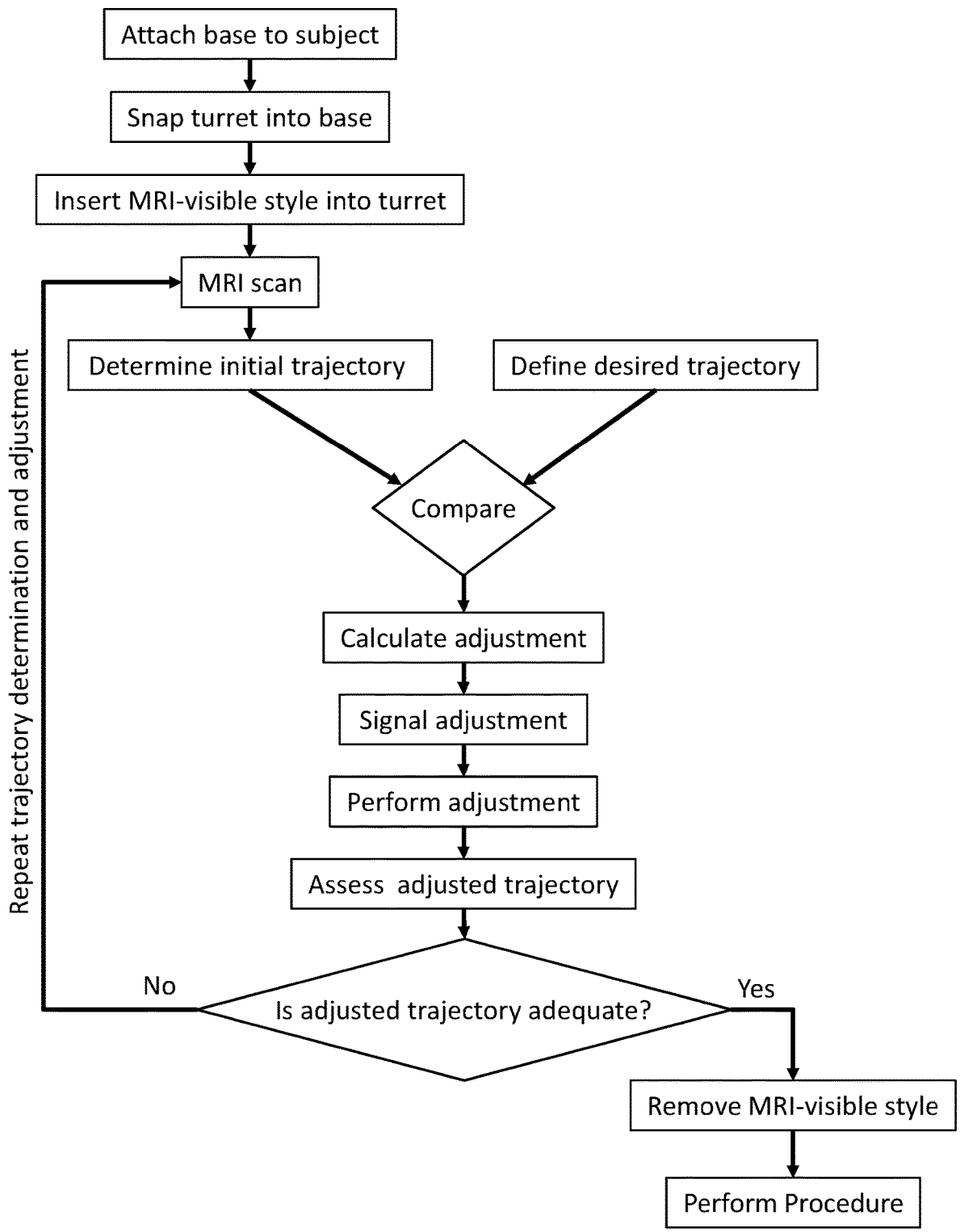
FIG. 18 provides a flowchart demonstrating the movement through a targeting system process as described herein.

The steps of a process for performing a herein disclosed method of targeting using a described system to deliver a procedure to a subject is outlined in FIG. 18. Essentially, using a herein described apparatus, the base of a targeting device is attached to a subject and the turret is snapped into the base. A targeting guide is used to insert an MRI-visible style into the turret and an MRI scan is performed. From the MRI scan the initial trajectory is determined and the system compares the determined trajectory to a user inputted desired trajectory. The system calculates an adjustment based on the comparison and signals the adjustment to the user of a component of the system configured to make the adjustment. The adjustment is performed, either by the user or the system and the adjusted trajectory is assessed. If the adjusted trajectory is sufficient the MRI-visible style may be removed and the treatment may be delivered. If the adjusted trajectory is insufficient, the system may loop back to the MRI scan and may repeat the trajectory determination and adjustment. As noted, the individual processes outlined in FIG. 18 may, where appropriate be computer controlled.

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer harddrive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

Computer Readable Media

The instant disclosure includes computer readable medium, including non-transitory computer readable medium, which stores instructions for methods described herein. Aspects of the instant disclosure include computer readable medium storing instructions that, when executed by a computing device, cause the computing device to perform one or more steps of a method as described herein.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An adjustable targeting system, the system comprising:
an adjustable turret comprising a distal end, a spherical end and one or more channels running from the distal end to the spherical end; and
a base, comprising:
a plurality of annular walls forming a socket dimensioned to receive the spherical end;
a plurality of slots positioned between the plurality of annular walls; and
a flange orthogonal to at least one of the annular walls for affixing the base to a tissue surface of a subject, wherein the channel is configured for insertion of a MRI-visible style affixed at one end to a flat surface of a solid support of a trajectory guide into the channel.

2. The system of claim 1, further comprising a locking collar comprising threading on an internal surface compatible with threading on the external surface of the base, wherein turning the locking collar a first direction compresses the spherical end to lock the adjustable turret in a desired trajectory and turning the locking collar a second direction decompresses the spherical end to allow for retargeting of the trajectory of the adjustable turret, and wherein turning the locking collar the first direction compresses the spherical end between the base and the locking collar to lock the adjustable turret in a desired trajectory.

3. The system of claim 1, further comprising a locking collar comprising threading on an internal surface compatible with threading on the external surface of the base, wherein turning the locking collar a first direction compresses the spherical end to lock the adjustable turret in a desired trajectory and turning the locking collar a second direction decompresses the spherical end to allow for retargeting of the trajectory of the adjustable turret, and wherein turning the locking collar the first direction compresses the spherical end between the plurality of annular walls of the socket to lock the adjustable turret in a desired trajectory.

4. The system of claim 1, wherein the adjustable targeting system is configured such that when affixed to the tissue surface of the subject the base and the locking collar are ex vivo.

5. The system of claim 1, wherein the adjustable targeting system is configured such that when affixed to the tissue surface of the subject the adjustable turret is ex vivo.

6. The system of claim 1, wherein the spherical end comprises a flat portion opposite the distal end that comprises openings to the one or more channels.

7. The system of claim 1, wherein the spherical end and the flat portion are dimensioned such that, when inserted into the socket, the flat portion is flush with the bottom surface of the base.

8. The system of claim 7, wherein the locking collar comprises a knurled external surface to provide grip.

9. The system of claim 1, wherein the base comprises a plurality of flanges orthogonal to at least one of the annular walls.

10. The system of claim 1, further comprising a trajectory guide comprising:
a solid support comprising a flat surface; and
a MRI-visible style comprising a lumen comprising a contrast agent, wherein the MRI-visible style is affixed at one end to the flat surface and dimensioned for insertion into a channel of the adjustable turret affixed to a tissue surface of the subject thereby allowing targeting of the channel by visualizing the trajectory of the inserted MRI-visible style using an MRI imager.

11. The system of claim 10, wherein the system further comprises an MRI imager positioned to image the MRI-visible style of the trajectory guide when the MRI-visible style is inserted into the channel of the adjustable turret.

12. An adjustable targeted delivery system, the system comprising:
an adjustable targeting system according to claim 1; and
a delivery device or electrode dimensioned for insertion into the channel of the adjustable turret.

13. The system of claim 12, wherein the delivery device or electrode comprises a depth stop positioned at a point along the length of the delivery device or electrode to prevent inserting the delivery device into the channel past said point.

* * * * *

UNITED STATES PATENT AND TRADEMARK OFFICE
CERTIFICATE OF CORRECTION

| | | |
|---|---|---|
| PATENT NO. | : 12,318,183 B2 | Page 1 of 1 |
| APPLICATION NO. | : 17/689275 | |
| DATED | : June 3, 2025 | |
| INVENTOR(S) | : Krystof S. Bankiewicz et al. | |

It is certified that error appears in the above-identified patent and that said Letters Patent is hereby corrected as shown below:

In the Specification

In Column 8, Line 66, delete "www(dot)ast(dot)org)." and insert -- www(dot)last(dot)org). --.

In Column 17, Line 22, delete "targted" and insert -- targeted --.

In Column 19, Line 56, delete "gadoxeticacid," and insert -- gadoxetic acid, --.

In Column 29, Line 13, delete "e.g.," and insert -- (e.g., --.

Signed and Sealed this
Fifth Day of August, 2025

Coke Morgan Stewart
*Acting Director of the United States Patent and Trademark Office*